(12) United States Patent
Berry et al.

(10) Patent No.: US 7,928,123 B2
(45) Date of Patent: Apr. 19, 2011

(54) COMPOUNDS WHICH MODULATE THE CB2 RECEPTOR

(75) Inventors: Angela Berry, Gaylordsville, CT (US); Pier Francesco Cirillo, Woodbury, CT (US); Doris Riether, Newtown, CT (US); David Thomson, Ridgefield, CT (US); Renee M. Zindell, New Milford, CT (US); Nigel Blumire, Didcot (GB); Chandana Chowdhury, Manchester (GB); Monika Ermann, Wantage (GB); James Edward Jenkins, Hungerford (GB); Innocent Mushi, Didcot (GB); Christopher Francis Palmer, Abingdon (GB); Malcolm Taylor, Didcot (GB)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 603 days.

(21) Appl. No.: 11/854,607

(22) Filed: Sep. 13, 2007

(65) Prior Publication Data
US 2008/0081822 A1 Apr. 3, 2008

Related U.S. Application Data

(60) Provisional application No. 60/826,819, filed on Sep. 25, 2006.

(51) Int. Cl.
*C07D 213/02* (2006.01)
*A61K 31/44* (2006.01)

(52) U.S. Cl. ........ 514/313; 514/318; 514/326; 514/352; 514/361; 514/363; 514/371; 514/375; 514/380; 514/407; 514/459; 546/159; 546/193; 546/209; 546/309; 548/128; 548/139; 548/195; 548/222; 548/246; 548/265.4; 548/372.5; 549/426

(58) Field of Classification Search .................. None
See application file for complete search history.

(56) References Cited

U.S. PATENT DOCUMENTS

| | | | |
|---|---|---|---|
| 3,116,284 A | 12/1963 | Testa | |
| 3,117,128 A | 1/1964 | Mooradian | |
| 3,577,462 A | 5/1971 | Bruce et al. | |
| 3,966,809 A | 6/1976 | Baker et al. | |
| 4,257,954 A | 3/1981 | Schmidt et al. | |
| 4,535,087 A | 8/1985 | Spatz | |
| 4,672,065 A | 6/1987 | Spatz | |
| 4,859,707 A | 8/1989 | Loftsson et al. | |
| 5,256,658 A | 10/1993 | Hsi et al. | |
| 5,428,037 A | 6/1995 | Pascal et al. | |
| 5,475,130 A | 12/1995 | Sato et al. | |
| 5,571,921 A | 11/1996 | Bender et al. | |
| 5,583,147 A | 12/1996 | Ko et al. | |
| 5,656,634 A | 8/1997 | Chang et al. | |
| 5,847,153 A | 12/1998 | Warpehoski et al. | |
| 5,968,929 A | 10/1999 | Blythin et al. | |
| 6,057,371 A | 5/2000 | Glennon | |
| 6,176,442 B1 | 1/2001 | Eicher et al. | |
| 6,221,866 B1 | 4/2001 | Brendel et al. | |
| 6,355,653 B1 | 3/2002 | Trottmann et al. | |
| 6,359,009 B1 | 3/2002 | Diehl et al. | |
| 6,410,792 B1 | 6/2002 | Connell et al. | |
| 6,414,011 B1 | 7/2002 | Hogenkamp et al. | |
| 6,437,177 B1 | 8/2002 | Warpehoski et al. | |
| 6,453,795 B1 | 9/2002 | Eicher et al. | |
| 6,528,529 B1 | 3/2003 | Brann et al. | |
| 6,573,278 B2 | 6/2003 | Mittendorf et al. | |
| 6,610,711 B2 | 8/2003 | Armer et al. | |
| 6,737,418 B2 | 5/2004 | Hogenkamp et al. | |
| 7,476,756 B2 | 1/2009 | Almario-Garcia et al. | |
| 7,595,397 B2 | 9/2009 | Zindell et al. | |
| 2002/0099035 A1 | 7/2002 | Sandanayaka et al. | |
| 2004/0067999 A1 | 4/2004 | Block et al. | |
| 2004/0242913 A1 | 12/2004 | Ducray et al. | |
| 2005/0059663 A1 | 3/2005 | Martin et al. | |
| 2005/0182108 A1 | 8/2005 | Carson | |
| 2006/0061726 A1 | 3/2006 | Okuyama | |
| 2006/0079557 A1 | 4/2006 | Dolle et al. | |
| 2007/0021403 A1 | 1/2007 | Abouabdellah et al. | |
| 2007/0021430 A1 | 1/2007 | Chen et al. | |
| 2007/0093501 A1 | 4/2007 | Kubo et al. | |
| 2007/0179126 A1 | 8/2007 | Casellas et al. | |
| 2007/0191340 A1 | 8/2007 | Zindell et al. | |
| 2007/0213311 A1 | 9/2007 | Li | |
| 2008/0039464 A1 | 2/2008 | Berry et al. | |

(Continued)

FOREIGN PATENT DOCUMENTS

CH 312963 * 4/1956

(Continued)

OTHER PUBLICATIONS

Sandoz Ltd, English Translation of CH 312963 filed Apr. 1956.*
Robert J. Watson, et al., "An enantioselective synthesis of sulphonamide hydroxamic acids as matrix metalloproteinase inhibitors", Pergamon, Tetrahedron Letters 43 (2002) 683-685.
Monika Ermann, et al., "Arylsulfonamide CB2 receptor agonists: SAR and optimization of CB2 selectivity", Bioorganic and Medicinal Chemistry Letters 18 (2008) 1725-1729.
Keith A. Sharkey, et al., "CB2 cannabinoid receptors: new vistas", The first International Conference devoted to studies of the CB2 cannabinoid receptor. Banff, Alberta, Canada, May 31-Jun. 3, 2007.

(Continued)

*Primary Examiner* — Zinna N Davis
(74) *Attorney, Agent, or Firm* — Michael P. Morris; Anthony P. Bottino

(57) ABSTRACT

Compounds of formula (I)

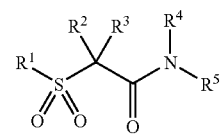

are disclosed. Compounds according to the invention bind to and are agonists, antagonists or inverse agonists of the CB2 receptor, and are useful for treating inflammation. Those compounds which are agonists are additionally useful for treating pain.

8 Claims, No Drawings

U.S. PATENT DOCUMENTS

| | | | |
|---|---|---|---|
| 2008/0064690 | A1 | 3/2008 | Atkinson et al. |
| 2009/0163545 | A1 | 6/2009 | Goldfarb |
| 2009/0275611 | A1 | 11/2009 | Riether et al. |
| 2010/0009964 | A1 | 1/2010 | Berry et al. |
| 2010/0029644 | A1 | 2/2010 | Riether et al. |
| 2010/0076029 | A1 | 3/2010 | Bartolozzi et al. |
| 2010/0081644 | A1 | 4/2010 | Bartolozzi et al. |
| 2010/0261708 | A1 | 10/2010 | Cirillo et al. |

FOREIGN PATENT DOCUMENTS

| | | | |
|---|---|---|---|
| DE | 1080563 | B | 12/1957 |
| EP | 0628555 | | 12/1994 |
| EP | 0929519 | | 7/1999 |
| EP | 0970046 | | 1/2000 |
| EP | 1790641 | A1 | 5/2007 |
| FR | 2866885 | A1 | 9/2005 |
| FR | 2872813 | A1 | 1/2006 |
| GB | 853799 | A | 11/1960 |
| GB | 884258 | A | 12/1961 |
| JP | 61017955 | | 2/1986 |
| JP | 61027905 | U | 2/1986 |
| JP | 61027955 | A | 2/1986 |
| JP | 61126071 | A | 6/1986 |
| JP | 2003155285 | | 5/2003 |
| WO | 9405628 | | 3/1994 |
| WO | 94/07607 | A1 | 4/1994 |
| WO | 9407607 | | 4/1994 |
| WO | 9626925 | A1 | 9/1996 |
| WO | 97/12683 | A1 | 4/1997 |
| WO | 97/12687 | A1 | 4/1997 |
| WO | 9712687 | | 4/1997 |
| WO | 97/20590 | A1 | 6/1997 |
| WO | 9746556 | | 12/1997 |
| WO | 9808295 | | 2/1998 |
| WO | 9813340 | | 4/1998 |
| WO | 9838163 | A1 | 9/1998 |
| WO | 0100573 | | 1/2001 |
| WO | 0129007 | | 4/2001 |
| WO | 0164651 | | 9/2001 |
| WO | 02051806 | | 7/2002 |
| WO | 02062750 | | 8/2002 |
| WO | 03037274 | | 5/2003 |
| WO | 03055482 | | 7/2003 |
| WO | 03/000807 | A1 | 12/2003 |
| WO | 2004000807 | | 12/2003 |
| WO | 2004/014825 | A1 | 2/2004 |
| WO | 2004018433 | | 3/2004 |
| WO | 2004029027 | | 4/2004 |
| WO | 2004/050643 | A2 | 6/2004 |
| WO | 2004/060882 | A1 | 7/2004 |
| WO | 2004/099200 | A1 | 11/2004 |
| WO | 2004099205 | | 11/2004 |
| WO | 2005/027837 | A2 | 3/2005 |
| WO | 2005/040355 | A2 | 5/2005 |
| WO | 2005040355 | | 5/2005 |
| WO | 2005/085227 | A1 | 9/2005 |
| WO | 2006012227 | | 2/2006 |
| WO | 2006060461 | | 6/2006 |
| WO | 2006/080040 | A1 | 8/2006 |
| WO | 2006/100502 | A1 | 9/2006 |
| WO | 2006095159 | | 9/2006 |
| WO | 2006117461 | A2 | 11/2006 |
| WO | 2007020502 | A2 | 2/2007 |
| WO | 2007054770 | A2 | 5/2007 |
| WO | 2007070760 | | 6/2007 |
| WO | 2007070760 | A2 | 6/2007 |
| WO PCT/US2006/061726 | | A2 | 6/2007 |
| WO | 2007080382 | A1 | 7/2007 |
| WO | 2007/102059 | A1 | 9/2007 |
| WO | 2007118041 | A1 | 10/2007 |
| WO PCT/US2007/065749 | | A1 | 10/2007 |
| WO PCT/US2007/074076 | | A2 | 1/2008 |
| WO | 2008023159 | A1 | 2/2008 |
| WO PCT/US2008/081822 | | A1 | 2/2008 |
| WO | 2008048914 | A1 | 4/2008 |
| WO PCT/US2007/078341 | | A1 | 4/2008 |
| WO PCT/US2007/081342 | | A1 | 4/2008 |
| WO | 2008064054 | | 5/2008 |
| WO | 2008098025 | A1 | 8/2008 |
| WO | 2008104994 | A2 | 9/2008 |
| WO | 2009055357 | A1 | 4/2009 |
| WO | 2009061652 | A1 | 5/2009 |
| WO | 2009077533 | A1 | 6/2009 |
| WO | 2009105509 | A1 | 8/2009 |
| WO | 2009140089 | A2 | 11/2009 |
| WO | 2010005782 | A1 | 1/2010 |
| WO | 2010036630 | A2 | 4/2010 |
| WO | 2010036631 | A2 | 4/2010 |
| WO | 2010077836 | A2 | 7/2010 |
| WO | 2010096371 | A2 | 8/2010 |
| WO | 2010147791 | A1 | 12/2010 |
| WO | 2010147792 | A2 | 12/2010 |

OTHER PUBLICATIONS

Monika Ermann, et al., "Discovery of a novel class of CB2 receptor agonists". Presented at the 14th SCI-RSC Medicinal Chemistry Symposium, Churchill College, Cambridge, UK, Sep. 23-26, 2007.

Monika Ermann, et al., "Discovery of a novel class of CB2 receptor agonists". Presented at the Cambridge Healthcare Institute's 15th International Molecular Medicine Tri-Conference, Moscone Convention Center, San Francisco, CA, USA. Mar. 25-28, 2008.

Julius Troeger, et al., "Regarding sulfonated Butyric Acids". From the Laboratory for Pharmaceutical and Synthetic Chemistry of the Braunschweig Institute of Technology. 40, 506.

Renee Zindell, et al., "Discovery of a novel class of CB2 agonists". General Poster Session. The 235th ACS National Meeting, New Orleans, LA, USA. Apr. 6-10, 2008.

A.V. Anisimov, et al., "Synthesis of Sulfonyl and Sulfenyl Derivatives of Pyridine and 1,2,4-Triazole". Russian Journal of Organic Chemistry, 2006, vol. 42, No. 6, pp. 918-921.

Graham J. Atwell, et al., "Relationships between Structure and Kinetics of Cyclization of 2-Aminoaryl Amides: Potential Prodrugs of Cyclization-Activitated Aromatic Mustards"., XP-002465787, J. Med. Chem, 1994, 37, 371-380.

N. G. Clark, et al., "The Fungicidal Activity of Substituted Acetanilides and Related Compounds". XP-002465783, vol. 55, p. 839-851.

Soad A. M. El-Hawash, et al., "Synthesis and invitro-Anticancer and Antimicrobial Evaluation of Some Novel Quinoxalines Derived from 3-Phenylquinoxaline-2(1H)-thione". XP-002465790, Arch. Pharm. Chem. Life Sci, 2006, 339, p. 437-447.

Wilfrid J. Evans, et al., "A Rearrangement of Carbamyl-sulphones and -sulphides". XP-009094355, p. 329-331.

Lamar Field, et al., "Grignard Reagents of Sulfones. IV. Reactions with Nitriles, Esters and an Isocyanate". XP002465788, Mar. 30, 1956.

Von W. Grothe, et al. "Effect of Potassium Sulfhydrate etc. on Chloroacetylanilides".

Xian Huang, et al., "A Novel Synthesis of Sulfones via the O,O-Diethylphosphorotellurite Ion-assisted Coupling of Arenesulfonyl Chlorides with Active Halides". XP 009094356, Synthetic Communications, 20(15), 2291-2291-2295 (1990).

Brian Iddon, et al., "Polyhalogenoaromatic Compounds. Part 42. C N.m.r. Spectra of Polyhalogeno-pyridines and -pyrimidines". XP009094360, Ramage Laboratories, Dept of Chemistry and Applied Chemistry, University of Salford, Salford M5 4WT.

Katsuyuki Ishii, et al., "Smiles Rearrangement of 2-(1-Methyl-1H-tetrazol-5-ylthio)acetamides and their Sulfonyl Derivatives". XP009094359, Chem. Pharm. Bull. 39(12) 3331-3334 (1991).

Erkki Kolehmainen, et al., "a-Phenylsulfonyl-N-arylacetamides (a-phenylsulfonylacetanilides): H, C and N NMR spectral characterization". XP002465784, Magnetic Resonance in Chemistry, 2000, 38: 384-385.

A.M. Mahmoud, et al., "Synthesis and Biological Activity of Some new 2-(N-Substituted Carboxamidomethyl Thio)-Naphth[1,2-d]Oxazoles-Part V". XP002068972, J. Indian Chem. Soc., vol. LIX, May 1982, pp. 675-677.

H. Schaefer, et al. "On the Synthesis of 4-aminoquinolines and -quinolinones-(2) from Anthranilonitrile" Chemistry Department of the Technical University of Dresden, Journal for Practical Chemistry, vol. 321, No. 4, pp. 695-698.

Robert C. Tweit, et al., "Synthesis of Antimicrobial Nitroimidazolyl 2-Sulfides, -Sulfoxides, and -Sulfones". Dept. of Chemical and Biological Research, Searle Laboratories, Chicago, IL, USA, Mar. 29, 1973, pp. 1161-1169.

Guangfu Yang, et al., "Synthesis and Bioactivity of Novel Triazolo [1,5-a]Pyrimidine Derivatives[3]". XP002465786, Heteroatom Chemisry, vol. 12, No. 6, 2001, p. 491-496.

Venkatesan Aranapakam, et al., "Synthesis and Structure—Activity Relationship of α-Sulfonylhydroxamic Acids as Novel, Orally Active Matrix Metalloproteinase Inhibitors for the treatment of Osteoarthritis", J. Med. Chem., 2003, vol. 46, p. 2361.

Venkatesan Aranapakam, et al., "Synthesis and Structure—Activity relationship of n-Substituted 4-Arylsulfonylpiperidine-4-hydroxamic Acids as Novel, Orally Active matrix Metalloproteinase Inhibitors for the treatment of Osteoarthritis", J. Med. Chem., 2003, vol. 46, p. 2376.

Venkatesan Aranapakam, et al., "Synthesis and Structure—Activity relationships of 4-alkynyloxy Phenyl Sulfanyl, Sulfinyl, and Sulfonyl Alkyl Hydroxamates as Tumor Necrosis Factor-α Converting Enzyme and Matrix Metalloproteinase Inhibitors", J. Med. Chem., 2004, vol. 47, p. 6255.

Ángel Arévalo-Martin, et al., "Therapeutic Action of Cannabinoids in a Murine model of Multiple Sclerosis", J. of Neuroscience, 2003, vol. 23, No. 7, p. 2511.

David Baker, et al., "Cannabinoids control spasticity and tremor in a multiple sclerosis model", Nature, 2000, vol. 404, p. 84.

Carine Binisti, et al., "Structure-Activity relationships in platelet-activating factor (PAF). 11-From PAF-antagonism to phospholipase $A_2$ inhibition: syntheses and structure-activity relationships in 1-arylsulfamido-2-alkylpiperazines", Eur. J. Med. Chem., 2001, vol. 36, p. 809.

Peter J. Brown, et al., "A Ureido-Thioisobutyric Acid (GW9578) is a Subtype-Selective PPARα Agonist with Potent Lipid-Lowering Activity", J. Med. Chem. 1999, vol. 42, p. 3785.

Nancy E. Buckley, et al., "Immunomodulation by cannabinoids is absent in mice deficient for the cannabinoid $CB_2$ receptor", Eur. J. Pharmacology, 2000, vol. 396, p. 141.

Anne Marie Faucher, et al., "Discovery of Small-Molecule Inhibitors of the ATPase Activity of Human Papillomavirus E1 Helicase", J. Med. Chem., 2004, vol. 47, p. 18.

L. Field, et al., "Methyl p-Tolyl Sulfone", Organic Syntheses, Coll. vol. 4, p. 674, 1963; vol. 38, p. 62, (1958).

L. Hanus, et al., "HU-308: A specific agonist for $CB_2$, a peripheral cannabinoid receptor", PNAS, 1999, vol. 96, No. 25, p. 14228.

Mohab M. Ibrahim, et al., "Activation of $CB_2$ cannabinoid receptors by AM1241 inhibits experimental neuropathic pain: Pain inhibition by receptors not present in the CNS", PNAS, 2003, vol. 100, No. 18, p. 10529.

Akira Katoh, et al., "Synthesis of 6-(Bromoacetyl)Amino-2,3-Dimorpholino-Quinoxaline and Application to a new Fluorescence Derivatization Reagent of Fatty Acids for the High-Performance Liquid Chromatographic Analysis", Heterocycles, 1999, vol. 50, No. 1, p. 299.

Leon Katz, et al., "Hydrazine Derivatives. II. Ortho-Mercapto-Pyridinecarbohydrazides", Contribution from Schenley Laboratories, Inc., 1953, p. 711.

Thomas W. Klein, et al., "The Cannabinoid system and immune modulation", J. Leukocyte Biology, 2003, vol. 74, p. 486.

T. Philip Malan Jr., et al., "$CB_2$ cannabinoid receptor-mediated peripheral antinociception", Pain, 2001, vol. 93, p. 239.

Lowell D. Markley, et al., "Antipicornavirus activity of substituted Phenoxybenzenes and Phenoxypyridines", J. Med. Chem., 1986, vol. 29, p. 427.

A. G. Nackley, et al., "Selective Activation of Cannabinoid $CB_2$ Receptors Suppresses Spinal FOS Protein Expression and Pain Behavior in a rat Model of Inflammation", Neuroscience, vol. 119, 2003, p. 747.

Sidney R. Smith, et al., "The anti-inflammatory activities of cannabinoid receptor ligands in mouse peritonitis models", Eur. J. Pharmacology, 2001, vol. 432, p. 107.

Yoshifumi Ueda, et al., "Involvement of cannabinoid $CB_2$ receptor-mediated response and efficacy of cannabinoid $CB_2$ receptor inverse agonist, JTE-907, in cutaneous inflammation in mice", Eur. J. Pharmacology, 2005, vol. 520, p. 164.

Marja D. Van Sickle, et al., "Identification and Functional Characterization of Brainstem Cannabinoid $CB_2$ receptors", Science, 2005, vol. 310, p. 329.

Biliang Zhang and Ronald Breslow, "Ester Hydrolysis by a Catalytic Cyclodextrin Dimer Enzyme Mimic with a Metallobipyridyl Linking Group", J. Am. Chem. Soc., 1997, vol. 119, p. 1676.

Andreas Zimmer, et al., "Increased mortality, Hypoactivity, and hypoalgesia in cannabinoid CB1 receptor knockout mice", Proc. Natl. Acad. Sci. USA, 1999, vol. 96, p. 5780.

246020-62-2 registry copyright ACS on STN. Chemcats.

N. Lambeng, et al., "Discovery of a Novel Piperidinyl-Sulfonyl Benzoic Ester, Active as CB1 Agonist" Poster.

ISR PCT/US2007/078341, 2007.

ISR PCT/US2007/074076, 2007.

Meng-Yang Chang, et al, "Reaction of different a-sulfonyl acetamides with methyl acrylate". Tetrahedron 58 (2002) p. 5075-5080.

Michael C. Seidel, et al., "Reaction of Substituted 2-carbethoxyacetyl-aminopyridines and similar compounds with triethyl orthoformate and zinc chloride". Rohm and Haas Company, Spring House, Pennsylvania 19477.

R. Lesser, et al. "Homo-β-oxythionaphthene (4-Ketoisothiochromane", Charlottenburg, Industrial Chemistry Laboratory of the Institute of Technology, pp. 1642-1648, 1923.

J. Strating, et al. "Nucleophilic Additions to Bis-Tertiobutyl Sulfonyl Acetylene (Properties of the sulfonyl group XLIV [1])". University of Groningue, Organic Chemistry Laboratory, pp. 709-716.

I. E. Marx, et al., "Discovery of a-amidosulfones as potent and selective agonists of CB2: Synthesis, SAR, and pharmacokinetic properties". Bioorganic and Medicinal Chemistry Letters, 2008. In press, accepted manuscript.

Bair, K. W. et al., "(1-pyrenylmethyl)amino alcohols, a new class of antitumor DNA intercalators. Discovery and intial amine side chain structure-activity studies". Jornal of Medicinal Chemistry, vol. 33, 1990, pp. 2385-2393.

Baltzly, R. et al., "The preparation of N-mono-substituted and unsymmetrically disubstituted piperzines". Journal of American Chemical Society, vol. 66, 1944, pp. 263-265.

Baltzly,R. et al., "Unsymmetrically substituted piperazines. V. Piperazine ureas". The Journal of the American Chemical Society, vol. 76, 1954, pp. 1165-1166.

Balzarini, J. et al., "Antiretroviral activity of semisynthetic derivatives of glycopeptide antibiotics". J. Med. Chem., 2003, vol. 46, No. 13, pp. 2755-2764.

Caplus—RN 112298-90-5, retrieved from CAPLUS on Jan. 2, 2009.
Caplus—RN 262371-16-4, retrieved from CAPLUS on Jan. 2, 2009.
Caplus—RN 57992-82-2, retrieved from CAPLUS on Jan. 2, 2009.

Cartwright, D., et al., "Abnormal Nucleophillic substitution in 3-trichloromethylpyridine, its N-oxide and 3,5-Bis (trichloromethyl)pyridine". Tetrahedron, Elsevier Science Publishers, Amsterdam, vol. 51, No. 47, 1995, pp. 12791-12796.

ChemAbstract: 1990:497413, Zara-Kaczian, Acta Chimica Hungarica.

Chen, D. et al., "Preparation, properties, and synthetic potentials of novel boronates in a flourous version (flourous boronates)". Organic Letters, vol. 4. No. 6, 2002, pp. 1003-1005.

Cockcroft, X. L. et al., "Phthalazinones 2: optimization and synthesis of novel potent inhibitors of ply(ADP-ribose) polymerase". Bioorganic & Medicinal Chemistry Letters, 16, 2006, pp. 1040-1044.

Dav, Jr., R. A. et al., "Polarography of phenyl 2-thienyl and 2,2'-dithienyl ketones". 1953.

Fringuelli, F. et al., "Solvent-Free Al(OTi)3-catalyzed aminolysis of 1,2-Epoxides by 2-picolylamine: a key step in the synthesis of ionic liquids". Journal of Organic Chemistry, vol. 69, 2004, pp. 7745-7747.

Gao, M., et al "Synthesis of new carbon-11 labeled benzoxazole derivatives for PET imaging of 5-HT3 receptor", Science Direct, European Journal of Medicinal Chemistry, 43, 2008, pp. 1570-1574.

Gartst, M., et al., "Hydroformylation of bisolefinic amine derivatives catalyzed by cobalt and rhodium". Journal of Organic Chemistry, vol. 46, 1981, pp. 4433-4438.

Gavalda, et al N-Sulfonyl hydroxamate derivatatives as inhibitors of class II fructose-1, 6-diphosphate aldolase, Bioorganic & Medicinal Chemistry Letter, 2005, vol. 15, No. 24, pp. 5375-5377.

Goldschmidt,St. et al., "Biphenyl derivatives II. Basic 4-Biphenyl Compounds". Receuil Travaux Chimiques Des Pays-Bas, vol. 69, 1950, pp. 1109-1117.

Herndon, J. L. et al., "Ketanserin analogues. Structure-affinity relationships for 5-HT2 and 5-HT1c serotoninin receptor binding". J. Med. Chem, 1992, vol. 35, No. 26, pp. 4903-4910.

Igarashi, J. et al., "Improved synthesis of quinine alkaloids with the Teoc protective group". Tetrahedron letters, Elsevier, Amsterdam, vol. 46, No. 37, 2005, pp. 6381-6384.

Johansen et al., AMPA Receptor Agonists: Resolution, Configurational Assignment, and Pharmacology of (+)-(S)- and (−)-(R)-2-Amino-3-(3-Hydroxy-5-(2-Pyridyl) Isoxazol-4-yl)Propionic Acid (1-Py-AMPA); Chirality, New York, 1997, vol. 9, No. 3, pp. 274-280.

Leffler, M. T. et al. "N-Arylalkylmorpholines". Journal of the American Chemical Society, vol. 60, 1938, pp. 896-899.

Lutz, R. E. et al., "Antimalarials. Some piperazine derivatives". Journal of Organic Chemistry, vol. 12, 1947, pp. 771-775.

Miroshnikova, O.V. et al., "Structure-activity relationships in the series of eremomycin carboxamides". Journal of Antibiotics, vol. 53, No. 3, 2000, pp. 286-293.

Miyano, S, et al., "Kinetic Resolution of Racemic b-Hydroxy Amines by Enantioselective N-Oxide formation". Journal of Organic Chemistry, 1985, vol. 50, pp. 4350-4360.

Mohler, et al., "Nonsteroidal tissue selective androgen receptor modulators: a promising class of clinical candidates" University of Tennessee Health Science Center, Expert Opinion of Therapeutic Patents; Nov. 2005, vol. 15, No. 11, pp. 1565-1585.

Pollard, C. B. et al., "Some amides of piperazines". Journal of American Chemical Society, vol. 75, 1953, p. 491.

Revesz, L. et al., "Novel CCR1 antagonists with oral activity in the mouse collagen induced arthritis". Bioorganic and Medicinal Chemistry Letters, vol. 15, 2005, pp.5160-5164.

Sakuraba, S, et al., "Efficient asymmetric hydrogenation of a-amino ketone derivatives. A highly enantioselective synthesis of phenylephrine, levamisole, carnitine and propranolol". Chemical and Pharmaceutical Bulletin, Pharm. Society of Japan, 1995, vol. 43, No. 5, pp. 738-747.

Swanson, D. M. et al., "Identification and biological evaluation of 4-*(3-trifluoremethylpyridin-2-yl)piperzine-1-carboxylic acid (5-trifluoremethylpyridin-2-yl)amide, a high affinity TRPV1 (VR1) vanilloid receptor antagonist". Journal Med. Chem, 2005, 48, pp. 1857-1872.

Todorova, T. R., et al "Ring-enlargement and ring-opening reactions of 1,2-thiazetidin-3-one 1,1,-dioxides with ammonia and primary amines as nucleophiles". Helvetica Chimica Acta, vol. 82, 1999, pp. 354.

Troeger, J. and Uhde, R., "Ueber sulfonirte buttersauren", J. Prakt. Chem., 1899, vol. 59, p. 320.

Vogtle, M. M. et al., "An efficient protocol for the solid-phase synthesis of malondiamides". Molecules, 2005, 10, pp. 1438-1445. XP002481324.

Walker, G.N. et al., "Synthesis of varied heterocyclic and substituted aryl alkyl secondary amines, related Schiff bases, and amides". Journal of Medicinal Chemistry, vol. 9, 1966, pp. 624-630.

Yang, G. et al., "Synthesis and Bioactivity of Novel Triazolo [1,5-a]Pyrimidine Derivatives[3]". XP002465786, Heteroatom Chemistry, vol. 12, No. 6, 2001, p. 491-496.

Yordanova, K. et al. "New method for the synthesis of 2,4-disubstituted morpho-lines". Chemical Abstracts, vol. 97, No. 17, Oct. 25, 1982, Columbus, Ohio, USA Chemical Abstracts, vol. 97, No. 17, Oct. 25, 1982, Columbus, Ohio, vol. 115, No. 7, pp. 2635-2642.

Abstract in English for JP 61-027955, Feb. 7, 1986, Derwent.
Abstract in English for JP2003155285, May 27, 2003, Inventor: T. Makoto.

ChemAbstracts, Ukraine. Order Nos. T6110295, T5962700, T5962703 abstract and "Enamine Screening Library", Jan. 1, 2009, Enamine, 23 Alexandra Matrosova St., 01103 Kiev, Ukraine.

Abstract in English for JP 61-027905, Feb. 7, 1986, and WO199626925, Sep. 1996, Derwent Abstract.

Bruche, L. et al., "1,3-Dipolar Cycloadditions of 3,5-Dichloro-2,4,6-trimethylbenzonitrile Oxide to Phenylsulfonylallenes". Journal of Organic Chemistry, vol. 50, 1985, pp. 3206-3208, p. 3206, compounds 5a and 5b.

ChemAbstract: 246020-62-2 registry copyright ACS on STN, entered 1999. CHEMCATS.

Clark, N. G. et al., "The Fungicidal Activity of Substituted Acetanilides and Related Compounds". Biochemical Journal, 1953, vol. 55, p. 839-851.

EP Office Action dated Mar. 22, 2010.

Evans, W. J. et al., "A Rearrangement of Carbamyl-sulphones and -sulphides". Journal of the Chemical Society, 1936, p. 329-331.

Grothe, V. W. et al. "Effect of Potassium Sulfhydrate etc. on Chloroacetylanilides". Archiv der Pharmazie (Weinheim), vol. 238, 1980, p. 600-614.

Iddon, B. et al., "Condensed thiophen ring systems. Part SVII. A new synthesis of 10H-indeno[1,2-b][1] benzothiophen". Journal of the Chemical Society. Perkin Transactions 1, Chemical Socieity. Letchworth, GB. vol. 21, Jan. 1, 1974, pp. 2505-2508. ISSN: 0300-922X, p. 2506; compound 8.

Iddon, B. et al., "Polyhalogenoaromatic Compounds. Part 42. C N.m.r. Spectra of Polyhalogeno-pyridines and -pyrimidines". XP009094360, Ramage Laboratories, Dept of Chemistry and Applied Chemistry, University of Salford, Salford M5 4WT, Journal of the Chemical Society, Perkin Transactions 1, 1980, p. 1370.

International Search Report for PCT/US2007/074076 mailed Feb. 6, 2008.

International Search Report for PCT/US2007/078341 mailed Jan. 31, 2008.

Krutosikova, A. et al., "Furan derivatives. LV. Preparation of 5-aryl-2-furfuryl phenyl and 5-aryl-2-furfuryl 4-tolyl sulfones". Chemick Zvesti—Chemical Papers, Veda Bratislava, SK. vol. 28, Jan. 1, 1974, pp. 414-417, ISSN: 0366-6352, p. 414, compounds I-IX.

Lambeng, N. et al., "Discovery of a Novel Piperidinyl-Sulfonyl Benzoic Ester, Active as CB1 Agonist" Poster. 231st ACS National Meeting, Atlanta, GA. Mar. 26-30, 2006.

Messinger, P., "Sulfones via Mannich bases" Archiv der Pharmazie, 1973, vol. 306, No. 8, pp. 603-610, ISSN: 0365-6233. p. 607, compounds 28A-29C.

Office Action from the EPO dated Mar. 22, 2010.

Schaefer, H. et al. "On the Synthesis of 4-aminoquinolines and -quinolinones-(2) from Anthranilonitrile" Chemistry Department of the Technical University of Dresden, Journal for Practical Chemistry, vol. 321, No. 4, 1979, pp. 695-698.

Seidel M. C. et al., "Reaction of Substituted 2-carbethoxyacetylaminopyridines and similar compounds with triethyl orthoformate and zinc chloride". Rohm and Haas Company, Spring House, Pennsylvania 19477, 1989.

Sisko, J. et al., "An investigation of imidazole and oxazole synthesis using aryl-substituted TosMIC reagents". The Journal of Organic Chemistry, vol. 65, No. 5, Mar. 10, 2000, pp. 1516-1624, ISSN: 022-3263, p. 1523, table 5, compound 69.

Strating, J., et al. "Nucleophilic Additions to Bis-Tertiobutyl Sulfonyl Acetylene (Properties of the sulfonyl group XLIV 1)". University of Groningue, Organic Chemistry Laboratory, 1954, pp. 709-716.

Tegley, et al., "Discovery of Novel Hydroxy-Thiazoles as HIF-alpha Prolyl Hydroxylase Inhibitors: SAR, Synthesis, and Modeling Evaluation," Bioorganic & Medicinal Chemistry Letters, Pergamon, Elsevier Science, GB, vol. 18, No. 14, 2008, pp. 3925-3928.

Troeger, J. et al., "Regarding sulfonated Butyric Acids". From the Laboratory for Pharmaceutical and Synthetic Chemistry of the Braunschweig Institute of Technology.1991, 40, 506.

Troeger, J. and Uhde, R., "Ueber sulfonirte buttersauren", J. Prakt. Chem., 1899, 1991, vol. 59, p. 320.

Wang, Y. et al., "Rapid and efficient synthesis of 1,2,4-oxadiazoles utilizing polymer-supported reagents under microwave heating". Organic Letters, vol. 7, No. 5, Mar. 3, 2005, pp. 925-928, ISSN: 1523-7060, p. 927, compounds 14,15.

Yokoyama, M. et al., "A regioselective synthesis of 3 5 disubstituted isoxazoles". Journal of the Chemical Society Perkin Transactions I, No. 1, 1986, pp. 67-72, ISSN: 0300-922X, pp. 68,69, compounds 6A, 14A.

* cited by examiner

COMPOUNDS WHICH MODULATE THE CB2 RECEPTOR

APPLICATION DATA

This application claims benefit to U.S. provisional application Ser. No. 60/826,819 filed Sep. 25, 2006.

BACKGROUND OF THE INVENTION

1. Technical Field

The present invention relates to novel compounds which modulate the CB2 receptor and their use as medicaments.

2. Background Information

Cannabinoids are a group of about 60 distinct compounds found in *Cannabis sativa* (also know as marijuana) with cannabinol, cannabidiol and $\Delta^9$-tetrahydrocannabinol (THC) being the most representative molecules. The therapeutic usage of *Cannabis* can be dated back to ancient dynasties of China and includes applications for various illnesses ranging from lack of appetite, emesis, cramps, menstrual pain, spasticity to rheumatism. The long history of *Cannabis* use has led to the development of several pharmaceutical drugs. For example, Marinol and Cesamet which are based on THC and its analogous nabilone, respectively, are used as anti-emetic and appetite stimulant. Despite of the clinical benefits, the therapeutic usage of *cannabis* is limited by its psychoactive effects including hallucination, addiction and dependence. Mechoulam R, ed. *Cannabinoids as Therapeutic Agents*, Boca Raton, Fla.; CRC Press, 1986 provides a review of the medicinal use of *cannabis*.

The physiological effects of cannabinoids are mediated by at least two G-protein coupled receptors, CB1 and CB2. Autoradiographic studies have demonstrated that CB1 receptors are expressed primarily in the central nervous system, specifically in the cerebral cortex, hippocampus, basal ganglia and cerebellum. They are also found to a lesser degree in the reproductive system and other peripheral tissues including that of the immune system. CB1 receptors regulate the release of neurotransmitters from the pre-synaptic neurons and are believed to mediate most of the euphoric and other central nervous system effects of *cannabis*, such as THC-induced ring-catalepsy, hypomobility, and hypothermia, which were found to be completely absent in mice with a deletion of the CB1 gene (Zimmer et al., Increased mortality, hypoactivity, and hypoalgesia in cannabinoid CB1 receptor knockout mice. Proc Natl Acad Sci USA. (1999) 96:5780-5785.)

CB2 receptors are almost exclusively found in the immune system, with the greatest density in the spleen. It is estimated that the expression level of CB2 in the immune cells is about 10 to 100 times higher than CB1. Within the immune system, CB2 is found in various cell types, including B cells, NK cells, monocytes, microglial cells, neutrophils, T cells, dentritic cells and mast cells, suggesting that a wide range of immune functions can be regulated through CB2 modulators (Klein et al., The cannabinoid system and immune system. J Leukoc Biol (2003) 74:486-496). This is supported by the finding that the immunomodulatory effect of THC is absent in CB2 deficient mice mice (Bicklet et al., Immunomodulation by cannabinoid is absent in mice deficient for the cannabinoid CB2 receptor. Eur J Pharmacol (2000) 396:141-149). CB2 selective ligands have been developed and tested for their effects in various inflammatory settings. For example, in animal models of inflammation, CB2 selective agonists, inverse agonists and antagonists have been shown to be effective in suppressing inflammation (Hanus et al., HU-308: a specific agonist for CB(2), a peripheral cannabinoid receptor. Proc Natl Acad Sci USA. (1999) 96:14228-14233, Ueda et al., Involvement of cannabinoid CB(2) receptor-mediated response and efficacy of cannabinoid CB(2) receptor inverse agonist, JTE-907, in cutaneous inflammation in mice. Eur J Pharmacol. (2005) 520:164-171 and Smith et al., The anti-inflammatory activities of cannabinoid receptor ligands in mouse peritonitis models Eur J Pharmacol. (2001) 432:107-119). Furthermore, CB2 selective agonists inhibit disease severity and spasticity in animal models for multiple sclerosis (Baker et al., Cannabinoids control spasticity and tremor in a multiple sclerosis model. Nature (2000) 404:84-87. Arevalo-Martin et al., Therapeutic action of cannabinoids in a murine model of multiple sclerosis J Neurosci. (2003) 23:2511-2516). Taken together, these results support the notion that CB2 receptor modulators can be employed for the treatment of medical conditions having an inflammatory component.

In addition to inflammation, CB2 agonists have been shown to inhibit pain and emesis. For instance, CB2 selective agonists blunt the pain response induced by thermal or other stimuli (Malan et al., CB2 cannabinoid receptor-mediated peripheral antinociception. Pain. (2001) 93:239-45 and Nackley et al., Selective activation of cannabinoid CB(2) receptors suppresses spinal fos protein expression and pain behavior in a rat model of inflammation. Neuroscience (2003) 119:747-57.) CB2 activation has also been demonstrated to inhibit neuropathic pain response (Ibrahim et al., Activation of CB2 cannabinoid receptors by AM1241 inhibits experimental neuropathic pain: pain inhibition by receptors not present in the CNS. Proc Natl Acad Sci USA. (2003) 100: 10529-33.) Finally, in contrast to the earlier data which did not find CB2 in the brain, a recent article demonstrated the expression of CB2 in the brain, at about 1.5% of the level in the spleen. CB2 activation is shown by this article to be responsible for the anti-emetic effect of endocannabinoid (Van Sickle et al., Identification and functional characterization of brainstem cannabinoid CB2 receptors. Science. 2005 310:329-332.) The foregoing results confirm that CB2 agonists can be used for the treatment of inflammatory and neuropathic pain as well as emesis.

BRIEF SUMMARY OF THE INVENTION

The present invention provides novel compounds which bind to and modulate the CB2 receptor. The invention also provides a method and pharmaceutical compositions for treating inflammation by way of the administration of therapeutic amounts of these compounds. Lastly, the invention provides a method and pharmaceutical compositions for treating pain by way of the administration of therapeutic amounts of the new compounds which are CB2 agonists.

DETAILED DESCRIPTION OF THE INVENTION

In its broadest generic aspect the invention provides compounds of the formula

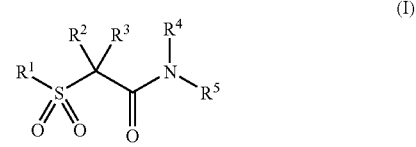

(I)

wherein:

$R^1$ is $C_{1-10}$ alkyl, $C_{1-10}$ alkoxy, $C_{3-10}$ cycloalkyl, 3-10 membered saturated heterocyclic ring, benzyl or phenethyl each optionally independently substituted with 1-3 substituents chosen from $C_{1-10}$ alkyl optionally substituted with 1 to 3 halogen atoms, $C_{3-10}$ cycloalkyl, 3-10 membered saturated heterocyclic ring optionally substituted with acyl, oxo or methyl sulfone, acyl, cyano, phenyl, oxo, hydroxyl and halogen;

$R^2$ and $R^3$ are independently hydrogen or $C_1$-$C_6$ alkyl; or $R^2$ and $R^3$ together with the carbon atom to which they are attached form a 3- to 6-membered cycloalkyl or heterocyclic ring;

$R^4$ is hydrogen or methyl;

$R^5$ is aryl or heteroaryl each optionally independently substituted with 1 to 3 substituents chosen from $C_1$-$C_6$ alkyl optionally substituted with 1 to 3 halogen atoms or with a heterocyclyl group, $C_1$-$C_6$ alkoxy optionally substituted with 1 to 3 halogen atoms, $C_3$-$C_6$ cycloalkyl, phenoxy, halogen, cyano, dimethylamino$C_1$-$C_4$alkyl, phenyl optionally substituted with 1 to 2 halogen atoms or $C_1$-$C_4$ alkyl optionally substituted with halogen, thienyl optionally substituted with 1 to 2 halogen atoms or $C_1$-$C_4$ alkyl optionally substituted with halogen and pyridinyl optionally substituted with 1 to 2 $C_1$-$C_4$ alkyl optionally substituted with halogen;

or a tautomer or pharmaceutically acceptable salt thereof.

In a first subgeneric aspect, the invention provides compounds of the formula I wherein, $R^1$ is methyl, ethyl, propyl, butyl, pentyl, hexyl, heptyl, octyl, nonyl, decyl, cyclopropyl, cyclobutyl, cyclopentyl, cyclohexyl, cycloheptyl, cyclooctyl, tetrahydropyranyl, bicylco(3.3.0)octanyl, bicyclo[4.3.0]nonyl, benzyl or phenethyl each optionally independently substituted with 1 to 3 substituents chosen from methyl, ethyl, cyclopropyl, cyclobutyl, cyclopentyl, cyclohexyl, tetrahydrofuranyl, tetrahydropyranyl, pyrrolidinyl (optionally substituted with acyl, oxo or methylsulfonyl), piperidinyl (optionally substituted with acyl, oxo or methylsulfone, acyl, cyano, phenyl, oxo, fluoro, chloro, bromo and hydroxyl;

$R^2$ and $R^3$ are independently hydrogen, methyl, ethyl, n-propyl, isopropyl, isobutyl, tert-butyl, or $R^2$ and $R^3$ together with the carbon to which they are attached form a cyclopropyl, cyclobutyl, cyclopentyl, cyclohexyl or tetrahydropyranyl ring;

$R^4$ is hydrogen;

$R^5$ is phenyl, naphthyl, pyridinyl, quinolinyl, isoquinolinyl, pyrrolyl, pyrazolyl, imidazolyl, oxazolyl, isoxazolyl, thiazolyl, isothiazolyl, triazolyl, oxadiazolyl, thiadiazolyl, indolyl, benzoxazolyl, benzopyrazolyl, benzoisoxazolyl, benzothiazolyl, benzoisothiazolyl, benzimidazolyl, tetrahydrobenzoxazolyl, tetrahydrobenzothiazolyl or tetrahydrobenzimidazolyl each optionally independently substituted with 1 to 3 substituents chosen from $C_1$-$C_6$ alkyl optionally substituted with 1 to 3 halogen atoms, $C_1$-$C_6$ alkoxy optionally substituted with 1 to 3 halogen atoms, $C_3$-$C_6$ cycloalkyl, phenoxy, halogen, cyano, dimethylamino$C_1$-$C_4$alkyl, phenyl optionally substituted with 1 to 2 halogen atoms or $C_1$-$C_4$ alkyl optionally substituted with halogen, thienyl optionally substituted with 1 to 2 halogen atoms or $C_1$-$C_4$ alkyl optionally substituted with halogen and pyridinyl optionally substituted with 1 to 2 $C_1$-$C_4$ alkyl optionally substituted with halogen.

In a further subgeneric aspect, the invention provides compounds of the formula I wherein, $R^1$ is methyl, ethyl, n-propyl, isopropyl, n-butyl, isobutyl, tert-butyl, n-pentyl, n-hexyl, n-heptyl, n-octyl, n-nonyl, n-decyl, cyclopropyl, cyclobutyl, cyclopentyl, cyclohexyl, cycloheptyl, cyclooctyl, tetrahydropyranyl, bicylco(3.3.0)octanyl, or bicyclo[4.3.0]nonyl each optionally independently substituted with 1 to 3 substituents chosen from methyl, ethyl, pivaloyl, cyclopropyl, cyclobutyl, cyclohexyl, tetrahydropyranyl, tetrahydrofuranyl, pyrrolidinyl optionally substituted with methylsulfone, fluoro, chloro, bromo, oxo and hydroxy;

$R^2$ and $R^3$ are independently hydrogen, methyl, ethyl, n-propyl, isopropyl, isobutyl, tert-butyl, or $R^2$ and $R^3$ together with the carbon to which they are attached form a cyclopropyl, cyclobutyl, cyclopentyl, cyclohexyl or tetrahydropyranyl ring;

$R^4$ is hydrogen;

$R^5$ is phenyl, naphthyl, pyridinyl, quinolinyl, isoquinolinyl, pyrrolyl, pyrazolyl, imidazolyl, oxazolyl, isoxazolyl, thiazolyl, isothiazolyl, triazolyl, oxadiazolyl, thiadiazolyl, indolyl, benzoxazolyl, benzopyrazolyl, benzoisoxazolyl, benzothiazolyl, benzoisothiazolyl, benzimidazolyl, tetrahydrobenzoxazolyl, tetrahydrobenzothiazolyl, or tetrahydrobenzimidazolyl each optionally independently substituted with 1 to 3 substituents chosen from $C_1$-$C_6$ alkyl optionally substituted with 1 to 3 halogen atoms, $C_1$-$C_6$ alkoxy optionally substituted with 1 to 3 halogen atoms, $C_3$-$C_6$ cycloalkyl, phenoxy, halogen, cyano, dimethylamino$C_1$-$C_4$alkyl, phenyl optionally substituted with 1 to 2 halogen atoms or $C_1$-$C_4$ alkyl optionally substituted with halogen, thienyl optionally substituted with 1 to 2 halogen atoms or $C_1$-$C_4$ alkyl optionally substituted with halogen and pyridinyl optionally substituted with 1 to 2 $C_1$-$C_4$ alkyl optionally substituted with halogen.

In another subgeneric aspect, the invention provides compounds of the formula I wherein, $R^1$ is benzyl or phenethyl each optionally independently substituted with 1 to 3 substituents chosen from methyl, fluoro, chloro and bromo.

In another subgeneric aspect, the invention provides compounds of the formula I wherein, $R^1$ is methyl, ethyl, n-propyl, isopropyl, tert-butyl, n-butyl, cyclopropyl, cyclopentyl, cyclohexyl, cycloheptyl, tetrahydropyranyl or benzyl each optionally substituted with methyl, pivaloyl, cyclopropyl, cyclobutyl, cyclohexyl tetrahydropyranyl, tetrahydrofuranyl, pyrrolidinyl optionally substituted with methylsulfonyl or chloro;

$R^2$ and $R^3$ are independently hydrogen, methyl, isopropyl, tert-butyl, or $R^2$ and $R^3$ together with the carbon to which they are attached form a cyclopropyl or cyclobutyl, ring;

$R^4$ is hydrogen;

$R^5$ is phenyl, pyridinyl, quinolinyl, isoquinolinyl, pyrazolyl, isoxazolyl, benzothiazolyl, thiadiazolyl, or thiazolyl each optionally independently substituted with 1 to 2 substituents chosen from, methyl, ethyl, tert-butyl, neopentyl, cyclohexyl, trifluoromethyl or phenyl optionally substituted with a chlorine atom.

The term "alkyl", or any substituent containing an alkyl group such as alkoxy or acylamino, shall be understood to be branched or unbranched alkyl groups, preferably $C_1$-$C_6$ and shall be understood to be optionally partially or fully halogenated.

The compounds of formula I may be made using the general synthetic methods described below, which also constitute part of the invention.

General Synthetic Methods

The invention also provides processes for making compounds of Formula (I). In all methods, unless specified otherwise, $R^1$, $R^2$, $R^3$, $R^4$ and $R^5$ in the formulas below shall have the meaning of $R^1$, $R^2$, $R^3$, $R^4$ and $R^5$ in Formula (I) of the invention described herein above. Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC), if desired, and intermediates and products may be purified by chromatography on silica gel and/or by recrystallization.

The examples which follow are illustrative and, as recognized by one skilled in the art, particular reagents or conditions could be modified as needed for individual compounds without undue experimentation. Starting materials and intermediates used, in the methods below, are either commercially available or easily prepared from commercially available materials by those skilled in the art.

Compounds of Formula (I) may be synthesized by the method illustrated in Method A

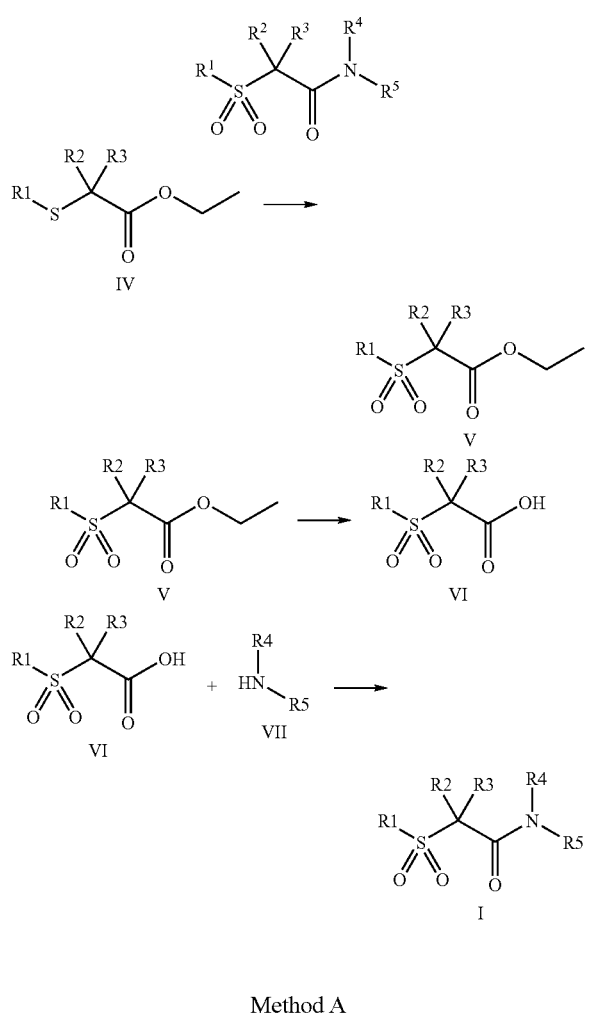

Method A

As illustrated in Method A, reaction of a thiol of formula II with a bromo ethyl ester of formula III, in a suitable solvent in the presence of a suitable base, provides a thioether of formula IV. Reacting the thioether of formula IV with a suitable oxidizing agent provides the corresponding sulfone of formula V. Hydrolysis of the ester group of sulfone of formula V in a suitable solvent in the presence of a suitable base such as lithium hydroxide, provides the corresponding acid of formula VI. Reacting the acid of formula VI with a reagent such as thionyl chloride or oxalyl chloride, provides the acid chloride which is then reacted with an amine of formula VII in a suitable solvent in the presence of a suitable base, to provide a compound of formula (I). Alternatively, the acid of formula VI may also be coupled with an amine of formula VII under standard coupling conditions, to provide a compound of formula (I). Standard peptide coupling reactions known in the art (see for example M. Bodanszky, 1984, The Practice of Peptide Synthesis, Springer-Verlag) may be employed in these syntheses. An example of suitable coupling conditions is treatment of a solution of the carboxylic acid in a suitable solvent such as DMF with EDC, HOBT, and a base such as diisopropylethylamine, followed by the desired amine. Further modification of the initial product of formula (I) by methods known in the art and illustrated in the Examples below, may be used to prepare additional compounds of this invention.

Compounds of Formula (I) may also be synthesized by the method illustrated in Method B

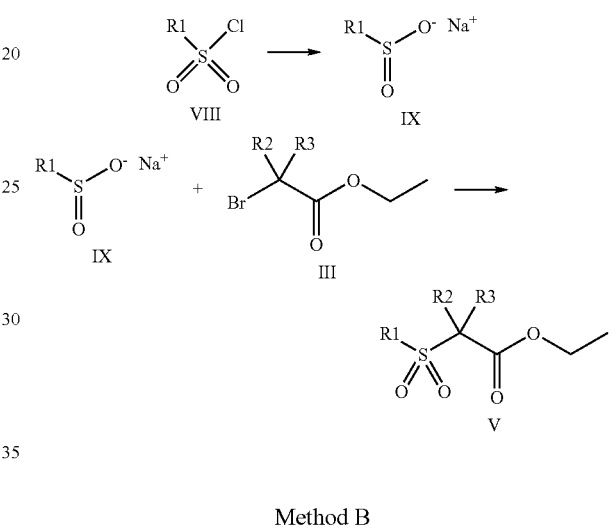

Method B

As shown in Method B, sulfonyl chloride of formula VIII is converted to the corresponding sulfinic acid sodium salt of formula IX, using procedures reported in the literature. Reaction of the sulfone of formula IX with a bromo ethyl ester of formula III in a suitable solvent, provides a sulfone of formula V. The sulfone of formula V is subjected to the sequence of reactions as shown in Method A, to provide a compound of formula (I).

Compounds of Formula (I) may be synthesized by the method illustrated in Method C

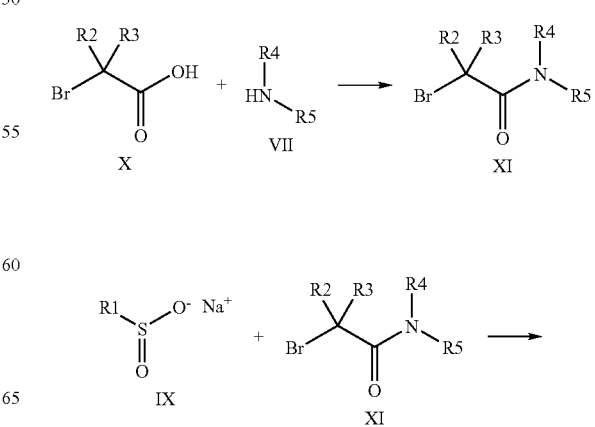

-continued

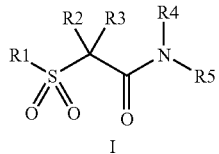

I

Method C

As illustrated in Method C, reacting the acid of formula X with a reagent such as thionyl chloride or oxalyl chloride, provides the acid chloride which is then reacted with an amine of formula VII in a suitable solvent in the presence of a suitable base, to provide a compound of formula (XI). Alternatively, the acid of formula X may also be coupled with an amine of formula VII under standard coupling conditions, to provide a compound of formula (XI). Reaction of the amide of formula XI with a sulfinic acid sodium salt of formula IX, in a suitable solvent in the presence of a suitable base, provides a compound of formula (I).

Compounds of Formula (I) may be synthesized by the method illustrated in Method D

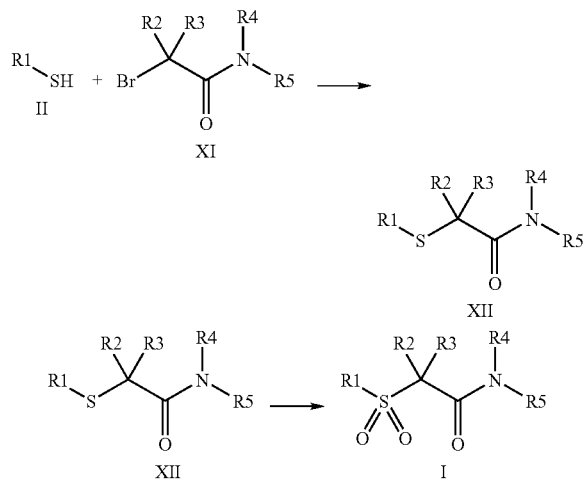

Method D

As illustrated in Method A, reaction of a thiol of formula II with a bromo amide of formula XI, in a suitable solvent in the presence of a suitable base, provides a thioether of formula XII. Reacting the thioether of formula XII with a suitable oxidizing agent in a suitable solvent, provides a compound of formula (I).

Compounds of Formula (I) may be synthesized by the method illustrated in Method E

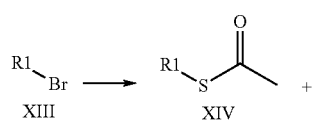

-continued

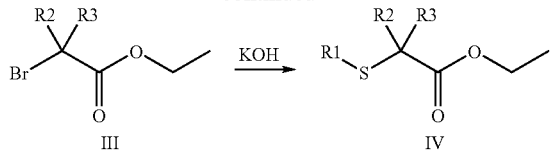

Method E

Reaction of the starting bromide of formula XIII with a reagent such as potassium thioacetate, in a suitable solvent, provides a thioacetic acid ester of formula XIV. Reaction of the thioacetic acid ester XIV with the bromo ethyl ester of formula III, in a suitable solvent in the presence of a suitable base, provides the corresponding sulfanyl acid ethyl ester of formula IV which may be converted to a compound of formula (I) by the sequence of steps shown in Method A.

Compounds of Formula (I) may be synthesized by the method illustrated in Method F

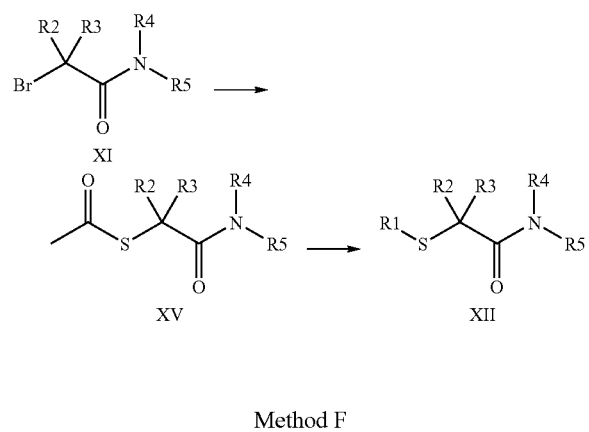

Method F

Reaction of a bromoamide of formula XI with a reagent such as potassium thioacetate, in a suitable solvent provides a thio compound of formula XV. Reaction of the thio compound of formula XV with the appropriate bromo compound, in a suitable solvent, in the presence of a suitable base provides the thio amide of formula XII which may be converted to a compound of formula (I) as in Method D.

Compounds of Formula (I) may be synthesized by the method outlined in Method G.

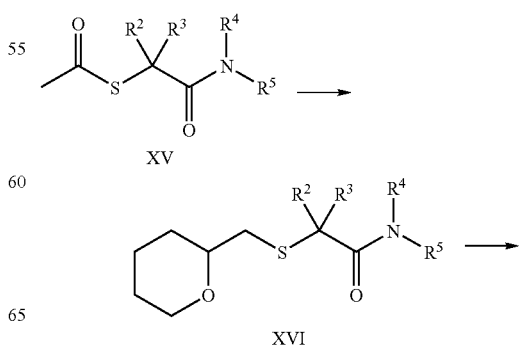

-continued

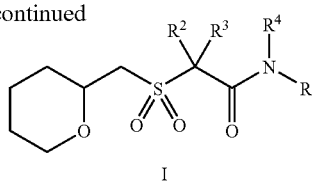

I

Method G

Reaction of an acylated thio-compound of formula XV with bromomethyltetra-hydropyran, in the presence of a suitable base, such as sodium methoxide, in a suitable solvent, provides an intermediate of formula XVI. Reaction of the intermediate of formula XVI with a suitable oxidizing agent such as hydrogen peroxide provides a compound of formula I.

Compounds of Formula (I) may be synthesized by the method shown in Method H.

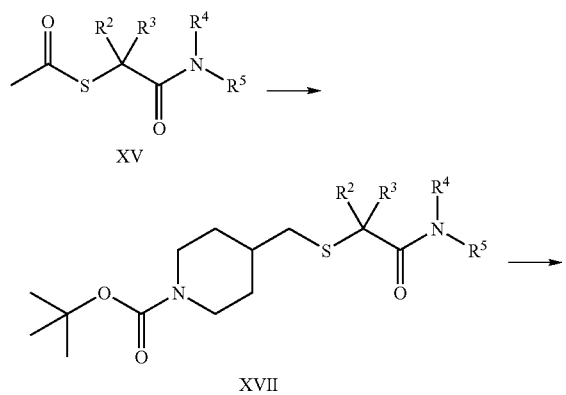

Method H

As illustrated above, reaction of an acylated thio-compound of formula XV with N-Boc-bromomethylpiperidine, in the presence of a suitable base, such as sodium methoxide, in a suitable solvent, provides an intermediate of formula XVII. Removal of the protecting group in the presence of an acid, and oxidation under standard reaction conditions, provides a compound of formula I.

Compounds of Formula (I) may be synthesized by the method shown in Method I.

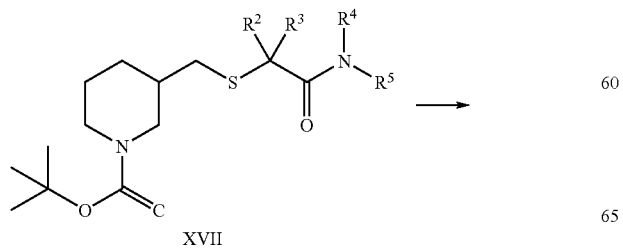

-continued

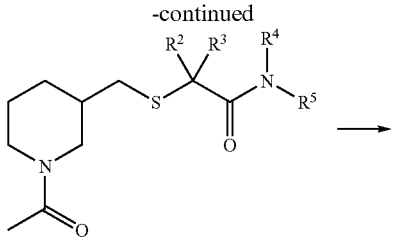

XVIII

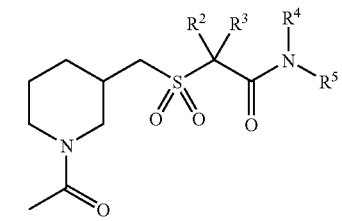

I

Method I

As outlined above, deprotection of a N-Boc protected piperidine of formula XVII, with a suitable acid followed by acylation with a reagent such as acetic anhydride, in the presence of a suitable base, provides a compound of formula XVIII. Reaction of the intermediate of formula XVIII with a suitable oxidizing agent such as m-chloroperbenzoic acid, provides a compound of formula I.

Compounds of Formula (I) may be synthesized by the method illustrated in Method J.

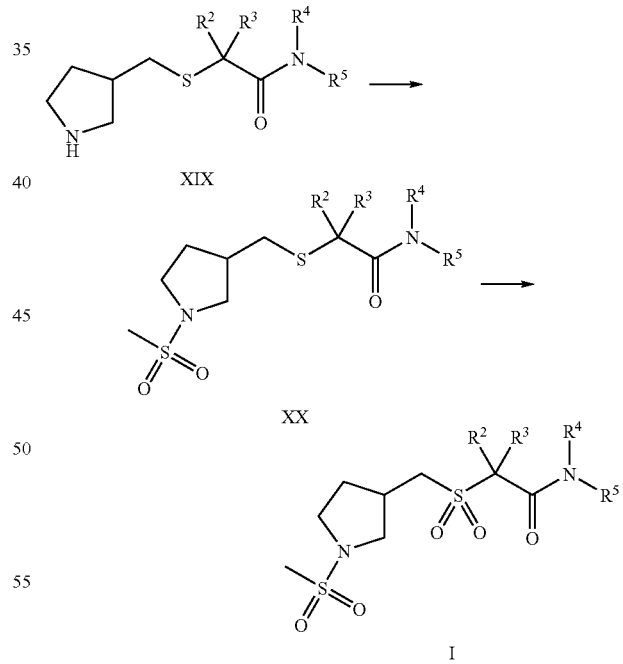

Method J

As outlined in the above method J, reaction of a compound of formula XIX with methane sulfonyl chloride, in the presence of a suitable base, in a suitable solvent, provides an intermediate of formula XX. Reaction of the intermediate of formula XX with a suitable oxidizing agent such as m-chloroperbenzoic acid, provides a compound of formula I.

Compounds of Formula (I) may be synthesized by the method illustrated in Method K.

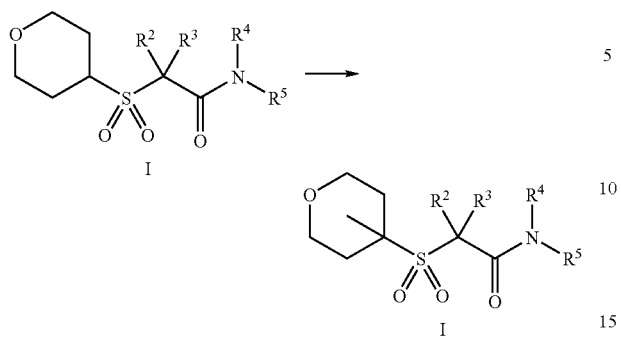

Method K

A compound of formula I may be converted to another compound of formula I as shown in method K. Alkylation of a compound of formula I with a reagent such as methyl iodide, in the presence of a suitable base such as lithium diisopropylamide, provides a methylated compound of formula 1.

EXAMPLES

The manner in which the compounds of the invention can be made will be further understood by way of the following Examples.
Experimental Procedures for Compounds of Formula I

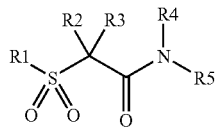

Method A

Synthesis of N-(5-tert-Butyl-isoxazol-3-yl)-2-cyclohexanesulfonyl-2-methyl-propionamide Example 1 in Table 17

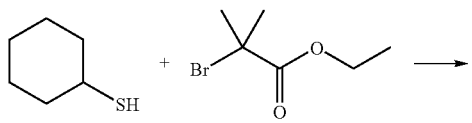

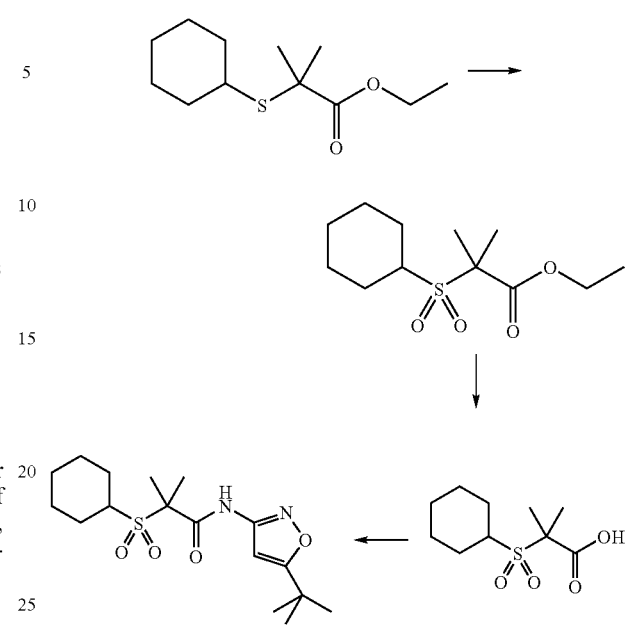

Step 1: Synthesis of
2-Cyclohexylsulfanyl-2-methyl-propionic acid ethyl ester

Prepared as described by adaptation of the following reference: Brown et al. *J. Med. Chem.* 1999, 42, 3785-3788

To a solution of 2.5 g (21.5 mmol) of cyclohexyl thiol in ethanol (75 mL) were added 1.2 g (21.5 mmol) of KOH pellets, followed by 4.2 g (21.5 mmol) of ethyl α-bromoisobutyrate. The reaction was heated to reflux for 18 h and then cooled to room temperature. The solid (KBr) was separated by filtration and rinsed with ethanol (20 mL). The filtrate was concentrated under reduced pressure and the residue dissolved in DCM (50 mL). The organic layer was washed with water (2×20 mL). The aqueous washes were back-extracted with DCM (10 mL). The combined organics were washed with brine, dried over $Na_2SO_4$. Filtration and concentration under reduced pressure afforded 4.15 g of 2-cyclohexylsulfanyl-2-methyl-propionic acid ethyl ester.

According to this procedure the following thioethers were synthesized:

TABLE 1

| MOLSTRUCTURE | NAME | YIELD [%] | m/z [M + H⁺] |
|---|---|---|---|
|  | 2-Cyclohexylsulfanyl-2-methyl-propionic acid ethyl ester | 84 | 231 |

TABLE 1-continued

| MOLSTRUCTURE | NAME | YIELD [%] | m/z [M + H⁺] |
|---|---|---|---|
| | 2-Isopropylsulfanyl-2-methyl-propionic acid ethyl ester | 83 | 191 |
| | 1-Cyclohexylsulfanyl-cyclobutanecarboxylic acid ethyl ester | 68 | 243 |
| | 2-Cyclopentylsulfanyl-2-methyl-propionic acid ethyl ester | 77 | 217 |
| | 2-(4-Chloro-benzylsulfanyl)-2-methyl-propionic acid | 40* | 245/247 |
| | 2-tert-Butylsulfanyl-2-methyl-propionic acid ethyl ester | 88 | 205 |
| | 2-Isopropylsulfanyl-propionic acid ethyl ester | 50 | 177 |
| | 2-Isopropylsulfanyl-3-methyl-butyric acid ethyl ester | 45 | structure confirmed by 1H NMR |
| | 2-sec-Butylsulfanyl-2-methyl-propionic acid ethyl ester | 55 | 205 |
| | 2-Ethylsulfanyl-2-methyl-propionic acid ethyl ester | 44 | 177 |

*hydrolysis of the ethyl ester occurred during reaction conditions

Step 2: Synthesis of 2-Cyclohexanesulfonyl-2-methyl-propionic acid ethyl ester Prepared as described by adaptation of the following reference:

Aranapakam, V. et al. *J. Med. Chem.*, 2004, 47, 6255-6269.

To a solution of 4.15 g (18 mmol) of 2-cyclohexylsulfanyl-2-methyl-propionic acid ethyl ester in dioxane/water (5/1, 40 mL) were added in one portion 33.2 g (54 mmol) of potassium monopersulfate triple salt (OXONE®). The white suspension was stirred at room temperature for 18 h. The white solid was separated by filtration and washed with dioxane (10 mL). The filtrate was concentrated under reduced pressure to remove the organic solvent. The resulting aqueous solution was extracted with DCM (3×40 mL). The combined organic extracts were washed with brine, dried over Na₂SO₄ and filtered. The filtrate was concentrated under reduced pressure to afford 3.47 g of 2-cyclohexanesulfonyl-2-methyl-propionic acid ethyl ester.

According to this procedure the following sulfones were synthesized:

TABLE 2

| MOLSTRUCTURE | NAME | YIELD [%] | m/z [M + H$^+$] |
|---|---|---|---|
| | 2-Cyclohexanesulfonyl-2-methyl-propionic acid ethyl ester | 50 | 263 |
| | 2-Methyl-2-(propane-2-sulfonyl)-propionic acid ethyl ester | 75 | 223 |
| | 1-Cyclohexanesulfonyl-cyclobutanecarboxylic acid ethyl ester | 76 | 275 |
| | 2-Cyclopentanesulfonyl-2-methyl-propionic acid ethyl ester | 78 | 249 |
| | 2-(4-Chloro-phenylmethanesulfonyl)-2-methyl-propionic acid | 81* | 277/279, 294/296 [M + H$_2$O$^+$] |
| | 2-Methyl-2-(2-methyl-propane-2-sulfonyl)-propionic acid ethyl ester | 86 | 237 |
| | 2-(Propane-2-sulfonyl)-propionic acid ethyl ester | 99 | 209 |
| | 3-Methyl-2-(propane-2-sulfonyl)-butyric acid ethyl ester | 100 | 237 |
| | 2-(Butane-2-sulfonyl)-2-methyl-propionic acid ethyl ester | 77 | 237 |
| | 2-Ethanesulfonyl-2-methyl-propionic acid ethyl ester | 85 | 209 |

*2-(4-Chloro-benzylsulfanyl)-2-methy-propionic acid used for oxidation step

Step 3: Synthesis of 2-Cyclohexanesulfonyl-2-methyl-propionic acid

Prepared as described by adaptation of the following reference:
Troeger, Uhde., *J. Prakt. Chem.* 1899, 59, 320-349

To a solution of 3.47 g (13.2 mmol) of 2-cyclohexanesulfonyl-2-methyl-propionic acid ethyl ester in THF/water (4/1, 50 mL) were added 1.11 g (26.4 mmol) of lithium hydroxide monohydrate. The reaction was stirred at room temperature for 18 h. The reaction was further diluted with water (20 mL) and then washed with DCM (2×15 mL). The basic aqueous layer was cooled in an ice bath and then acidified with 1M aqueous HCl solution to pH 2. The acidic aqueous layer was extracted with DCM (3×20 mL). The combined organic extracts were washed with brine, dried over $Na_2SO_4$ and filtered. Concentration of the filtrate under reduced pressure afforded 2.96 g of 2-cyclohexanesulfonyl-2-methyl-propionic acid.

According to this procedure the following acids were synthesized:

TABLE 3

| MOLSTRUCTURE | NAME | YIELD [%] | m/z [M + H$^+$] |
|---|---|---|---|
|  | 2-Cyclohexanesulfonyl-2-methyl-propionic acid | 64 | 258 [M + Na$^+$ + H$^+$] |
|  | 2-Methyl-2-(propane-2-sulfonyl)-propionic acid | 92 | 195, 212 [M + H$_2$O$^+$] |
|  | 1-Cyclohexanesulfonyl-cyclobutanecarboxylic acid | 89 | 247 |
|  | 2-Cyclopentanesulfonyl-2-methyl-propionic acid | 92 | 221 |
|  | 2-Methyl-2-(2-methyl-propane-2-sulfonyl)-propionic acid | 69 | 209, 226 [M + H$_2$O$^+$] |
|  | 2-(Propane-2-sulfonyl)-propionic acid | 29 | 181 |
|  | 3-Methyl-2-(propane-2-sulfonyl)-butyric acid | 32 | 209 |
|  | 2-(Butane-2-sulfonyl)-2-methyl-propionic acid | 78 | 209, 226 [M + H$_2$O$^+$] |

TABLE 3-continued

| MOLSTRUCTURE | NAME | YIELD [%] | m/z [M + H+] |
|---|---|---|---|
| | 2-Ethanesulfonyl-2-methyl-propionic acid | 89 | 198 [M + H₂O+] |

Step 4: Synthesis of N-(5-tert-Butyl-isoxazol-3-yl)-2-cyclohexanesulfonyl-2-methyl-propionamide Activation of 100 mg (0.4 mmol) of 2-cyclohexanesulfonyl-2-methyl-propionic acid as the corresponding acid chloride was achieved by treatment with thionyl chloride (1 mL) at 80° C. for 2 h. The reaction was cooled to room temperature and excess thionyl chloride was removed under reduced pressure.

The crude acid chloride was dissolved in DCM (0.5 mL) and added to a solution of 67 mg (0.48 mmol) of 3-amino-5-tert-butylisoxazole and N,N-diisopropylethylamine (83 mL, 0.48 mmol) in DCM (1 mL). The reaction was stirred at room temperature for 18 h, before it was evaporated to dryness. The reaction mixture was diluted with DCM (4 mL) and washed with saturated aqueous NaHCO₃ solution (3 mL). The organic layers was dried over Na₂SO₄, filtered and concentrated under reduced pressure. The crude product was purified by column chromatography (silica, eluent: DCM, 0-5% ethyl acetate) to afford 14 mg of N-(5-tert-butyl-isoxazol-3-yl)-2-cyclohexanesulfonyl-2-methyl-propionamide.

Examples listed in Table 17, Method A were made according to this procedure.

Method B

Synthesis of N-(4-tert-Butyl-thiazol-2-yl)-2-methanesulfonyl-2-methyl-propionamide Example 51 in Table 17

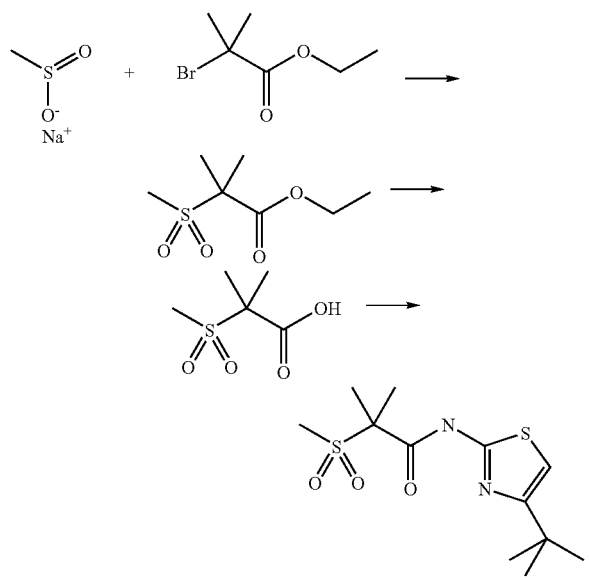

Step 1: Synthesis of 2-Methanesulfonyl-2-methyl-propionic acid ethyl ester

Prepared as described by adaptation of the following references:
Faucher, A.-M. et al. *J. Med. Chem.* 2004, 47, 19-21.
Binsiti, C. *Eur. J. Med. Chem. Chim. Ther.* 2001, 36, 809-828.
Field, L.; Clark, R. D. *Org. Synth.* 1958, 38, 62-64.
Troeger; U., *J. Prakt. Chem.* 1899, 59, 320-349.

To a suspension of 5 g (49 mmol) of sodium methane sulfite in DMF (50 mL) were added pyridine (6.3 mL) and ethyl α-bromoisobutyrate (2.9 mL). The reaction was stirred for 18 h at 50° C. under nitrogen. The reaction mixture was diluted with ethyl acetate (250 mL), washed with saturated aqueous NaHCO₃ (2×100 mL), 2M aqueous HCl solution (50 mL), brine (1×50 mL) and dried over Na₂SO₄. Filtration, concentration under reduced pressure afforded 3.04 g of 2-methanesulfonyl-2-methyl-propionic acid ethyl ester.

The compound did not ionise under LCMS conditions, thus the structure was confirmed by ¹H-NMR spectroscopy:
¹H NMR (360 MHz, CHLOROFORM-d) δ ppm 1.33 (3H, t, J=7.1 Hz), 1.66 (6H, s), 3.06 (3H, s), 4.28 (2H, q, J=7.1 Hz).

Step 2: Synthesis of 2-Methanesulfonyl-2-methyl-propionic acid

2-Methanesulfonyl-2-methyl-propionic acid was generally prepared as described in step 3, method A:

To a solution of 500 mg (2.6 mmol) of 2-methanesulfonyl-2-methyl-propionic acid ethyl ester in THF/water (4/1, 5 mL) were added 270 mg (6.6 mmol) of lithium hydroxide monohydrate. The reaction was stirred at room temperature for 18 h. The reaction was further diluted with water (20 mL) and then washed with DCM (2×15 mL). The basic aqueous layer was cooled in an ice bath and acidified with 1M aqueous HCl solution to pH 2. The acidic aqueous layer was extracted with isopropanol/chloroform (1/1, 3×20 mL). The combined organic extracts were washed with brine, dried over Na₂SO₄ and filtered. Concentration of the filtrate under reduced pressure afforded 413 mg of 2-methanesulfonyl-2-methyl-propionic acid. The compound did not ionise under LCMS conditions, thus the structure was confirmed by ¹H-NMR spectroscopy:
¹H NMR (400 MHz, DMSO-d₆) δ ppm 1.49 (6H, s), 3.08 (3H, s).

Step 3: Synthesis of N-(4-tert-butyl-thiazol-2-yl)-2-methanesulfonyl-2-methyl-propionamide Activation of 97 mg (0.6 mmol) of 2-methanesulfonyl-2-methyl-propionic acid as the corresponding acid chloride was achieved by treatment with thionyl chloride (2 mL) at 80° C. for 2 h. The reaction was cooled to room temperature and excess thionyl chloride was removed under reduced pressure.

The crude acid chloride was dissolved in DCM (2 mL) and added to a solution of 91 mg (0.6 mmol) of 2-amino-4-tert-butylthiazole and N,N-diisopropylethylamine (0.13 mL) in DCM (1 mL). The reaction was stirred at room temperature for 18 h. The reaction mixture was diluted with DCM, washed with saturated aqueous NaHCO₃ solution (2 mL), brine (2 mL) and dried over Na₂SO₄. Filtration and concentration of the filtrate afforded the crude product. Further purification by column chromatography (silica, eluent: heptanes, 0-20% ethyl acetate) yielded 116 mg of N-(4-tert-butyl-thiazol-2-yl)-2-methanesulfonyl-2-methyl-propionamide.

Examples listed in Table 17, Method B were made according to this procedure.

Method C

Synthesis of N-(5-tert-Butyl-isoxazol-3-yl)-2-methyl-2-(propane-1-sulfonyl)-propionamide Example 10 in Table 17

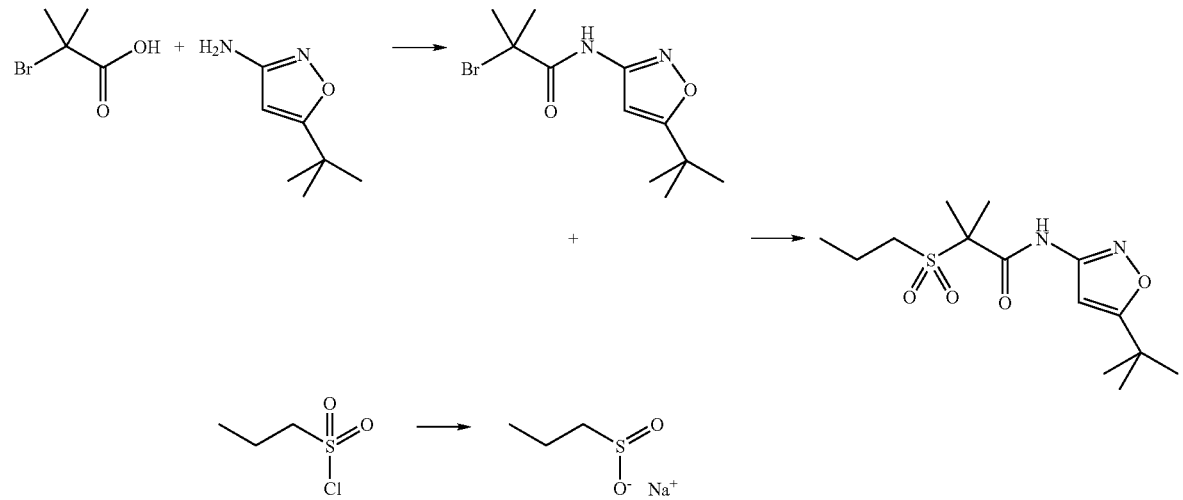

Step 1: Synthesis of 1-propanesulfinic acid sodium salt

Prepared as described by adaptation of the following references:
Faucher, A.-M. et al. *J. Med. Chem.* 2004, 47, 19-21.
Binsiti, C. Eur. *J. Med. Chem. Chim. Ther.* 2001, 36, 809-828.
Field, L.; Clark, R. D. *Org. Synth.* 1958, 38, 62-64.

To a solution of 0.26 g (3.2 mmol) of NaHCO₃ and 0.4 g (3.2 mmol) of Na₂SO₃ in water (1.5 mL) were added 0.23 g (1.6 mmol) of 1-propanesulfonyl chloride. The reaction was heated at 80° C. for 3 h. The solvent was removed under reduced pressure. The crude material was suspended in boiling ethanol (20 mL) and the inorganic solids were removed by filtration. The filtrate was concentrated under reduced pressure to afford 0.18 g of 1-propanesulfinic acid sodium salt.

Step 2: Synthesis of 2-Bromo-N-(5-tert-butyl-isoxazol-3-yl)-2-methyl-propionamide Prepared as described by adaptation of the following references: Katoh A. et al. *Heterocycles* 1999, 50, 299-308

Activation of 5 g (30 mmol) of 2-bromo-2-methylpropionic acid as the corresponding acid chloride was achieved by treatment with thionyl chloride (10 mL) at 60° C. for 2 h. The reaction was cooled and excess thionyl chloride was removed under reduced pressure to afford the corresponding acid chloride.

To a solution of 4.2 g (30 mmol) of 3-amino-5-tert-butyl-isoxazole and 5.2 mL (30 mmol) of N,N-diisopropylethylamine in DCM (20 mL) was added dropwise the acid chloride, as solution in DCM (15 mL). The reaction was stirred at room temperature for 18 h. The reaction mixture was washed with saturated aqueous NaHCO₃ solution (2×15 mL) and the layers were separated. The organic layer was further washed with brine, dried over MgSO₄, filtered and concentrated under reduced pressure. The crude was purified by dry flash column chromatography (silica, eluent DCM, 0-20% ethyl acetate) to yield 8.5 g of 2-bromo-N-(5-tert-butyl-isoxazol-3-yl)-2-methyl-propionamide.

According to this procedure the following amides were synthesized:

TABLE 4

| MOLSTRUCTURE | NAME | YIELD [%] | m/z [M + H⁺] |
|---|---|---|---|
|  | 2-Bromo-N-(5-tert-butyl-isoxazol-3-yl)-2-methyl-propionamide | 97 | 289/291 |

TABLE 4-continued

| MOLSTRUCTURE | NAME | YIELD [%] | m/z [M + H⁺] |
|---|---|---|---|
| | 2-Bromo-2-methyl-N-(5-trifluoro-methyl-pyridin-2-yl)-propionamide | 55 | 311/313 |
| | 2-Bromo-N-(5-tert-butyl-2-methyl-2H-pyrazol-3-yl)-2-methyl-propionamide | 51 | 302/304 |
| | 2-Bromo-2-methyl-N-(6-trifluoromethyl-pyridin-2-yl)-propionamide | 72 | 311/313 |
| | 2-Bromo-N-(3-tert-butyl-isoxazol-5-yl)-2-methyl-propionamide | 68 | 289/291 |

Step 3: Synthesis of N-(5-tert-Butyl-isoxazol-3-yl)-2-methyl-2-(propane-1-sulfonyl)-propionamide Prepared as described by adaptation of the following references:

Faucher, A.-M. et al. *J. Med. Chem.* 2004, 47, 19-21.
Troeger; Uhde; *J. Prakt. Chem.* 1899, 59, 320-349.
Binsiti, C. *Eur. J. Med. Chem. Chim. Ther.* 2001, 36, 809-828.
Field, L.; Clark, R. D. *Org. Synth.* 1958, 38, 62-64.

To a solution of 160 mg (0.55 mmol) of 2-bromo-N-(5-tert-butyl-isoxazol-3-yl)-2-methyl-propionamide in DMF (3 mL) were added 87 mg (0.71 mmol) of 1-propanesulfinic acid sodium salt in one portion. Pyridine (48 µL) was added and the reaction was stirred at 50° C. for 18 h. The mixture was acidified with 1M aqueous HCl solution (1 mL) and extracted with diethyl ether (3×3 mL). The combined organic layers were dried over Na₂SO₄ and filtered. The filtrate was concentrated under reduced pressure. The crude material was purified by column chromatography (silica, eluent heptanes, 0-20% ethyl acetate) to afford 86 mg of N-(5-tert-butyl-isoxazol-3-yl)-2-methyl-2-(propane-1-sulfonyl)-propionamide.

Examples listed in Table 17, Method C were made according to this procedure.

Method D

Synthesis of N-(5-tert-Butyl-isoxazol-3-yl)-2-methyl-2-(2-methyl-propane-1-sulfonyl)-propionamide Example 52 in Table 17

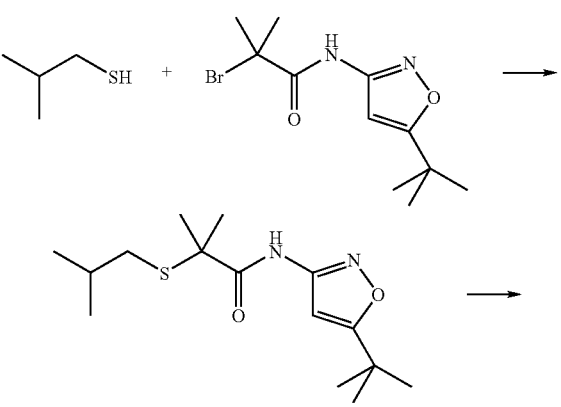

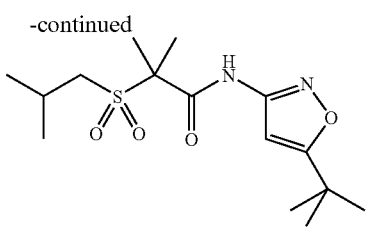

Step 1: Synthesis of N-(5-tert-Butyl-isoxazol-3-yl)-2-isobutylsulfanyl-2-methyl-propionamide To a stirred solution of 82 μL (1.31 mmol) of 2-methyl-1-propanethiol in ethanol (2 mL) were added 37 mg (0.65 mmol) of KOH pellets, followed by 190 mg (0.65 mmol) 2-bromo-N-(5-tert-butyl-isoxazol-3-yl)-2-methyl-propionamide (prepared as described in step 2, method B). The reaction mixture was heated to reflux for 18 h. The reaction was cooled to room temperature. The solid (KBr) was separated by filtration and rinsed with ethanol (15 mL). The filtrate was concentrated under reduced pressure to yield 160 mg of N-(5-tert-butyl-isoxazol-3-yl)-2-isobutylsulfanyl-2-methyl-propionamide.

According to this procedure the following amides were synthesized:

dioxane/water (5/1, 2.5 mL) were added in one portion 0.99 g (1.61 mmol) of potassium monopersulfate triple salt (OXONE®). The white suspension was stirred at room temperature for 18 h. The white solid was separated by filtration and washed with dioxane (5 mL). The filtrate was concentrated under reduced pressure to remove the organic solvent. The resulting aqueous solution was extracted with DCM (2×5 mL). The combined organic extracts were washed with saturated aqueous NaHCO₃ solution (5 mL), brine (5 mL), dried over Na₂SO₄ and filtered. The filtrate was concentrated under reduced pressure. The crude residue was purified by column chromatography (silica, eluent DCM, 0-10% ethyl acetate) to afford 98 mg of N-(5-tert-butyl-isoxazol-3-yl)-2-isobutylsulfonyl-2-methyl-propionamide.

Examples listed in Table 17, Method D were made according to this procedure.

Method E

Synthesis of N-(5-tert-Butyl-isoxazol-3-yl)-2-methyl-2-(tetrahydro-pyran-4-ylmethanesulfonyl)-propionamide Example 56, Table 17

TABLE 5

| MOLSTRUCTURE | NAME | YIELD [%] | m/z [M + H⁺] |
|---|---|---|---|
|  | N-(5-tert-Butyl-isoxazol-3-yl)-2-isobutylsulfanyl-2-methyl-propionamide | 83 | 299 |
|  | N-(3-tert-Butyl-isoxazol-5-yl)-2-(4-fluoro-benzylsulfanyl)-2-methyl-propionamide | 63 | 351 |

Step 2: Synthesis of N-(5-tert-Butyl-isoxazol-3-yl)-2-isobutylsulfonyl-2-methyl-propionamide To a solution of 160 mg (0.54 mmol) of N-(5-tert-butyl-isoxazol-3-yl)-2-isobutylsulfanyl-2-methyl-propionamide in

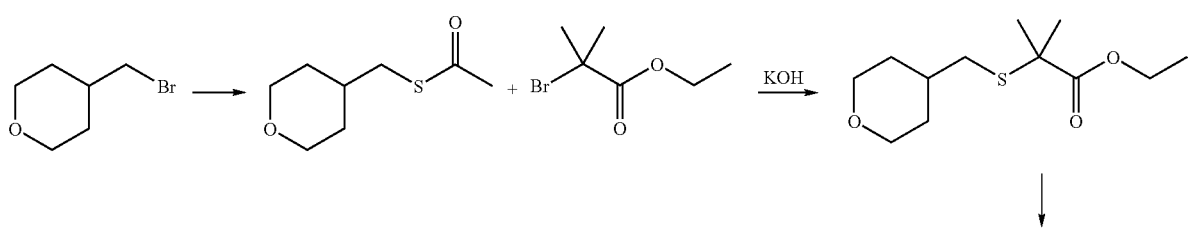

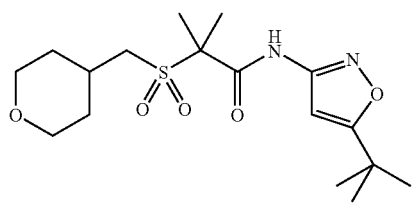 ← 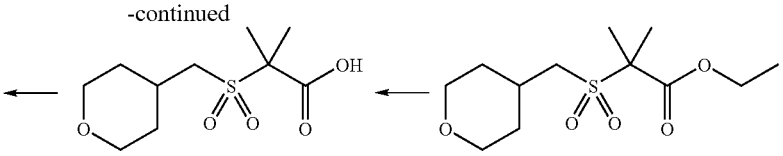

-continued

Step 1: Synthesis of Thioacetic acid S-(tetrahydro-pyran-4-ylmethyl) ester

Prepared as described by adaptation of the following literature reference:
Watson, R. J. et al. *Tetrahedron Lett.* 2002, 43, 683-685.

To a solution of 0.97 g (5.4 mmol) of 4-bromomethyl tetrahydropyran in DMF (9.7 mL) were added 1.27 g (11.2 mmol) of potassium thioacetate. The reaction was stirred at room temperature for 3 h. Diethyl ether (100 mL) was added and the reaction mixture was washed with saturated aqueous NaHCO₃ solution (2×25 mL) and brine (25 mL). The organic layer was dried over Na₂SO₄, filtered and concentrated under reduced pressure. The residue was purified by column chromatography (silica, eluent: heptanes, 10% ethyl acetate) to afford 0.81 g of thioacetic acid S-(tetrahydro-pyran-4-ylmethyl)ester.

According to this procedure the following thioacetates were synthesized:

0.81 g (4.66 mmol) of thioacetic acid S-(tetrahydro-pyran-4-ylmethyl)ester. The reaction was stirred at room temperature under nitrogen for 0.5 h. Then 2.1 mL (14.1 mmol) of ethyl α-bromoisobutyrate were added and the reaction stirred for 4 h. The resulting precipitate was removed by filtration and the filtrate concentrated under reduced pressure. The residue was dissolved in DCM (100 mL) and washed with saturated aqueous NaHCO₃ (50 mL), brine (50 mL) and dried over Na₂SO₄. Filtration and concentration of the filtrate under reduced pressure, followed by column chromatography of the residue (silica, eluent: heptanes, 0-20% ethyl acetate) afforded 0.76 g of 2-methyl-2-(tetrahydro-pyran-4-ylmethylsulfanyl)-propionic acid ethyl ester.

According to this procedure the following ethyl esters were synthesized:

TABLE 6

| MOLSTRUCTURE | NAME | YIELD [%] | m/z [M + H⁺] |
|---|---|---|---|
|  | Thioacetic acid S-(tetrahydro-pyran-4-ylmethyl) ester | 86 | 175 |
|  | Thioacetic acid S-(tetrahydro-pyran-4-yl) ester | 68 | 161 |

Step 2: Synthesis of 2-Methyl-2-(tetrahydro-pyran-4-ylmethylsulfanyl)-propionic acid ethyl ester A solution of 0.86 g (15.2 mmol) of potassium hydroxide in ethanol (78 mL, degassed and under nitrogen) was added to

TABLE 7

| MOLSTRUCTURE | NAME | YIELD [%] | m/z [M + H⁺] |
|---|---|---|---|
|  | 2-Methyl-2-(tetrahydro-pyran-4-ylmethylsulfanyl)-propionic acid ethyl ester | 66 | 247 |

TABLE 7-continued

| MOLSTRUCTURE | NAME | YIELD [%] | m/z [M + H+] |
|---|---|---|---|
|  | 2-Methyl-2-(tetrahydro-pyran-4-ylsulfanyl)-propionic acid ethyl ester | 75 | 233 |
|  | 1-(Tetrahydro-pyran-4-ylmethylsulfanyl)-cyclobutanecarboxylic acid ethyl ester | 77 | 259 |

Step 3: Synthesis of 2-Methyl-2-(tetrahydro-pyran-4-ylmethanesulfonyl)-propionic acid ethyl ester Prepared as described by adaptation of Method A, step 2.

To a solution of 0.76 g (3.1 mmol) of 2-methyl-2-(tetrahydro-pyran-4-ylmethylsulfanyl)-propionic acid ethyl ester in dioxane/water (1/1, 10 mL) was added in one portion 4.1 g (6.6 mmol) of potassium monopersulfate triple salt (OXONE®). The white suspension was stirred at room temperature for 1 h. The white solid was separated by filtration and washed with dioxane (5 mL). The filtrate was concentrated under reduced pressure to remove the organic solvent. The resulting mixture was diluted with DCM (50 mL) and water (5 mL). The organic layer was separated and washed with a saturated aqueous NaHCO$_3$/brine (1/1) mixture (20 mL) and dried over Na$_2$SO$_4$. Filtration and concentration under reduced pressure afforded 0.77 g of 2-methyl-2-(tetrahydro-pyran-4-ylmethanesulfonyl)-propionic acid ethyl ester.

According to this procedure the following sulfones were synthesized:

Step 4: Synthesis of 2-Methyl-2-(tetrahydro-pyran-4-ylmethanesulfonyl)-propionic acid Prepared as described by adaptation of Method A, step 3.

To a solution of 769 mg (2.77 mmol) of 2-methyl-2-(tetrahydro-pyran-4-ylmethanesulfonyl)-propionic acid ethyl ester in THF/water (1/1, 10 mL) were added 228 mg (5.43 mmol) of lithium hydroxide monohydrate. The reaction was stirred at room temperature for 18 h. The reaction was concentrated under reduced pressure. The residue was dissolved in water (10 mL) and washed with diethyl ether (2×25 mL). The aqueous layer was cooled in an ice bath and then acidified with 1M aqueous HCl solution to pH 2. The acidic aqueous layer was extracted with ethyl acetate (2×50 mL) and with isopropanol/chloroform (3×50 mL). The combined organic extracts were dried over Na$_2$SO$_4$ and filtered. Concentration of the filtrate under reduced pressure afforded 734 mg of 2-methyl-2-(tetrahydro-pyran-4-ylmethanesulfonyl)-propionic acid.

According to this procedure the following acids were synthesized:

TABLE 8

| MOLSTRUCTURE | NAME | YIELD [%] | m/z [M + H+] |
|---|---|---|---|
|  | 2-Methyl-2-(tetrahydro-pyran-4-ylmethanesulfonyl)-propionic acid ethyl ester | 90 | 279 |
|  | 2-Methyl-2-(tetrahydro-pyran-4-sulfonyl)-propionic acid ethyl ester | 84 | 265 |
|  | 1-(Tetrahydro-pyran-4-ylmethanesulfonyl)-cyclobutanecarboxylic acid ethyl ester | 60 | 291 |

TABLE 9

| MOLSTRUCTURE | NAME | YIELD [%] | m/z [M + H+] |
|---|---|---|---|
|  | 2-Methyl-2-(tetrahydro-pyran-4-ylmethanesulfonyl)-propionic acid | 100 | 251 |
|  | 2-Methyl-2-(tetrahydro-pyran-4-sulfonyl)-propionic acid | 93 | 237 |
|  | 1-(Tetrahydro-pyran-4-ylmethanesulfonyl)-cyclobutanecarboxylic acid | 80 | 263 |

Step 5: Synthesis of N-(5-tert-Butyl-isoxazol-3-yl)-2-methyl-2-(tetrahydro-pyran-4-ylmethanesulfonyl)-propionamide Prepared as described by adaptation of Method A, step 4.

Activation of 122 mg (0.49 mmol) of 2-methyl-2-(tetrahydro-pyran-4-ylmethanesulfonyl)-propionic acid as the corresponding acid chloride was achieved by treatment with thionyl chloride (0.4 mL) at 50° C. for 1 h. The reaction was cooled to room temperature and excess thionyl chloride was removed under reduced pressure.

The crude acid chloride was dissolved in DCM (2 mL) and added to a solution of 63 mg (0.49 mmol) of 3-amino-5-tert-butylisoxazole and N,N-diisopropylethylamine (145 mL, 0.88 mmol) in DCM (2 mL). The reaction was stirred at room temperature for 18 h. The reaction mixture was diluted with DCM (2 mL) and washed with a saturated aqueous NaHCO₃ solution/brine mixture (1/1, 2 mL). The organic layer was dried over Na₂SO₄, filtered and concentrated under reduced pressure. The crude product was purified by column chromatography (silica, eluent: heptanes, 0-20% ethyl acetate, then DCM, 0-20% ethyl acetate) to afford 41 mg of N-(5-tert-butyl-isoxazol-3-yl)-2-methyl-2-(tetrahydro-pyran-4-ylmethanesulfonyl)-propionamide.

Examples listed in Table 17, Method E were made according to this procedure.

Method F

Synthesis of N-(5-tert-Butyl-isoxazol-3-yl)-2-methyl-2-(tetrahydro-furan-4-ylmethanesulfonyl)-propionamide Example 74, Table 17

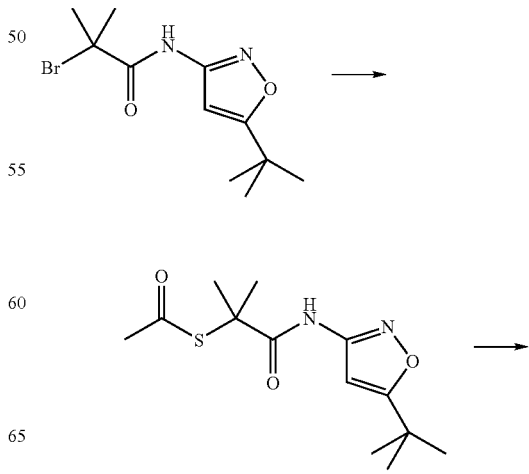

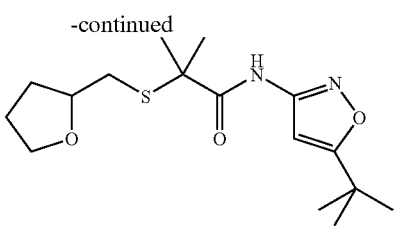

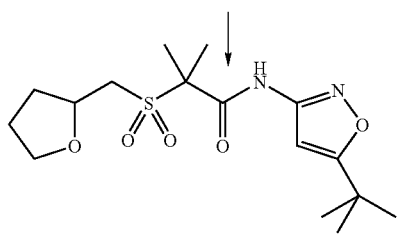

Step 1: Synthesis of Thioacetic acid S-[1-(5-tert-butyl-isoxazol-3-ylcarbamoyl)-1-methyl-ethyl]ester To a solution of 200 mg (0.69 mmol) of 2-bromo-N-(5-tert-butyl-isoxazol-3-yl)-2-methyl-propionamide (prepared as described in Method B, step 2) in DMF (3 mL) were added 157 mg (1.4 mmol) of potassium thioacetate. The reaction was stirred at room temperature for 3 h. The reaction mixture was diluted with diethyl ether (5 mL) and washed with 2M aqueous HCl solution (5 mL). The organic layer was dried over $Na_2SO_4$. Filtration and concentration under reduced pressure afforded 151 mg of thioacetic acid S-[1-(5-tert-butyl-isoxazol-3-ylcarbamoyl)-1-methyl-ethyl]ester.

According to this procedure the following thioacetates were synthesized:

TABLE 10

| MOLSTRUCTURE | NAME | YIELD [%] | m/z [M + H$^+$] |
|---|---|---|---|
|  | Thioacetic acid S-[1-(5-tert-butyl-isoxazol-3-ylcarbamoyl)-1-methyl-ethyl]ester | 76 | 285 |
|  | Thioacetic acid S-[1-(5-tert-butyl-2-methyl-2H-pyrazol-3-ylcarbamoyl)-1-methyl-ethyl]ester | 73 | 298 |
|  | Thioacetic acid S-[1-methyl-1-(5-trifluoromethyl-pyridin-2-ylcarbamoyl)-ethyl]ester | 62 | 307 |
|  | Thioacetic acid S-[1-(3-tert-butyl-isoxazol-5-ylcarbamoyl)-1-methyl-ethyl]ester | 62 | 285 |

Step 2: Synthesis of N-(5-tert-Butyl-isoxazol-3-yl)-2-methyl-2-(tetrahydro-furan-2-ylmethylsulfanyl)-propionamide To a solution of 100 mg (0.35 mmol) of thioacetic acid S-[1-(5-tert-butyl-isoxazol-3-ylcarbamoyl)-1-methyl-ethyl] ester in ethanol (2 mL) were added 70 mg (0.42 mmol) of 2-(bromomethyl)tetrahydrofuran and 340 μL (1.05 mmol) of sodium ethoxide solution (21% in ethanol) at room temperature. The reaction was heated to 50° C. for 18 h. The reaction mixture was concentrated under reduced pressure and the crude purified by column chromatography (silica, eluent: heptanes, 0-20% ethyl acetate) to afford 82 mg of N-(5-tert-butyl-isoxazol-3-yl)-2-methyl-2-(tetrahydro-furan-2-ylmethylsulfanyl)-propionamide.

According to this procedure the following thioethers were synthesized:

TABLE 11

| MOLSTRUCTURE | NAME | YIELD [%] | m/z [M + H⁺] |
|---|---|---|---|
|  | N-(5-tert-Butyl-isoxazol-3-yl)-2-methyl-2-(tetrahydro-furan-2-ylmethylsulfanyl)-propionamide | 71 | 327 |

Step 3: Synthesis of N-(5-tert-Butyl-isoxazol-3-yl)-2-methyl-2-(tetrahydro-pyran-4-ylmethanesulfonyl)-propionamide Prepared as described by adaptation of Method D, step 2.

To a solution of 82 mg (0.25 mmol) of N-(5-tert-butyl-isoxazol-3-yl)-2-methyl-2-(tetrahydro-furan-2-ylmethylsulfanyl)-propionamide in dioxane/water (5/1, 4 mL) were added in one portion 460 mg (0.75 mmol) of potassium monopersulfate triple salt (OXONE®). The white suspension was stirred at room temperature for 3 h. The white solid was separated by filtration and washed with dioxane (5 mL). The filtrate was concentrated under reduced pressure to remove the organic solvent. The resulting aqueous solution was extracted with DCM (2×5 mL). The combined organic extracts were washed with saturated aqueous NaHCO₃ solution (5 mL), brine (5 mL), dried over Na₂SO₄ and filtered. The filtrate was concentrated under reduced pressure. The crude residue was purified by column chromatography (silica, eluent: DCM, 0-10% ethyl acetate) to afford 5 mg of N-(5-tert-butyl-isoxazol-3-yl)-2-methyl-2-(tetrahydro-pyran-4-ylmethanesulfonyl)-propionamide.

Examples listed in Table 17, Method F were made according to this procedure.

Method G

Synthesis of N-(5-tert-Butyl-isoxazol-3-yl)-2-methyl-2-(tetrahydro-pyran-2-ylmethanesulfonyl)-propionamide

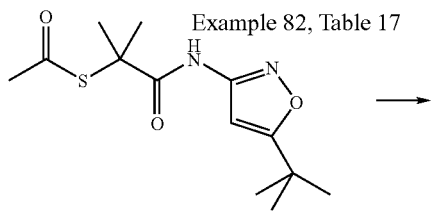

Example 82, Table 17

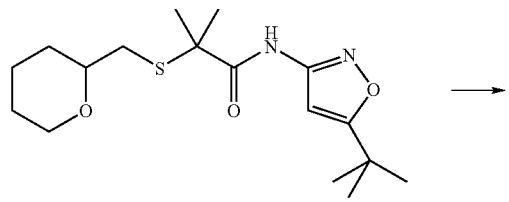

Step 1: Synthesis of N-(5-tert-Butyl-isoxazol-3-yl)-2-methyl-2-(tetrahydro-pyran-2-ylmethylsulfanyl)-propionamide To a solution of 100 mg (0.352 mmol) of thioacetic acid S-[1-(5-tert-butyl-isoxazol-3-ylcarbamoyl)-1-methyl-ethyl] ester (synthesized according to Method F, step 1) in ethanol (2 mL) were added 126 mg (0.704 mmol) of 2-(bromomethyl)tetrahydropyran and 76 mg (1.41 mmol) of sodium methoxide at room temperature. The reaction was heated to 130° C. for 0.5 h within a microwave (CEM Discover). The reaction mixture was concentrated under reduced pressure. The residue was dissolved in DCM (5 ml) and washed with saturated aqueous NaHCO₃ solution (5 ml). The organic phase was dried (Na₂SO₄), filtered and concentrated under reduced pressure to yield 119 mg of N-(5-tert-butyl-isoxazol-3-yl)-2-methyl-2-(tetrahydro-pyran-2-ylmethylsulfanyl)-propionamide.

According to this procedure the following thioethers were synthesized:

TABLE 12

| MOLSTRUCTURE | NAME | YIELD [%] | m/z [M + H⁺] |
|---|---|---|---|
| 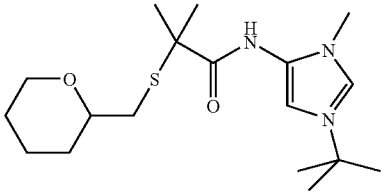 | N-(5-tert-Butyl-2-methyl-2H-pyrazol-3-yl)-2-methyl-2-(tetrahydro-pyran-2-ylmethylsulfanyl)-propionamide | 100 | 354 |
| 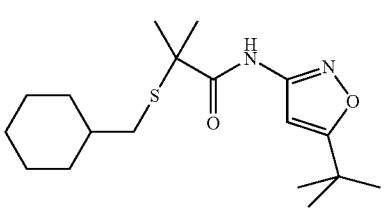 | N-(5-tert-Butyl-isoxazol-3-yl)-2-cyclohexylmethylsulfanyl-2-methyl-propionamide | 100 | 339 |
| 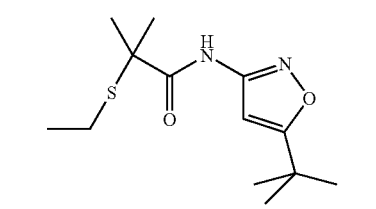 | N-(5-tert-Butyl-isoxazol-3-yl)-2-ethylsulfanyl-2-methyl-propionamide | 90 | 271 |
| 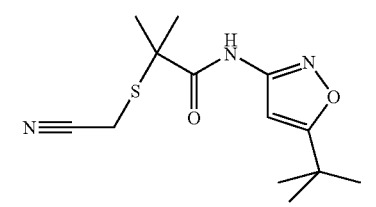 | N-(5-tert-Butyl-isoxazol-3-yl)-2-cyanomethylsulfanyl-2-methyl-propionamide | 96 | 282 |
| 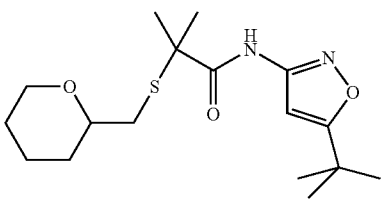 | N-(5-tert-Butyl-isoxazol-3-yl)-2-methyl-2-(tetrahydro-pyran-2-ylmethylsulfanyl)-propionamide | 100 | 341 |
| 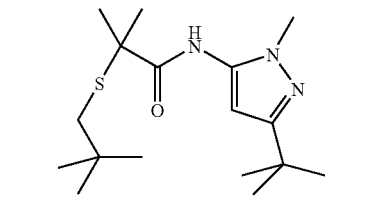 | N-(5-tert-Butyl-2-methyl-2H-pyrazol-3-yl)-2-(2,2-dimethyl-propylsulfanyl)-2-methyl-propionamide | 63 | 326 |
| 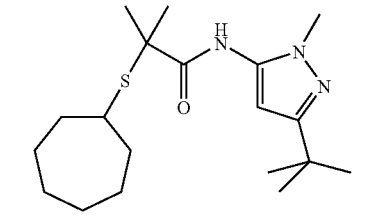 | N-(5-tert-Butyl-2-methyl-2H-pyrazol-3-yl)-2-cycloheptylsulfanyl-2-methyl-propionamide | 68 | 352 |

TABLE 12-continued

| MOLSTRUCTURE | NAME | YIELD [%] | m/z [M + H+] |
|---|---|---|---|
| | N-(5-tert-Butyl-2-methyl-2H-pyrazol-3-yl)-2-cyclohexylmethylsulfanyl-2-methyl-propionamide | 95 | 352 |
| | 2-Methyl-2-(tetrahydro-furan-2-ylmethylsulfanyl)-N-(5-trifluoromethyl-pyridin-2-yl)-propionamide | 53 | 349 |
| | 2-Methyl-2-(tetrahydro-pyran-2-ylmethylsulfanyl)-N-(5-trifluoromethyl-pyridin-2-yl)-propionamide | 54 | 363 |
| | 2-(3,3-Dimethyl-2-oxo-butylsulfanyl)-2-methyl-N-(5-trifluoromethyl-pyridin-2-yl)-propionamide | 45 | 363 |
| | N-(5-tert-Butyl-isoxazol-3-yl)-2-(3,3-dimethyl-2-oxo-butylsulfanyl)-2-methyl-propionamide | 75 | 341 |
| | N-(5-tert-Butyl-2-methyl-2H-pyrazol-3-yl)-2-methyl-2-((S)-5-oxo-pyrrolidin-2-ylmethylsulfanyl)-propionamide | 85 | 353 |
| | N-(5-tert-Butyl-2-methyl-2H-pyrazol-3-yl)-2-methyl-2-((R)-5-oxo-pyrrolidin-2-ylmethylsulfanyl)-propionamide | 97 | 353 |

TABLE 12-continued

| MOLSTRUCTURE | NAME | YIELD [%] | m/z [M + H+] |
|---|---|---|---|
| | N-(5-tert-Butyl-isoxazol-3-yl)-2-methyl-2-(3-methyl-butylsulfanyl)-propionamide | 70 | 313 |
| | N-(5-tert-Butyl-2-methyl-2H-pyrazol-3-yl)-2-methyl-2-(3-methyl-butylsulfanyl)-propionamide | 90 | 326 |
| | N-(5-tert-Butyl-isoxazol-3-yl)-2-cycloheptylsulfanyl-2-methyl-propionamide | 89 | 339 |
| | 2-Cycloheptylsulfanyl-2-methyl-N-(5-trifluoromethyl-pyridin-2-yl)-propionamide | 83 | 361 |
| | 2-Cyclopropylmethylsulfanyl-2-methyl-N-(5-trifluoromethyl-pyridin-2-yl)-propionamide | 100 | 319 |
| | 2-Cyclobutylmethylsulfanyl-2-methyl-N-(5-trifluoromethyl-pyridin-2-yl)-propionamide | 97 | 333 |
| | 2-Methyl-2-(3-phenyl-propylsulfanyl)-N-(5-trifluoromethyl-pyridin-2-yl)-propionamide | 82 | 383 |
| | N-(5-tert-Butyl-isoxazol-3-yl)-2-cyclopropylmethylsulfanyl-2-methyl-propionamide | 74 | 297 |

TABLE 12-continued

| MOLSTRUCTURE | NAME | YIELD [%] | m/z [M + H+] |
|---|---|---|---|
| | N-(5-tert-Butyl-isoxazol-3-yl)-2-cyclobutylmethylsulfanyl-2-methyl-propionamide | 77 | 311 |
| | N-(5-tert-Butyl-isoxazol-3-yl)-2-methyl-2-(3-phenyl-propylsulfanyl)-propionamide | 86 | 361 |
| | 2-Cycloheptylsulfanyl-2-methyl-N-(5-trifluoromethyl-pyridin-2-yl)-propionamide | 83 | 361 |
| | N-(3-tert-Butyl-isoxazol-5-yl)-2-cyclobutylmethylsulfanyl-2-methyl-propionamide | 55 | 311 |
| | N-(3-tert-Butyl-isoxazol-5-yl)-2-cyclopropylmethylsulfanyl-2-methyl-propionamide | 70 | 297 |
| | N-(3-tert-Butyl-isoxazol-5-yl)-2-methyl-2-(3-methyl-butylsulfanyl)-propionamide | 50 | 313 |
| | N-(3-tert-Butyl-isoxazol-5-yl)-2-cyclohexylmethylsulfanyl-2-methyl-propionamide | 50 | 339 |
| | N-(3-tert-Butyl-isoxazol-5-yl)-2-sec-butylsulfanyl-2-methyl-propionamide | 73 | 299 |

TABLE 12-continued

| MOLSTRUCTURE | NAME | YIELD [%] | m/z [M + H⁺] |
|---|---|---|---|
| | N-(3-tert-Butyl-isoxazol-5-yl)-2-methyl-2-(tetrahydro-pyran-2-ylmethylsulfanyl)-propionamide | 75 | 341 |
| | N-(3-tert-Butyl-isoxazol-5-yl)-2-isobutylsulfanyl-2-methyl-propionamide | 73 | 299 |
| | N-(3-tert-Butyl-isoxazol-5-yl)-2-methyl-2-(tetrahydro-furan-2-ylmethylsulfanyl)-propionamide | 100 | 327 |
| | N-(3-tert-Butyl-isoxazol-5-yl)-2-methyl-2-(tetrahydro-furan-3-ylmethylsulfanyl)-propionamide | 100 | 327 |

Step 3: Synthesis of N-(5-tert-Butyl-isoxazol-3-yl)-2-methyl-2-(tetrahydro-pyran-4-ylmethanesulfonyl)-propionamide To a solution of 119 mg (0.365 mmol) of N-(5-tert-butyl-isoxazol-3-yl)-2-methyl-2-(tetrahydro-pyran-2-ylmethylsulfanyl)-propionamide in acetic acid (1 mL) were added 103 µL (1.83 mmol) of hydrogen peroxide (50% solution, stabilized in water) and heated to 80° C. for 50 minutes. The colorless solution was quenched with ethanol (2 mL) and concentrated under reduced pressure. The crude material was purified by mass-triggered preparative LCMS and residual TFA was removed by filtration through a small plug of Ambersep 900-OH resin to yield 27 mg of N-(5-tert-butyl-isoxazol-3-yl)-2-methyl-2-(tetrahydro-pyran-4-ylmethanesulfonyl)-propionamide.

Examples listed in Table 17, Method G were made according to this procedure.

Method H

Synthesis of 2-Methyl-2-(piperidin-4-ylmethanesulfonyl)-N-(5-trifluoromethyl-pyridin-2-yl)-propionamide Example 98, Table 17

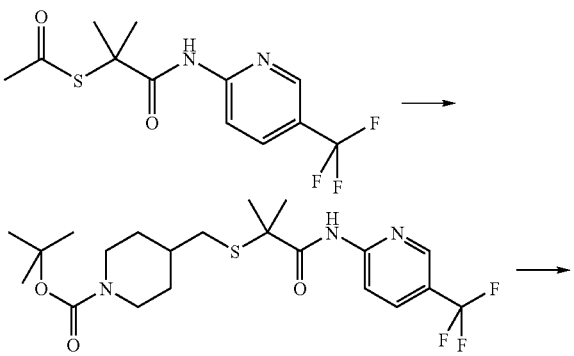

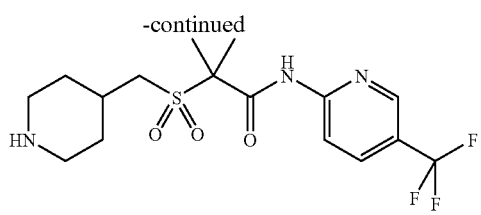

Step 1: Synthesis of 4-[1-Methyl-1-(5-trifluoromethyl-pyridin-2-ylcarbamoyl)-ethylsulfanylmethyl]-piperidine-1-carboxylic acid tert-butyl ester To a solution of 200 mg (0.654 mmol) of thioacetic acid S-[1-methyl-1-(5-trifluoromethyl-pyridin-2-ylcarbamoyl)-ethyl]ester (synthesized according to Method F, step 1) in ethanol (2 mL) were added 363 mg (1.31 mmol) of 4-bromomethyl-piperidine-1-carboxylic acid tert-butyl ester and 141 mg (2.61 mmol) of sodium methoxide at room temperature. The reaction was heated to 130° C. for 0.5 h within a microwave (CEM Discover). The reaction mixture was concentrated under reduced pressure. The residue was dissolved in DCM (4 mL) and washed with saturated aqueous $NaHCO_3$ solution (5 mL). The organic phase was dried over $Na_2SO_4$, filtered and the filtrate was concentrated under reduced pressure to yield 375 mg of 4-[1-methyl-1-(5-trifluoromethyl-pyridin-2-ylcarbamoyl)-ethylsulfanylmethyl]-piperidine-1-carboxylic acid tert-butyl ester.

According to this procedure the following thioethers were synthesized:

TABLE 13

| MOLSTRUCTURE | NAME | YIELD [%] | m/z [M + H⁺] |
|---|---|---|---|
| | 4-[1-(5-tert-Butyl-isoxazol-3-ylcarbamoyl)-1-methyl-ethylsulfanylmethyl]-piperidine-1-carboxylic acid tert-butyl ester | 89 | 462 [M + Na⁺], 340 [M + H⁺ − $C_5H_8O_2$] |
| | 4-[1-Methyl-1-(5-trifluoromethyl-pyridin-2-ylcarbamoyl)-ethylsulfanylmethyl]-piperidine-1-carboxylic acid tert-butyl ester | 100 | 462 [M + H⁺], 485 [M + Na⁺] |
| | 3-[1-(5-tert-Butyl-isoxazol-3-ylcarbamoyl)-1-methyl-ethylsulfanylmethyl]-piperidine-1-carboxylic acid tert-butyl ester | 88 | 462 [M + Na⁺], 340 [M + H⁺ − $C_5H_8O_2$] |
| | 3-[1-(5-tert-Butyl-isoxazol-3-ylcarbamoyl)-1-methyl-ethylsulfanylmethyl]-pyrrolidine-1-carboxylic acid tert-butyl ester | 30 | 426 [M + H⁺], 448 [M + Na⁺], 326 [M + H⁺ − $C_5H_8O_2$] |

Step 2: Synthesis of 2-Methyl-2-(piperidin-4-yl-methanesulfonyl)-N-(5-trifluoromethyl-pyridin-2-yl)-propionamide To a solution of 375 mg (0.81 mmol) of 4-[1-methyl-1-(5-trifluoromethyl-pyridin-2-ylcarbamoyl)-ethylsulfanylmethyl]-piperidine-1-carboxylic acid tert-butyl ester in acetic acid (1 ml) were added 241 µL (4.26 mmol) of hydrogen peroxide (50% solution, stabilized in water) and heated to 80° C. for 50 minutes. The colorless solution was quenched with ethanol (2 mL) and concentrated under reduced pressure. The crude material was treated with a solution of 10% TFA in DCM (5 mL) for 16 h. The solvents were removed under reduced pressure. The residue was purified by mass triggered preparative LC and residual TFA was removed by filtration through a small plug of Ambersep 900-OH resin to yield 24.8 mg of 2-methyl-2-(piperidin-4-ylmethanesulfonyl)-N-(5-trifluoromethyl-pyridin-2-yl)-propionamide.

Examples listed in Table 17, Method H were made according to this procedure.

Method I

Synthesis of 2-(1-Acetyl-piperidin-3-ylmethanesulfonyl)-N-(5-tert-butyl-isoxazol-3-yl)-2-methyl-propionamide Example 39, Table 17

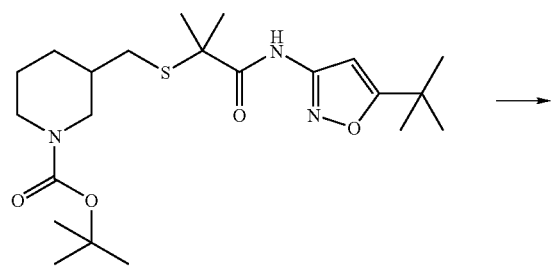

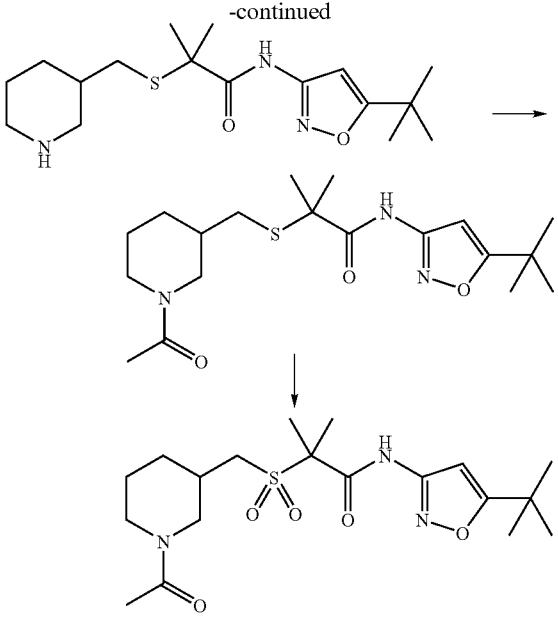

Step 1: Synthesis of N-(5-tert-Butyl-isoxazol-3-yl)-2-methyl-2-(piperidin-3-ylmethylsulfanyl)-propionamide To a solution of 288 mg (0.65 mmol) of 3-[1-(5-tert-butyl-isoxazol-3-ylcarbamoyl)-1-methyl-ethylsulfanylmethyl]-piperidine-1-carboxylic acid tert-butyl ester (synthesized according to Method H, step 1) in DCM (5 mL) were added 1.1 mL of HCl (2M solution in dioxane). The reaction was stirred at room temperature for 16 h. The mixture was diluted with saturated aqueous NaHCO$_3$ solution (5 mL), the organic layer was separated and dried over Na$_2$SO$_4$. Filtration and concentration of the filtrate under reduced pressure afforded 175 mg of N-(5-tert-butyl-isoxazol-3-yl)-2-methyl-2-(piperidin-3-ylmethylsulfanyl)-propionamide.

According to this procedure the following thioethers were synthesized

TABLE 14

| MOLSTRUCTURE | NAME | YIELD [%] | m/z [M + H$^+$] |
|---|---|---|---|
|  | N-(5-tert-Butyl-isoxazol-3-yl)-2-methyl-2-(piperidin-3-ylmethylsulfanyl)-propionamide | 79 | 340 |
|  | N-(5-tert-Butyl-isoxazol-3-yl)-2-methyl-2-(pyrrolidin-3-ylmethylsulfanyl)-propionamide | 89 | 326 |

Step 2: Synthesis of 2-(1-Acetyl-piperidin-3-ylmethylsulfanyl)-N-(5-tert-butyl-isoxazol-3-yl)-2-methyl-propionamide A solution of 175 mg (0.52 mmol) of N-(5-tert-butyl-isoxazol-3-yl)-2-methyl-2-(piperidin-3-ylmethylsulfanyl)-propionamide 0.18 mL (1.04 mmol) of N,N-diisopropylethylamine and acetic anhydride (1.5 mL) were heated for 0.5 h to 100° C. within a microwave (CEM discover). The solvent was removed under reduced pressure. The residue was dissolved in DCM (5 mL) and washed with saturated aqueous NaHCO₃ solution (5 mL). The organic phase was dried over Na₂SO₄, filtered and the filtrate concentrated under reduced pressure to afford 183 mg of 2-(1-acetyl-piperidin-3-ylmethylsulfanyl)-N-(5-tert-butyl-isoxazol-3-yl)-2-methyl-propionamide, which was used in the next step without further purification.

According to this method the following amides were synthesized.

TABLE 15

| MOLSTRUCTURE | NAME | YIELD [%] | m/z [M + H⁺] |
|---|---|---|---|
| (structure) | 2-(1-Acetyl-piperidin-3-ylmethylsulfanyl)-N-(5-tert-butyl-isoxazol-3-yl)-2-methyl-propionamide | 92 | 382 |
| (structure) | 2-(1-Acetyl-pyrrolidin-3-ylmethylsulfanyl)-N-(5-tert-butyl-isoxazol-3-yl)-2-methyl-propionamide | 80 | 368 |

Step 3: Synthesis of 2-(1-Acetyl-piperidin-3-yl-methanesulfonyl)-N-(5-tert-butyl-isoxazol-3-yl)-2-methyl-propionamide To a solution of 183 mg (0.48 mmol) of 2-(1-acetyl-piperidin-3-ylmethylsulfanyl)-N-(5-tert-butyl-isoxazol-3-yl)-2-methyl-propionamide in DCM (5 mL) were added 123 mg (0.72 mmol) of m-chloroperoxybenzoic acid. The reaction was stirred at room temperature until completion. Then 774 mg (2.4 mmol) of aminomethylene polystyrene were added to the reaction and the mixture was shaken for 18 h. The resins were separated by filtration and rinsed with DCM. The filtrate was concentrated under reduced pressure and purified by mass triggered preparative LCMS (at neutral pH) to afford 34 mg of 2-(1-acetyl-piperidin-3-ylmethanesulfonyl)-N-(5-tert-butyl-isoxazol-3-yl)-2-methyl-propionamide.

Examples listed in Table 17, Method I were made according to this procedure.

Method J
Synthesis of N-(5-tert-Butyl-isoxazol-3-yl)-2-(1-methanesulfonyl-pyrrolidin-3-ylmethanesulfonyl)-2-methyl-propionamide Example 127, Table 17

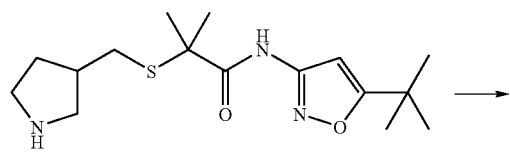

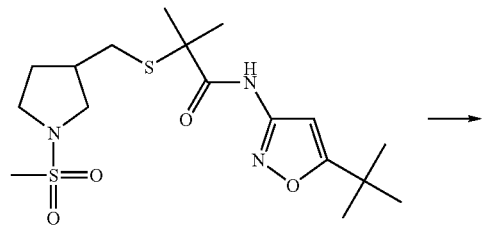

Step 1: Synthesis of N-(5-tert-Butyl-isoxazol-3-yl)-2-(1-methanesulfonyl-pyrrolidin-3-ylmethylsulfanyl)-2-methyl-propionamide To a solution of 172 mg (0.52 mmol) of N-(5-tert-butyl-isoxazol-3-yl)-2-methyl-2-(pyrrolidin-3-ylmethylsulfanyl)-propionamide (prepared according to Method I, step 1) and 0.18 mL (1.04 mmol) of N,N-diisopropylethylamine in THF were added 0.16 mL (2.11 mmol) of methanesulfonyl chloride. The reaction was heated within a microwave to 90° C. for 0.5 h. The mixture was concentrated under reduced pressure. The residue was dissolved in DCM (5 mL) and washed with saturated aqueous NaHCO₃ solution (5 mL). The organic layer was dried over Na₂SO₄, filtered and the filtrate was concentrated under reduced pressure to afford 168 mg of N-(5-tert-butyl-isoxazol-3-yl)-2-(1-methanesulfonyl-pyrrolidin-3-ylmethylsulfanyl)-2-methyl-propionamide, which was used in the next step without further purification.

According to this method, the following sulfonamides were synthesized.

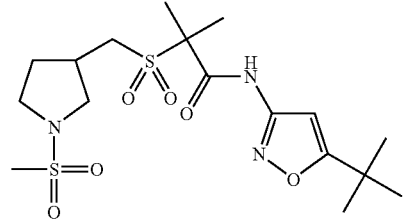

TABLE 16

| MOLSTRUCTURE | NAME | YIELD [%] | m/z [M + H⁺] |
|---|---|---|---|
| (structure) | N-(5-tert-Butyl-isoxazol-3-yl)-2-(1-methanesulfonyl-piperidin-3-ylmethyl-sulfanyl)-2-methyl-propionamide | 73 | 418 |
| (structure) | N-(5-tert-Butyl-isoxazol-3-yl)-2-(1-methanesulfonyl-pyrrolidin-3-ylmethylsulfanyl)-2-methyl-propionamide | 78 | 404 |

Step 2: Synthesis of N-(5-tert-Butyl-isoxazol-3-yl)-2-(1-methanesulfonyl-pyrrolidin-3-ylmethanesulfonyl)-2-methyl-propionamide To a solution of 168 mg (0.41 mmol) of N-(5-tert-butyl-isoxazol-3-yl)-2-(1-methanesulfonyl-pyrrolidin-3-ylmethylsulfanyl)-2-methyl-propionamide in DCM (5 mL) were added 107 mg (0.63 mmol) of m-chloroperoxybenzoic acid. The reaction was stirred at room temperature until completion. Then 672 mg (2.08 mmol) of aminomethylene polystyrene were added to the reaction and the mixture was shaken for 18 h. The resins were separated by filtration and rinsed with DCM. The filtrate was concentrated under reduced pressure and the residue was purified by mass triggered preparative LCMS (at neutral pH) to afford 37 mg of N-(5-tert-butyl-isoxazol-3-yl)-2-(1-methanesulfonyl-pyrrolidin-3-ylmethanesulfonyl)-2-methyl-propionamide.

Examples listed in Table 17, Method J were made according to this procedure.

Method K

Synthesis of N-(5-tert-Butyl-isoxazol-3-yl)-2-methyl-2-(4-methyl-tetrahydro-pyran-4-sulfonyl)-propionamide Example 100, Table 17

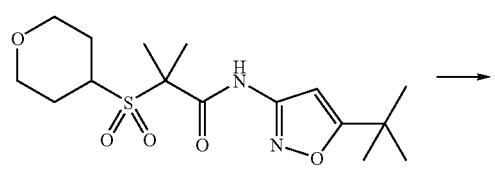

→

-continued

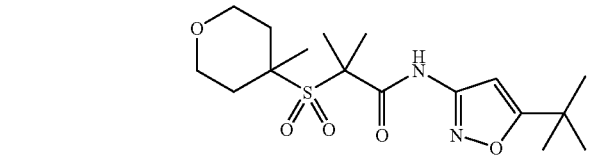

To a solution of 202 mg (0.56 mmol) of N-(5-tert-butyl-isoxazol-3-yl)-2-methyl-2-(tetrahydro-pyran-4-sulfonyl)-propionamide (prepared according to Method E) in anhydrous THF (10 mL) at −78° C. under nitrogen atmosphere were added 0.8 mL (1.4 mmol) of lithium diisopropylamide (1.8 M solution in THF/heptane/ethylbenzene) and the reaction was stirred at −78° C. for 0.5 h. Then 0.1 mL (1.6 mmol) of methyl iodide were added in one portion and stirring was continued for further 0.5 h at −78° C., before the reaction was warmed to room temperature. After 18 h at room temperature the reaction was quenched by the addition of saturated aqueous NH₄Cl solution (25 mL). The mixture was extracted with ethyl acetate (3×25 mL). The organic extracts were combined, dried over Na₂SO₄ and filtered. The filtrate was concentrated under reduced pressure and the residue purified by mass-triggered preparative LCMS to afford 31 mg of N-(5-tert-butyl-isoxazol-3-yl)-2-methyl-2-(4-methyl-tetrahydro-pyran-4-sulfonyl)-propionamide.

Examples listed in Table 17, Method K were made according to this procedure.

TABLE 17

Examples

| # | MOLSTRUCTURE | NAME | m/z [M + H⁺] | Method |
|---|---|---|---|---|
| 1 | | N-(5-tert-Butyl-isoxazol-3-yl)-2-cyclohexanesulfonyl-2-methyl-propionamide | 357 | A |
| 2 | | N-(4-tert-Butyl-thiazol-2-yl)-2-methyl-2-(propane-2-sulfonyl)-propionamide | 333 | A |
| 3 | | N-(5-tert-Butyl-4-methyl-thiazol-2-yl)-2-methyl-2-(propane-2-sulfonyl)-propionamide | 347 | A |
| 4 | | 1-Cyclohexanesulfonyl-cyclobutanecarboxylic acid (5-tert-butyl-isoxazol-3-yl)-amide | 369 | A |
| 5 | | 1-Cyclohexanesulfonyl-cyclobutanecarboxylic acid (4-tert-butyl-thiazol-2-yl)-amide | 385 | A |
| 6 | | N-(5-tert-Butyl-isoxazol-3-yl)-2-methyl-2-(propane-2-sulfonyl)-propionamide | 317 | A |
| 7 | | N-(4-tert-Butyl-thiazol-2-yl)-2-(4-chloro-phenylmethanesulfonyl)-2-methyl-propionamide | 415/417 | A |
| 8 | | N-(5-tert-Butyl-4-methyl-thiazol-2-yl)-2-(4-chloro-phenylmethanesulfonyl)-2-methyl-propionamide | 429/431 | A |

TABLE 17-continued

Examples

| # | MOLSTRUCTURE | NAME | m/z [M + H⁺] | Method |
|---|---|---|---|---|
| 9 | | N-(5-tert-Butyl-isoxazol-3-yl)-2-(4-chloro-phenylmethanesulfonyl)-2-methyl-propionamide | 399/401 | A |
| 10 | | N-(5-tert-Butyl-isoxazol-3-yl)-2-methyl-2-(propane-1-sulfonyl)-propionamide | 317 | C |
| 11 | | 2-Methyl-2-(propane-1-sulfonyl)-N-(4-trifluoromethyl-pyridin-2-yl)-propionamide | 339 | A |
| 12 | | 2-Methyl-N-naphthalen-2-yl-2-(propane-2-sulfonyl)-propionamide | 320.25 | A |
| 13 | | 2-Methyl-2-(propane-2-sulfonyl)-N-(4,5,6,7-tetrahydro-benzothiazol-2-yl)-propionamide | 331.35 | A |
| 14 | | 2-Methyl-N-(2-methyl-5-thiophen-2-yl-2H-pyrazol-3-yl)-2-(propane-2-sulfonyl)-propionamide | 356.21 | A |
| 15 | | N-Isoquinolin-3-yl-2-methyl-2-(propane-2-sulfonyl)-propionamide | 321.27 | A |

TABLE 17-continued

Examples

| # | MOLSTRUCTURE | NAME | m/z [M + H⁺] | Method |
|---|---|---|---|---|
| 16 | | 2-Methyl-2-(propane-2-sulfonyl)-N-(4-trifluoromethyl-thiazol-2-yl)-propionamide | 345.13 | A |
| 17 | | N-Benzothiazol-2-yl-2-methyl-2-(propane-2-sulfonyl)-propionamide | 327.23 | A |
| 18 | | N-(4-tert-Butyl-thiazol-2-yl)-2-methyl-2-(propane-1-sulfonyl)-propionamide | 333 | A |
| 19 | | 2-Methyl-2-(propane-2-sulfonyl)-N-quinolin-3-yl-propionamide | 321.36 | A |
| 20 | | N-(4-tert-Butyl-phenyl)-2-methyl-2-(propane-2-sulfonyl)-propionamide | 326.27 | A |
| 21 | | 2-Methyl-N-(4-phenyl-thiazol-2-yl)-2-(propane-2-sulfonyl)-propionamide | 353.26 | A |
| 22 | | 2-Methyl-2-(propane-2-sulfonyl)-N-(5-trifluoromethyl-pyridin-2-yl)-propionamide | 339.23 | A |

TABLE 17-continued

Examples

| # | MOLSTRUCTURE | NAME | m/z [M + H⁺] | Method |
|---|---|---|---|---|
| 23 | 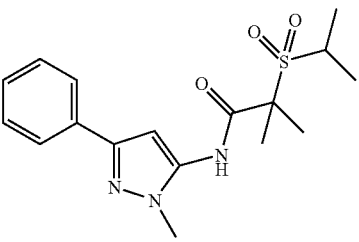 | 2-Methyl-N-(2-methyl-5-phenyl-2H-pyrazol-3-yl)-2-(propane-2-sulfonyl)-propionamide | 350.33 | A |
| 24 | 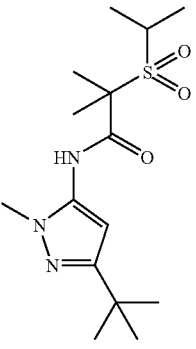 | N-(5-tert-Butyl-2-methyl-2H-pyrazol-3-yl)-2-methyl-2-(propane-2-sulfonyl)-propionamide | 330.29 | A |
| 25 | 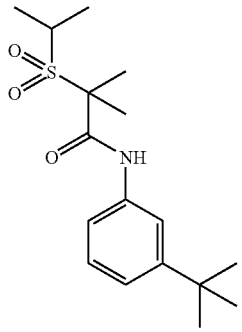 | N-(3-tert-Butyl-phenyl)-2-methyl-2-(propane-2-sulfonyl)-propionamide | 326.27 | A |
| 26 | 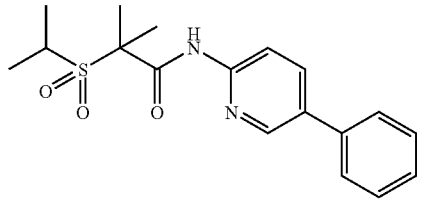 | 2-Methyl-N-(5-phenyl-pyridin-2-yl)-2-(propane-2-sulfonyl)-propionamide | 347.31 | A |
| 27 | 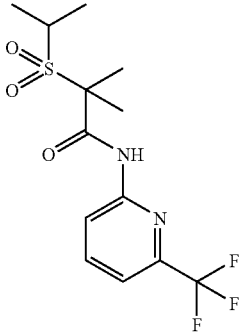 | 2-Methyl-2-(propane-2-sulfonyl)-N-(6-trifluoromethyl-pyridin-2-yl)-propionamide | 339.18 | A |

TABLE 17-continued

Examples

| # | MOLSTRUCTURE | NAME | m/z [M + H+] | Method |
|---|---|---|---|---|
| 28 | | N-(4-tert-Butyl-thiazol-2-yl)-2-cyclopentanesulfonyl-2-methyl-propionamide | 359 | A |
| 29 | | 2-Cyclohexanesulfonyl-2-methyl-N-(5-trifluoromethyl-pyridin-2-yl)-propionamide | 379 | A |
| 30 | | N-(5-tert-Butyl-isoxazol-3-yl)-2-cyclopentanesulfonyl-2-methyl-propionamide | 343 | A |
| 31 | | N-(5-tert-Butyl-isoxazol-3-yl)-2-cyclopropanesulfonyl-2-methyl-propionamide | 315 | C |
| 32 | | N-(5-tert-Butyl-isoxazol-3-yl)-2-methyl-2-(2-methyl-propane-2-sulfonyl)-propionamide | 331 | A |
| 33 | | N-(4-tert-Butyl-thiazol-2-yl)-2-methyl-2-(2-methyl-propane-2-sulfonyl)-propionamide | 347 | A |

TABLE 17-continued

Examples

| # | MOLSTRUCTURE | NAME | m/z [M + H⁺] | Method |
|---|---|---|---|---|
| 34 | | N-(5-tert-Butyl-4-methyl-thiazol-2-yl)-2-methyl-2-(2-methyl-propane-2-sulfonyl)-propionamide | 361 | A |
| 35 | | 2-Methyl-2-(2-methyl-propane-2-sulfonyl)-N-(5-trifluoromethyl-pyridin-2-yl)-propionamide | 353 | A |
| 36 | | N-(5-tert-Butyl-2-methyl-2H-pyrazol-3-yl)-2-methyl-2-(2-methyl-propane-2-sulfonyl)-propionamide | 344 | A |
| 37 | | 2-Methyl-2-(2-methyl-propane-2-sulfonyl)-N-(6-trifluoromethyl-pyridin-2-yl)-propionamide | 353 | A |
| 38 | | 2-Methyl-2-(2-methyl-propane-2-sulfonyl)-N-(4-trifluoromethyl-pyridin-2-yl)-propionamide | 353 | A |
| 39 | | 2-(1-Acetyl-piperidin-3-ylmethanesulfonyl)-N-(5-tert-butyl-isoxazol-3-yl)-2-methyl-propionamide | 414 | I |

TABLE 17-continued

Examples

| # | MOLSTRUCTURE | NAME | m/z [M + H+] | Method |
|---|---|---|---|---|
| 40 | | N-(5-tert-Butyl-isoxazol-3-yl)-2-(propane-2-sulfonyl)-propionamide | 303 | A |
| 41 | | N-(5-tert-Butyl-isoxazol-3-yl)-3-methyl-2-(propane-2-sulfonyl)-butyramide | 331 | A |
| 42 | | 2-(Butane-2-sulfonyl)-N-(5-tert-butyl-isoxazol-3-yl)-2-methyl-propionamide | 331 | A |
| 43 | | 2-(Butane-2-sulfonyl)-N-(5-tert-butyl-2-methyl-2H-pyrazol-3-yl)-2-methyl-propionamide | 344 | A |
| 44 | | 2-(Butane-2-sulfonyl)-N-(4-tert-butyl-thiazol-2-yl)-2-methyl-propionamide | 347 | A |
| 45 | | N-(4-tert-Butyl-thiazol-2-yl)-2-(propane-2-sulfonyl)-propionamide | 319 | A |
| 46 | | N-(4-tert-Butyl-thiazol-2-yl)-3-methyl-2-(propane-2-sulfonyl)-butyramide | 347 | A |

TABLE 17-continued

Examples

| # | MOLSTRUCTURE | NAME | m/z [M + H+] | Method |
|---|---|---|---|---|
| 47 | | N-(5-tert-Butyl-4-methyl-thiazol-2-yl)-3-methyl-2-(propane-2-sulfonyl)-butyramide | 361 | A |
| 48 | | 2-(Butane-2-sulfonyl)-2-methyl-N-(5-trifluoromethyl-pyridin-2-yl)-propionamide | 353 | A |
| 49 | | N-(5-tert-Butyl-2-methyl-2H-pyrazol-3-yl)-2-ethanesulfonyl-2-methyl-propionamide | 316 | A |
| 50 | | N-(5-tert-Butyl-2-methyl-2H-pyrazol-3-yl)-2-methanesulfonyl-2-methyl-propionamide | 302 | B |
| 51 | | N-(4-tert-Butyl-thiazol-2-yl)-2-methanesulfonyl-2-methyl-propionamide | 305 | B |
| 52 | | N-(5-tert-Butyl-isoxazol-3-yl)-2-methyl-2-(2-methyl-propane-1-sulfonyl)-propionamide | 331 | D |

TABLE 17-continued

Examples

| # | MOLSTRUCTURE | NAME | m/z [M + H⁺] | Method |
|---|---|---|---|---|
| 53 | | N-(5-tert-Butyl-isoxazol-3-yl)-2-methyl-2-(2,2,2-trifluoro-ethanesulfonyl)-propionamide | 357 | B |
| 54 | | N-(5-tert-Butyl-isoxazol-3-yl)-2-methanesulfonyl-2-methyl-propionamide | 289 | B |
| 55 | | 2-Methanesulfonyl-2-methyl-N-(5-trifluoromethyl-pyridin-2-yl)-propionamide | 311 | B |
| 56 | | N-(5-tert-Butyl-isoxazol-3-yl)-2-methyl-2-(tetrahydro-pyran-4-ylmethanesulfonyl)-propionamide | 373 | E |
| 57 | | N-(4-tert-Butyl-thiazol-2-yl)-2-methyl-2-(tetrahydro-pyran-4-ylmethanesulfonyl)-propionamide | 389 | E |
| 58 | | N-(5-tert-Butyl-4-methyl-thiazol-2-yl)-2-methyl-2-(tetrahydro-pyran-4-ylmethanesulfonyl)-propionamide | 403 | E |
| 59 | | N-(5-tert-Butyl-2-methyl-2H-pyrazol-3-yl)-2-methyl-2-(tetrahydro-pyran-4-ylmethanesulfonyl)-propionamide | 386 | E |

TABLE 17-continued

Examples

| # | MOLSTRUCTURE | NAME | m/z [M + H+] | Method |
|---|---|---|---|---|
| 60 | | 2-Methyl-2-(tetrahydro-pyran-4-ylmethanesulfonyl)-N-(5-trifluoromethyl-pyridin-2-yl)-propionamide | 395 | E |
| 61 | | 2-Methyl-2-(tetrahydro-pyran-4-ylmethanesulfonyl)-N-(6-trifluoromethyl-pyridin-2-yl)-propionamide | 395 | E |
| 62 | | N-(5-tert-Butyl-2-methyl-2H-pyrazol-3-yl)-2-cyclopentanesulfonyl-2-methyl-propionamide | 356 | A |
| 63 | | 2-Cyclopentanesulfonyl-2-methyl-N-(2-methyl-5-phenyl-2H-pyrazol-3-yl)-propionamide | 376 | A |
| 64 | | 2-Cyclopentanesulfonyl-2-methyl-N-(5-trifluoromethyl-pyridin-2-yl)-propionamide | 365 | A |
| 65 | | 2-Cyclopentanesulfonyl-2-methyl-N-(4-trifluoromethyl-thiazol-2-yl)-propionamide | 371 | A |
| 66 | | N-(5-tert-Butyl-isoxazol-3-yl)-2-methyl-2-(tetrahydro-pyran-4-sulfonyl)-propionamide | 359 | E |

TABLE 17-continued

Examples

| # | MOLSTRUCTURE | NAME | m/z [M + H+] | Method |
|---|---|---|---|---|
| 67 | | N-(4-tert-Butyl-thiazol-2-yl)-2-methyl-2-(tetrahydro-pyran-4-sulfonyl)-propionamide | 375 | E |
| 68 | | 2-Methyl-2-(tetrahydro-pyran-4-sulfonyl)-N-(5-trifluoromethyl-pyridin-2-yl)-propionamide | 381 | E |
| 69 | | 2-Methyl-N-(2-methyl-5-phenyl-2H-pyrazol-3-yl)-2-(tetrahydro-pyran-4-sulfonyl)-propionamide | 392 | E |
| 70 | | N-(5-tert-Butyl-4-methyl-thiazol-2-yl)-2-methyl-2-(tetrahydro-pyran-4-sulfonyl)-propionamide | 389 | E |
| 71 | | N-(5-tert-Butyl-2-methyl-2H-pyrazol-3-yl)-2-methyl-2-(tetrahydro-pyran-4-sulfonyl)-propionamide | 372 | E |
| 72 | | N-[4-(4-Chloro-phenyl)-thiazol-2-yl]-2-cyclopentanesulfonyl-2-methyl-propionamide | 413/415 | A |

TABLE 17-continued

Examples

| # | MOLSTRUCTURE | NAME | m/z [M + H+] | Method |
|---|---|---|---|---|
| 73 | | 2-Cyclopentanesulfonyl-2-methyl-N-(4-trifluoromethyl-pyridin-2-yl)-propionamide | 365 | A |
| 74 | | N-(5-tert-Butyl-isoxazol-3-yl)-2-methyl-2-(tetrahydro-furan-2-ylmethanesulfonyl)-propionamide | 359 | F |
| 75 | | N-(5-tert-Butyl-2-methyl-2H-pyrazol-3-yl)-2-cyclobutylmethanesulfonyl-2-methyl-propionamide | 356 | F |
| 76 | | N-(5-tert-Butyl-2-methyl-2H-pyrazol-3-yl)-2-(hexane-3-sulfonyl)-2-methyl-propionamide | 372 | F |
| 77 | | N-(3-tert-Butyl-isoxazol-5-yl)-2-cyclohexanesulfonyl-2-methyl-propionamide | 357 | A |
| 78 | | N-(5-tert-Butyl-2-methyl-2H-pyrazol-3-yl)-2-methyl-2-(tetrahydro-pyran-2-ylmethanesulfonyl)-propionamide | 386 | G |
| 79 | | N-(5-tert-Butyl-isoxazol-3-yl)-2-cyclohexylmethanesulfonyl-2-methyl-propionamide | 371 | G |

TABLE 17-continued

Examples

| # | MOLSTRUCTURE | NAME | m/z [M + H+] | Method |
|---|---|---|---|---|
| 80 | 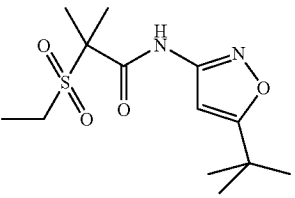 | N-(5-tert-Butyl-isoxazol-3-yl)-2-ethanesulfonyl-2-methyl-propionamide | 303 | G |
| 81 | 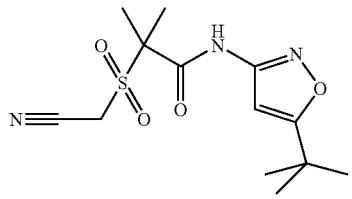 | N-(5-tert-Butyl-isoxazol-3-yl)-2-cyanomethanesulfonyl-2-methyl-propionamide | 314 | G |
| 82 | 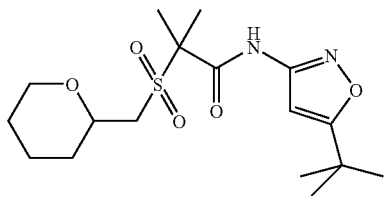 | N-(5-tert-Butyl-isoxazol-3-yl)-2-methyl-2-(tetrahydro-pyran-2-ylmethanesulfonyl)-propionamide | 373 | G |
| 83 | 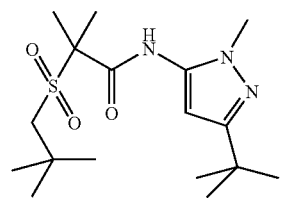 | N-(5-tert-Butyl-2-methyl-2H-pyrazol-3-yl)-2-(2,2-dimethyl-propane-1-sulfonyl)-2-methyl-propionamide | 358 | G |
| 84 | 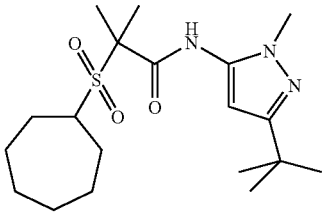 | N-(5-tert-Butyl-2-methyl-2H-pyrazol-3-yl)-2-cycloheptanesulfonyl-2-methyl-propionamide | 384 | G |
| 85 | 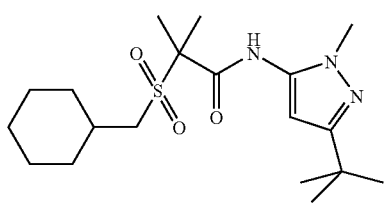 | N-(5-tert-Butyl-2-methyl-2H-pyrazol-3-yl)-2-cyclohexylmethanesulfonyl-2-methyl-propionamide | 384 | G |
| 86 | 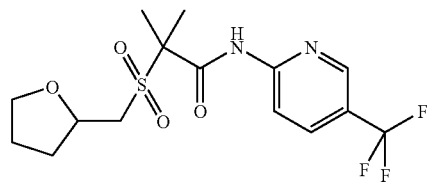 | 2-Methyl-2-(tetrahydro-furan-2-ylmethanesulfonyl)-N-(5-trifluoromethyl-pyridin-2-yl)-propionamide | 381 | G |

TABLE 17-continued

Examples

| # | MOLSTRUCTURE | NAME | m/z [M + H+] | Method |
|---|---|---|---|---|
| 87 | | 2-Methyl-2-(tetrahydro-pyran-2-ylmethanesulfonyl)-N-(5-trifluoromethyl-pyridin-2-yl)-propionamide | 395 | G |
| 88 | | 2-(3,3-Dimethyl-2-oxo-butane-1-sulfonyl)-2-methyl-N-(5-trifluoromethyl-pyridin-2-yl)-propionamide | 395 | G |
| 89 | | N-(5-tert-Butyl-isoxazol-3-yl)-2-(3,3-dimethyl-2-oxo-butane-1-sulfonyl)-2-methyl-propionamide | 373 | G |
| 90 | | N-(5-tert-Butyl-2-methyl-2H-pyrazol-3-yl)-2-methyl-2-((S)-5-oxo-pyrrolidin-2-ylmethanesulfonyl)-propionamide | 385 | G |
| 91 | | N-(5-tert-Butyl-2-methyl-2H-pyrazol-3-yl)-2-methyl-2-((R)-5-oxo-pyrrolidin-2-ylmethanesulfonyl)-propionamide | 385 | G |
| 92 | | N-(5-tert-Butyl-isoxazol-3-yl)-2-methyl-2-(3-methyl-butane-1-sulfonyl)-propionamide | 345 | G |
| 93 | | N-(5-tert-Butyl-2-methyl-2H-pyrazol-3-yl)-2-methyl-2-(3-methyl-butane-1-sulfonyl)-propionamide | 358 | G |

TABLE 17-continued

Examples

| # | MOLSTRUCTURE | NAME | m/z [M + H+] | Method |
|---|---|---|---|---|
| 94 | | N-(5-tert-Butyl-isoxazol-3-yl)-2-cycloheptanesulfonyl-2-methyl-propionamide | 371 | G |
| 95 | | N-(5-tert-Butyl-isoxazol-3-yl)-2-methyl-2-(piperidin-4-ylmethanesulfonyl)-propionamide | 372 | H |
| 96 | | 2-Cyclohexylmethanesulfonyl-2-methyl-N-(5-trifluoromethyl-pyridin-2-yl)-propionamide | 393 | G |
| 97 | | 2-Methyl-2-(3-methyl-butane-1-sulfonyl)-N-(5-trifluoromethyl-pyridin-2-yl)-propionamide | 367 | G |
| 98 | | 2-Methyl-2-(piperidin-4-ylmethanesulfonyl)-N-(5-trifluoromethyl-pyridin-2-yl)-propionamide | 394 | H |
| 99 | | N-(5-tert-Butyl-2-methyl-2H-pyrazol-3-yl)-2-methyl-2-(tetrahydro-furan-2-ylmethanesulfonyl)-propionamide | 372 | G |
| 100 | | N-(5-tert-Butyl-isoxazol-3-yl)-2-methyl-2-(4-methyl-tetrahydro-pyran-4-sulfonyl)-propionamide | 373 | K |

TABLE 17-continued

Examples

| # | MOLSTRUCTURE | NAME | m/z [M + H⁺] | Method |
|---|---|---|---|---|
| 101 | | 2-Cycloheptanesulfonyl-2-methyl-N-(5-trifluoromethyl-pyridin-2-yl)-propionamide | 393 | G |
| 102 | | 2-Cyclopropylmethanesulfonyl-2-methyl-N-(5-trifluoromethyl-pyridin-2-yl)-propionamide | 351 | G |
| 103 | | 2-Cyclobutylmethanesulfonyl-2-methyl-N-(5-trifluoromethyl-pyridin-2-yl)-propionamide | 365 | G |
| 104 | | N-(5-tert-Butyl-isoxazol-3-yl)-2-cyclopropylmethanesulfonyl-2-methyl-propionamide | 329 | G |
| 105 | | N-(5-tert-Butyl-isoxazol-3-yl)-2-cyclobutylmethanesulfonyl-2-methyl-propionamide | 343 | G |
| 106 | | N-(5-tert-Butyl-isoxazol-3-yl)-2-methyl-2-(3-phenyl-propane-1-sulfonyl)-propionamide | 393 | G |
| 107 | | N-(3-tert-Butyl-isoxazol-5-yl)-2-methyl-2-(propane-2-sulfonyl)-propionamide | 317 | A |
| 108 | | N-[4-(4-Chloro-phenyl)-thiazol-2-yl]-2-methyl-2-(propane-2-sulfonyl)-propionamide | 387/389 | A |

TABLE 17-continued

Examples

| # | MOLSTRUCTURE | NAME | m/z [M + H⁺] | Method |
|---|---|---|---|---|
| 109 | | 2-Methyl-2-(propane-2-sulfonyl)-N-(4-pyridin-3-yl-thiazol-2-yl)-propionamide | 354 | A |
| 110 | | 2-Methyl-2-(propane-2-sulfonyl)-N-(4-pyridin-2-yl-thiazol-2-yl)-propionamide | 354 | A |
| 111 | | 2-Methyl-2-(propane-2-sulfonyl)-N-(4-pyridin-2-yl-thiazol-2-yl)-propionamide | 354 | A |
| 112 | | 2-Methyl-2-(propane-2-sulfonyl)-N-quinolin-2-yl-propionamide | 321 | A |
| 113 | | 2-Methyl-2-(propane-1-sulfonyl)-N-quinolin-3-yl-propionamide | 321 | A |
| 114 | | N-(4-tert-Butyl-phenyl)-2-methyl-2-(propane-1-sulfonyl)-propionamide | 326 | A |
| 115 | | 2-Methyl-2-(propane-1-sulfonyl)-N-(4,5,6,7-tetrahydro-benzothiazol-2-yl)-propionamide | 331 | A |
| 116 | | 2-Methyl-2-(propane-1-sulfonyl)-N-quinolin-2-yl-propionamide | 321 | A |

TABLE 17-continued

Examples

| # | NAME | m/z [M + H+] | Method |
|---|------|--------------|--------|
| 1117 | N-[4-(4-Chloro-phenyl)-thiazol-2-yl]-2-methyl-2-(propane-1-sulfonyl)-propionamide | 387/389 | A |
| 118 | 2-Methyl-N-(2-methyl-5-phenyl-2H-pyrazol-3-yl)-2-(propane-1-sulfonyl)-propionamide | 350 | A |
| 119 | N-(5-tert-Butyl-2-methyl-2H-pyrazol-3-yl)-2-methyl-2-(propane-1-sulfonyl)-propionamide | 330 | A |
| 120 | 2-Methyl-N-(2-methyl-5-thiophen-2-yl-2H-pyrazol-3-yl)-2-(propane-1-sulfonyl)-propionamide | 356 | A |
| 121 | N-(3-tert-Butyl-phenyl)-2-methyl-2-(propane-1-sulfonyl)-propionamide | 326 | A |
| 122 | 2-Methyl-2-(propane-1-sulfonyl)-N-(4-pyridin-4-yl-thiazol-2-yl)-propionamide | 354 | A |
| 123 | 2-Methyl-2-(propane-1-sulfonyl)-N-(4-trifluoromethyl-thiazol-2-yl)-propionamide | 345 | A |

TABLE 17-continued

Examples

| # | MOLSTRUCTURE | NAME | m/z [M + H+] | Method |
|---|---|---|---|---|
| 124 | | N-(3-tert-Butyl-isoxazol-5-yl)-2-methyl-2-(propane-1-sulfonyl)-propionamide | 317 | A |
| 125 | | N-Benzothiazol-2-yl-2-methyl-2-(propane-1-sulfonyl)-propionamide | 327 | A |
| 126 | | 2-Methyl-2-(propane-1-sulfonyl)-N-(5-trifluoromethyl-pyridin-2-yl)-propionamide | 339 | A |
| 127 | | N-(5-tert-Butyl-isoxazol-3-yl)-2-(1-methanesulfonyl-pyrrolidin-3-ylmethanesulfonyl)-2-methyl-propionamide | 436 | J |
| 128 | | 2-Methyl-N-(5-methyl-4-phenyl-thiazol-2-yl)-2-(propane-1-sulfonyl)-propionamide | 367 | A |
| 129 | | N-(5-Ethyl-4-phenyl-thiazol-2-yl)-2-methyl-2-(propane-1-sulfonyl)-propionamide | 381 | A |

TABLE 17-continued

Examples

| # | MOLSTRUCTURE | NAME | m/z [M + H+] | Method |
|---|---|---|---|---|
| 130 | | 2-Methyl-N-(5-phenyl-pyridin-2-yl)-2-(propane-1-sulfonyl)-propionamide | 347 | A |
| 131 | | N-(4-Cyclohexyl-thiazol-2-yl)-2-methyl-2-(propane-1-sulfonyl)-propionamide | 359 | A |
| 132 | | N-(5-tert-Butyl-4-methyl-thiazol-2-yl)-2-methyl-2-(propane-1-sulfonyl)-propionamide | 347 | A |
| 133 | | N-(2,4-Dimethyl-5-phenyl-2H-pyrazol-3-yl)-2-methyl-2-(propane-1-sulfonyl)-propionamide | 364 | A |
| 134 | | N-[3-(2,2-Dimethyl-propyl)-isoxazol-5-yl]-2-methyl-2-(propane-1-sulfonyl)-propionamide | 331 | A |

TABLE 17-continued

Examples

| # | MOLSTRUCTURE | NAME | m/z [M + H⁺] | Method |
|---|---|---|---|---|
| 135 | 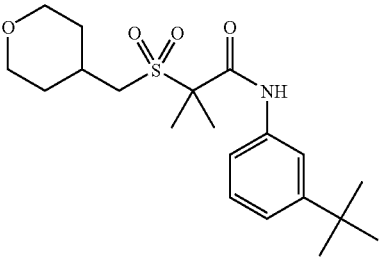 | N-(3-tert-Butyl-phenyl)-2-methyl-2-(tetrahydro-pyran-4-ylmethanesulfonyl)-propionamide | 382 | E |
| 136 | 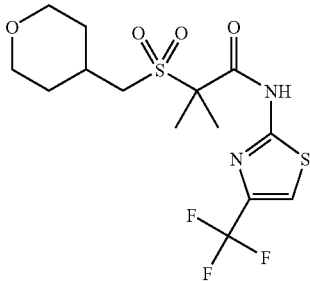 | 2-Methyl-2-(tetrahydro-pyran-4-ylmethanesulfonyl)-N-(4-trifluoromethyl-thiazol-2-yl)-propionamide | 401 | E |
| 137 | 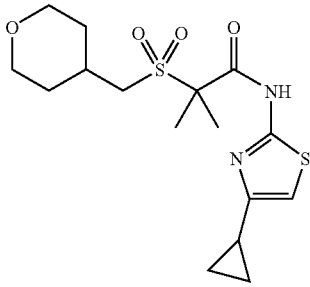 | N-(4-Cyclopropyl-thiazol-2-yl)-2-methyl-2-(tetrahydro-pyran-4-ylmethanesulfonyl)-propionamide | 373 | E |
| 138 | 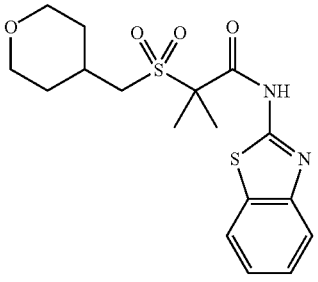 | N-Benzothiazol-2-yl-2-methyl-2-(tetrahydro-pyran-4-ylmethanesulfonyl)-propionamide | 383 | E |
| 139 | 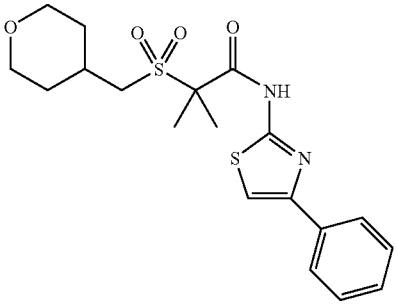 | 2-Methyl-N-(4-phenyl-thiazol-2-yl)-2-(tetrahydro-pyran-4-ylmethanesulfonyl)-propionamide | 409 | E |

TABLE 17-continued

Examples

| # | MOLSTRUCTURE | NAME | m/z [M + H+] | Method |
|---|---|---|---|---|
| 140 | 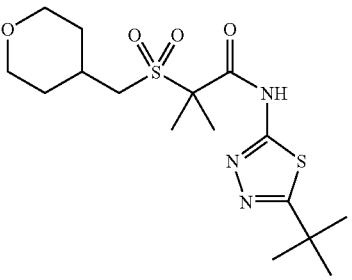 | N-(5-tert-Butyl-[1,3,4]thiadiazol-2-yl)-2-methyl-2-(tetrahydro-pyran-4-ylmethanesulfonyl)-propionamide | 390 | E |
| 141 | 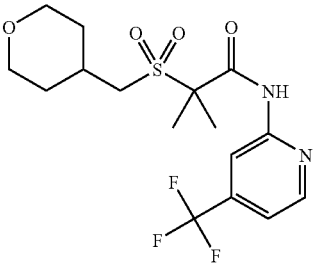 | 2-Methyl-2-(tetrahydro-pyran-4-ylmethanesulfonyl)-N-(4-trifluoromethyl-pyridin-2-yl)-propionamide | 395 | E |
| 142 | 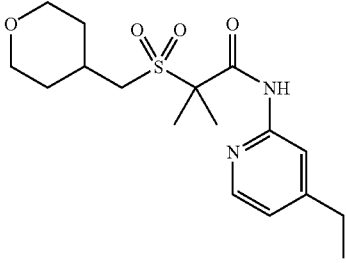 | N-(4-Ethyl-pyridin-2-yl)-2-methyl-2-(tetrahydro-pyran-4-ylmethanesulfonyl)-propionamide | 355 | E |
| 143 | 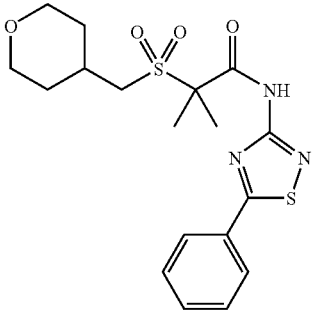 | 2-Methyl-N-(5-phenyl-[1,2,4]thiadiazol-3-yl)-2-(tetrahydro-pyran-4-ylmethanesulfonyl)-propionamide | 410 | E |
| 144 | 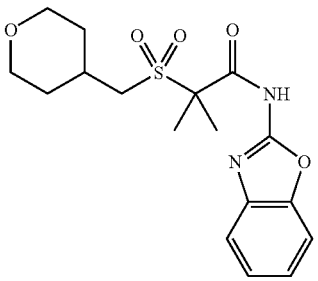 | N-Benzooxazol-2-yl-2-methyl-2-(tetrahydro-pyran-4-ylmethanesulfonyl)-propionamide | 367 | E |

TABLE 17-continued

Examples

| # | NAME | m/z [M + H+] | Method |
|---|------|---------------|--------|
| 145 | 2-Methyl-N-(5-methyl-4-phenyl-thiazol-2-yl)-2-(tetrahydro-pyran-4-ylmethanesulfonyl)-propionamide | 423 | E |
| 146 | N-(5-Ethyl-4-phenyl-thiazol-2-yl)-2-methyl-2-(tetrahydro-pyran-4-ylmethanesulfonyl)-propionamide | 437 | E |
| 147 | N-(4-Cyclohexyl-thiazol-2-yl)-2-methyl-2-(tetrahydro-pyran-4-ylmethanesulfonyl)-propionamide | 415 | E |
| 148 | 2-Methyl-N-(3-propyl-isoxazol-5-yl)-2-(tetrahydro-pyran-4-ylmethanesulfonyl)-propionamide | 359 | E |
| 149 | N-(5-Isopropyl-2-methyl-2H-pyrazol-3-yl)-2-methyl-2-(tetrahydro-pyran-4-ylmethanesulfonyl)-propionamide | 372 | E |

TABLE 17-continued

| # | NAME | m/z [M + H+] | Method |
|---|---|---|---|
| 150 | N-(2,4-Dimethyl-5-phenyl-2H-pyrazol-3-yl)-2-methyl-2-(tetrahydro-pyran-4-ylmethanesulfonyl)-propionamide | 420 | E |
| 151 | N-[3-(2,2-Dimethyl-propyl)-isoxazol-5-yl]-2-methyl-2-(tetrahydro-pyran-4-ylmethanesulfonyl)-propionamide | 387 | E |
| 152 | 2-Methyl-N-naphthalen-1-yl-2-(tetrahydro-pyran-4-ylmethanesulfonyl)-propionamide | 376 | E |
| 153 | 2-Methyl-N-(5-methyl-pyridin-2-yl)-2-(tetrahydro-pyran-4-ylmethanesulfonyl)-propionamide | 341 | E |
| 154 | 2-Methyl-N-quinolin-3-yl-2-(tetrahydro-pyran-4-ylmethanesulfonyl)-propionamide | 377 | E |

TABLE 17-continued

Examples

| # | MOLSTRUCTURE | NAME | m/z [M + H⁺] | Method |
|---|---|---|---|---|
| 155 | | 2-Methyl-2-(tetrahydro-pyran-4-ylmethanesulfonyl)-N-(3-trifluoromethyl-phenyl)-propionamide | 394 | E |
| 156 | | N-(4-tert-Butyl-phenyl)-2-methyl-2-(tetrahydro-pyran-4-ylmethanesulfonyl)-propionamide | 382 | E |
| 157 | | 2-Methyl-N-quinolin-2-yl-2-(tetrahydro-pyran-4-ylmethanesulfonyl)-propionamide | 377 | E |
| 158 | | N-[4-(4-Chloro-phenyl)-thiazol-2-yl]-2-methyl-2-(tetrahydro-pyran-4-ylmethanesulfonyl)-propionamide | 443 | E |
| 159 | | 2-Methyl-2-(tetrahydro-pyran-4-ylmethanesulfonyl)-N-(4-trifluoromethyl-phenyl)-propionamide | 394 | E |

TABLE 17-continued

Examples

| # | MOLSTRUCTURE | NAME | m/z [M + H+] | Method |
|---|---|---|---|---|
| 160 | | 2-Methyl-N-(2-methyl-5-phenyl-2H-pyrazol-3-yl)-2-(tetrahydro-pyran-4-ylmethanesulfonyl)-propionamide | 406 | E |
| 161 | | N-Isoquinolin-3-yl-2-methyl-2-(tetrahydro-pyran-4-ylmethanesulfonyl)-propionamide | 377 | E |
| 162 | | N-(3-tert-Butyl-isoxazol-5-yl)-2-methyl-2-(tetrahydro-pyran-4-ylmethanesulfonyl)-propionamide | 373 | E |
| 163 | | N-(3-tert-Butyl-isoxazol-5-yl)-2-methyl-2-(tetrahydro-pyran-4-sulfonyl)-propionamide | 359 | E |
| 164 | | N-(5-tert-Butyl-1,3,4-thiadiazol-2-yl)-2-cyclopentanesulfonyl-2-methyl-propionamide | 360 | A |
| 165 | | 2-Cyclopentanesulfonyl-2-methyl-N-(5-phenyl-4H-1,2,4-triazol-3-yl)-propionamide | 363 | A |

TABLE 17-continued

Examples

| # | MOLSTRUCTURE | NAME | m/z [M + H⁺] | Method |
|---|---|---|---|---|
| 166 | | N-(3-tert-Butyl-isoxazol-5-yl)-2-cyclobutylmethanesulfonyl-2-methyl-propionamide | 343 | G |
| 167 | | N-(3-tert-Butyl-isoxazol-5-yl)-2-cyclopropylmethanesulfonyl-2-methyl-propionamide | 329 | G |
| 168 | | N-(3-tert-Butyl-isoxazol-5-yl)-2-methyl-2-(3-methyl-butane-1-sulfonyl)-propionamide | 345 | G |
| 169 | | 2-Methyl-N-(5-phenyl-4H-1,2,4-triazol-3-yl)-2-(tetrahydro-pyran-4-ylmethanesulfonyl)-propionamide | 393 | E |
| 170 | | N-(3-tert-Butyl-isoxazol-5-yl)-2-cyclopentanesulfonyl-2-methyl-propionamide | 343 | A |
| 171 | | N-(3-tert-Butyl-isoxazol-5-yl)-2-cyclohexylmethanesulfonyl-2-methyl-propionamide | 371 | G |
| 172 | | 2-(Butane-2-sulfonyl)-N-(3-tert-butyl-isoxazol-5-yl)-2-methyl-propionamide | 331 | G |
| 173 | | N-(3-tert-Butyl-isoxazol-5-yl)-2-methyl-2-(tetrahydro-pyran-2-ylmethanesulfonyl)-propionamide | 373 | G |
| 174 | | N-(3-tert-Butyl-isoxazol-5-yl)-2-methyl-2-(2-methyl-propane-1-sulfonyl)-propionamide | 331 | G |

TABLE 17-continued

Examples

| # | NAME | m/z [M + H+] | Method |
|---|------|--------------|--------|
| 175 | 1-(Tetrahydro-pyran-4-ylmethanesulfonyl)-cyclobutanecarboxylic acid (3-tert-butyl-isoxazol-5-yl)-amide | 385 | E |
| 176 | N-(3-tert-Butyl-isoxazol-5-yl)-2-(4-fluoro-phenylmethanesulfonyl)-2-methyl-propionamide | 383 | D |
| 177 | N-(3-tert-Butyl-isoxazol-5-yl)-2-methyl-2-(tetrahydro-furan-2-ylmethanesulfonyl)-propionamide | 359 | G |
| 178 | N-(3-tert-Butyl-isoxazol-5-yl)-2-methyl-2-(tetrahydro-furan-3-ylmethanesulfonyl)-propionamide | 359 | G |
| 179 | 1-(Tetrahydro-pyran-4-ylmethanesulfonyl)-cyclobutanecarboxylic acid (3-tert-butyl-isoxazol-5-yl)-amide | 373 | E |
| 180 | 2-Methyl-N-(4-pyridin-3-yl-thiazol-2-yl)-2-(tetrahydro-pyran-4-ylmethanesulfonyl)-propionamide | 410 | E |

TABLE 17-continued

Examples

| # | MOLSTRUCTURE | NAME | m/z [M + H⁺] | Method |
|---|---|---|---|---|
| 181 | | 2-Methyl-N-(4-pyridin-2-yl-thiazol-2-yl)-2-(tetrahydro-pyran-4-ylmethanesulfonyl)-propionamide | 410 | E |
| 182 | | 2-Methyl-N-(4-pyridin-4-yl-thiazol-2-yl)-2-(tetrahydro-pyran-4-ylmethanesulfonyl)-propionamide | 410 | E |
| 183 | | N-[4-(4-Fluoro-phenyl)-thiazol-2-yl]-2-methyl-2-(tetrahydro-pyran-4-ylmethanesulfonyl)-propionamide | 427 | E |
| 184 | | N-(3-Isopropyl-isoxazol-5-yl)-2-methyl-2-(tetrahydro-pyran-4-ylmethanesulfonyl)-propionamide | 359 | E |
| 185 | | 2-Methyl-N-(3-phenyl-1,2,4-thiadiazol-5-yl)-2-(tetrahydro-pyran-4-ylmethanesulfonyl)-propionamide | 410 | E |

The following compounds can also be made according the procedures described above:

TABLE 18

Examples

| # | MOLSTRUCTURE | NAME |
|---|---|---|
| 186 | 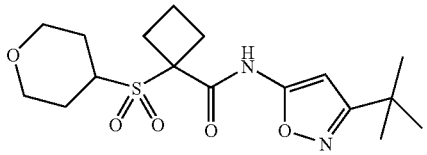 | 1-(Tetrahydro-pyran-4-sulfonyl)-cyclobutanecarboxylic acid (3-tert-butyl-isoxazol-5-yl)-amide |
| 187 | 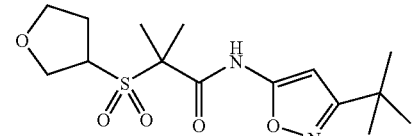 | N-(3-tert-Butyl-isoxazol-5-yl)-2-methyl-2-(tetrahydro-furan-3-sulfonyl)-propionamide |
| 188 | 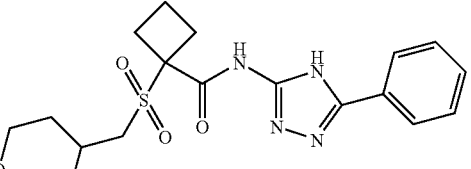 | 1-(Tetrahydro-pyran-4-ylmethanesulfonyl)-cyclobutanecarboxylic acid (5-phenyl-4H-1,2,4-triazol-3-yl)-amide |
| 189 | 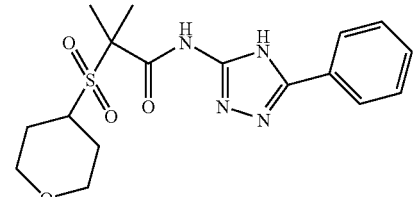 | 2-Methyl-N-(5-phenyl-4H-1,2,4-triazol-3-yl)-2-(tetrahydro-pyran-4-sulfonyl)-propionamide |
| 190 | 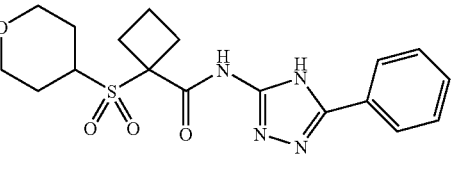 | 1-(Tetrahydro-pyran-4-sulfonyl)-cyclobutanecarboxylic acid (5-phenyl-4H-1,2,4-triazol-3-yl)-amide |
| 191 | 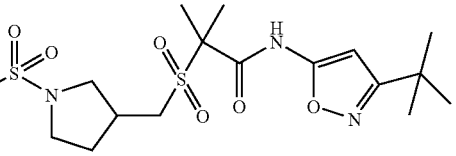 | N-(3-tert-Butyl-isoxazol-5-yl)-2-(1-methanesulfonyl-pyrrolidin-3-ylmethanesulfonyl)-2-methyl-propionamide |
| 192 | 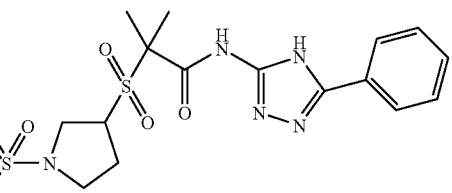 | 2-(1-Methanesulfonyl-pyrrolidine-3-sulfonyl)-2-methyl-N-(5-phenyl-4H-1,2,4-triazol-3-yl)-propionamide |

Assessment of Biological Properties

The biological properties of the compounds of the formula I were assessed using the assays described below.

A. Human CB1 and CB2 Receptor Binding:

Experimental Method:

CB2 membranes were purchased and made from HEK293 EBNA cells stably transfected with human CB2 receptor cDNA (Perkin Elmer Life and Analytical Sciences). CB1 membranes were isolated from HEK cells stably co-transfected with human CB1 receptor and Gα16 cDNA's. The membrane preparation was bound to scintillation beads (Ysi-Poly-L-lysine SPA beads, GE Healthcare) for 4 hours at room temperature in assay buffer containing 50 mM Tris, pH 7.5, 2.5 mM EDTA, 5 mM MgCl$_2$, 0.8% fatty acid free Bovine Serum Albumin. Unbound membrane was removed by washing in assay buffer. Membrane-bead mixture was added to 96-well assay plates in the amounts of 15 ug membrane per well (CB2) or 2.5 ug per well (CB1) and 1 mg SPA bead per well. Compounds were added to the membrane-bead mixture in dose-response concentrations ranging from $1\times10^{-5}$ M to $1\times10^{-10}$ M with 0.25% DMSO, final. The competition reaction was initiated with the addition of $^3$H-CP55940 (Perkin Elmer Life and Analytical Sciences) at a final concentration of 1.5 nM (CB2) or 2.5 nM (CB1). The reaction was incubated at room temperature for 18 hours and read on TopCount NXT plate reader. Total and non-specific binding was determined in the absence and presence of 1.25 uM Win 55212 (Sigma). IC50 values for each compound were calculated as the concentration of compound that inhibits the specific binding of the radioactively labeled ligand to the receptor by 50% using the XLFit 4.1 four parameter logistic model. IC50 values were converted to inhibition constant (Ki) values using Cheng-Prusoff equation.

B. CB2R Mediated Modulation of cAMP Synthesis:

Compounds of the invention were evaluated for their CB2 agonist or inverse agonistic activity in accordance with the following experimental method. Compounds which were shown to bind to CB2 by the binding assay described above but which were not shown to exhibit CB2R-mediated modulation of cAMP synthesis by this assay were presumed to be CB2 antagonists.

Experimental Method:

CHO cells expressing human CB2R (Euroscreen) were plated at a density of 5000 cells per well in 384 well plates and incubated overnight at 37° C. After removing the media, the cells were treated with test compounds diluted in stimulation buffer containing 1 mM IBMX, 0.25% BSA and 10 uM Forskolin. The assay was incubated for 30 minutes at 37° C. Cells were lysed and the cAMP concentration was measured using DiscoverX-XS cAMP kit, following the manufacturer's protocol. In this setting, agonists will decrease forskolin induced production of cAMP while inverse agonists will further increase forskolin induced production of cAMP. EC50 of agonists were calculated as follows. The maximal amount of cAMP produced by forskolin compared to the level of cAMP inhibited by 1 uM CP55940 is defined as 100%. The EC50 value of each test compound was determined as the concentration at which 50% of the forskolin-stimulated cAMP synthesis was inhibited. Data was analyzed using a four-parameter logistic model. (Model 205 of XLfit 4.0).

C. CB1R Mediated Modulation of cAMP Synthesis:

Compounds of the invention were evaluated for their CB1 agonist or inverse agonistic activity in accordance with the following experimental method. Compounds which were shown to bind to CB1 by the binding assay described above but which were not shown to exhibit CB1R-mediated modulation of cAMP synthesis by this assay were presumed to be CB1 antagonists.

Experimental Method:

CHO cells expressing human CB1R (Euroscreen) were plated at a density of 5000 cells per well in 384 well plates and incubated overnight at 37° C. After removing the media, the cells were treated with test compounds diluted in stimulation buffer containing 1 mM IBMX, 0.25% BSA and 10 uM Forskolin. The assay was incubated for 30 minutes at 37° C. Cells were lysed and the cAMP concentration was measured using DiscoverX-XS cAMP kit, following the manufacturer's protocol. In this setting, agonists will decrease forskolin induced production of cAMP while inverse agonists will further increase forskolin induced production of cAMP. EC50 of agonists were calculated as follows. The maximal amount of cAMP produced by forskolin compared to the level of cAMP inhibited by 1 uM CP55940 is defined as 100%. The EC50 value of each test compound was determined as the concentration at which 50% of the forskolin-stimulated cAMP synthesis was inhibited. Data was analyzed using a four-parameter logistic model. (Model 205 of XLfit 4.0).

| Compounds Having Agonist Activity | |
|---|---|
| NAME | CB2 $EC_{50}$ [nM] |
| N-(5-tert-Butyl-isoxazol-3-yl)-2-cyclohexanesulfonyl-2-methyl-propionamide | 0.2 |
| N-(5-tert-Butyl-4-methyl-thiazol-2-yl)-2-methyl-2-(propane-2-sulfonyl)-propionamide | 25.8 |
| 1-Cyclohexanesulfonyl-cyclobutanecarboxylic acid (5-tert-butyl-isoxazol-3-yl)-amide | 0.5 |
| 1-Cyclohexanesulfonyl-cyclobutanecarboxylic acid (4-tert-butyl-thiazol-2-yl)-amide | 11.7 |
| N-(5-tert-Butyl-4-methyl-thiazol-2-yl)-2-(4-chloro-phenylmethanesulfonyl)-2-methyl-propionamide | 12.1 |
| N-(5-tert-Butyl-isoxazol-3-yl)-2-(4-chloro-phenylmethanesulfonyl)-2-methyl-propionamide | 16.6 |
| N-(5-tert-Butyl-isoxazol-3-yl)-2-methyl-2-(propane-1-sulfonyl)-propionamide | 61.9 |
| N-(4-tert-Butyl-thiazol-2-yl)-2-methyl-2-(propane-1-sulfonyl)-propionamide | 19.2 |
| N-(4-tert-Butyl-thiazol-2-yl)-2-cyclopentanesulfonyl-2-methyl-propionamide | 19.0 |
| 2-Cyclohexanesulfonyl-2-methyl-N-(5-trifluoromethyl-pyridin-2-yl)-propionamide | 11.8 |
| N-(5-tert-Butyl-isoxazol-3-yl)-2-cyclopentanesulfonyl-2-methyl-propionamide | 2.4 |
| N-(4-tert-Butyl-thiazol-2-yl)-2-methyl-2-(2-methyl-propane-2-sulfonyl)-propionamide | 61.1 |
| N-(5-tert-Butyl-4-methyl-thiazol-2-yl)-2-methyl-2-(2-methyl-propane-2-sulfonyl)-propionamide | 10.7 |
| 2-(Butane-2-sulfonyl)-N-(5-tert-butyl-isoxazol-3-yl)-2-methyl-propionamide | 18.7 |
| 2-(Butane-2-sulfonyl)-N-(4-tert-butyl-thiazol-2-yl)-2-methyl-propionamide | 14.4 |
| N-(5-tert-Butyl-isoxazol-3-yl)-2-methyl-2-(2-methyl-propane-1-sulfonyl)-propionamide | 44.6 |
| N-(5-tert-Butyl-isoxazol-3-yl)-2-methyl-2-(tetrahydro-pyran-4-ylmethanesulfonyl)-propionamide | 4.5 |
| N-(4-tert-Butyl-thiazol-2-yl)-2-methyl-2-(tetrahydro-pyran-4-ylmethanesulfonyl)-propionamide | 23.0 |
| N-(5-tert-Butyl-4-methyl-thiazol-2-yl)-2-methyl-2-(tetrahydro-pyran-4-ylmethanesulfonyl)-propionamide | 0.2 |
| 2-Methyl-2-(tetrahydro-pyran-4-ylmethanesulfonyl)-N-(5-trifluoromethyl-pyridin-2-yl)-propionamide | 72.3 |
| N-(5-tert-Butyl-isoxazol-3-yl)-2-methyl-2-(tetrahydro-pyran-4-sulfonyl)-propionamide | 0.7 |
| N-(4-tert-Butyl-thiazol-2-yl)-2-methyl-2-(tetrahydro-pyran-4-sulfonyl)-propionamide | 12.4 |
| 2-Methyl-2-(tetrahydro-pyran-4-sulfonyl)-N-(5-trifluoromethyl-pyridin-2-yl)-propionamide | 62.4 |

-continued

Compounds Having Agonist Activity

| NAME | CB2 EC$_{50}$ [nM] |
|---|---|
| N-(5-tert-Butyl-4-methyl-thiazol-2-yl)-2-methyl-2-(tetrahydro-pyran-4-sulfonyl)-propionamide | 0.3 |
| N-[4-(4-Chloro-phenyl)-thiazol-2-yl]-2-cyclopentanesulfonyl-2-methyl-propionamide | 1.5 |
| N-(5-tert-Butyl-isoxazol-3-yl)-2-methyl-2-(tetrahydro-furan-2-ylmethanesulfonyl)-propionamide | 70.5 |
| N-(5-tert-Butyl-2-methyl-2H-pyrazol-3-yl)-2-cyclobutylmethanesulfonyl-2-methyl-propionamide | 33.0 |
| N-(3-tert-Butyl-isoxazol-5-yl)-2-cyclohexanesulfonyl-2-methyl-propionamide | 0.0 |
| N-(5-tert-Butyl-isoxazol-3-yl)-2-cyclohexylmethanesulfonyl-2-methyl-propionamide | 0.6 |
| N-(5-tert-Butyl-isoxazol-3-yl)-2-methyl-2-(tetrahydro-pyran-2-ylmethanesulfonyl)-propionamide | 0.2 |
| N-(5-tert-Butyl-2-methyl-2H-pyrazol-3-yl)-2-cycloheptanesulfonyl-2-methyl-propionamide | 6.5 |
| N-(5-tert-Butyl-2-methyl-2H-pyrazol-3-yl)-2-cyclohexylmethanesulfonyl-2-methyl-propionamide | 23.8 |
| 2-(3,3-Dimethyl-2-oxo-butane-1-sulfonyl)-2-methyl-N-(5-trifluoromethyl-pyridin-2-yl)-propionamide | 41.5 |
| N-(5-tert-Butyl-isoxazol-3-yl)-2-(3,3-dimethyl-2-oxo-butane-1-sulfonyl)-2-methyl-propionamide | 39.8 |
| N-(5-tert-Butyl-isoxazol-3-yl)-2-methyl-2-(3-methyl-butane-1-sulfonyl)-propionamide | 0.2 |
| N-(5-tert-Butyl-2-methyl-2H-pyrazol-3-yl)-2-methyl-2-(3-methyl-butane-1-sulfonyl)-propionamide | 15.4 |
| N-(5-tert-Butyl-isoxazol-3-yl)-2-cycloheptanesulfonyl-2-methyl-propionamide | 0.1 |
| 2-Cyclohexylmethanesulfonyl-2-methyl-N-(5-trifluoromethyl-pyridin-2-yl)-propionamide | 15.4 |
| 2-Methyl-2-(3-methyl-butane-1-sulfonyl)-N-(5-trifluoromethyl-pyridin-2-yl)-propionamide | 19.9 |
| N-(5-tert-Butyl-isoxazol-3-yl)-2-methyl-2-(4-methyl-tetrahydro-pyran-4-sulfonyl)-propionamide | 9.4 |
| 2-Cycloheptanesulfonyl-2-methyl-N-(5-trifluoromethyl-pyridin-2-yl)-propionamide | 7.1 |
| N-(5-tert-Butyl-isoxazol-3-yl)-2-cyclopropylmethanesulfonyl-2-methyl-propionamide | 34.3 |
| N-(5-tert-Butyl-isoxazol-3-yl)-2-cyclobutylmethanesulfonyl-2-methyl-propionamide | 3.4 |
| N-[4-(4-Chloro-phenyl)-thiazol-2-yl]-2-methyl-2-(propane-2-sulfonyl)-propionamide | 44.9 |
| N-(4-tert-Butyl-phenyl)-2-methyl-2-(propane-1-sulfonyl)-propionamide | 12.3 |
| N-[4-(4-Chloro-phenyl)-thiazol-2-yl]-2-methyl-2-(propane-1-sulfonyl)-propionamide | 13.0 |
| N-(3-tert-Butyl-isoxazol-5-yl)-2-methyl-2-(propane-1-sulfonyl)-propionamide | 89.7 |
| N-(5-tert-Butyl-isoxazol-3-yl)-2-(1-methanesulfonyl-pyrrolidin-3-ylmethanesulfonyl)-2-methyl-propionamide | 44.1 |
| 2-Methyl-N-(5-methyl-4-phenyl-thiazol-2-yl)-2-(propane-1-sulfonyl)-propionamide | 52.2 |
| N-(5-Ethyl-4-phenyl-thiazol-2-yl)-2-methyl-2-(propane-1-sulfonyl)-propionamide | 10.8 |
| N-(4-Cyclohexyl-thiazol-2-yl)-2-methyl-2-(propane-1-sulfonyl)-propionamide | 31.1 |
| N-(5-tert-Butyl-4-methyl-thiazol-2-yl)-2-methyl-2-(propane-1-sulfonyl)-propionamide | 7.2 |
| N-(3-tert-Butyl-phenyl)-2-methyl-2-(tetrahydro-pyran-4-ylmethanesulfonyl)-propionamide | 14.3 |
| N-Benzothiazol-2-yl-2-methyl-2-(tetrahydro-pyran-4-ylmethanesulfonyl)-propionamide | 27.9 |
| 2-Methyl-N-(4-phenyl-thiazol-2-yl)-2-(tetrahydro-pyran-4-ylmethanesulfonyl)-propionamide | 7.1 |
| 2-Methyl-N-(5-phenyl-[1,2,4]thiadiazol-3-yl)-2-(tetrahydro-pyran-4-ylmethanesulfonyl)-propionamide | 17.6 |
| 2-Methyl-N-(5-methyl-4-phenyl-thiazol-2-yl)-2-(tetrahydro-pyran-4-ylmethanesulfonyl)-propionamide | 2.5 |
| N-(5-Ethyl-4-phenyl-thiazol-2-yl)-2-methyl-2-(tetrahydro-pyran-4-ylmethanesulfonyl)-propionamide | 2.0 |
| N-(4-Cyclohexyl-thiazol-2-yl)-2-methyl-2-(tetrahydro-pyran-4-ylmethanesulfonyl)-propionamide | 8.3 |
| N-[3-(2,2-Dimethyl-propyl)-isoxazol-5-yl]-2-methyl-2-(tetrahydro-pyran-4-ylmethanesulfonyl)-propionamide | 74.3 |
| 2-Methyl-N-quinolin-3-yl-2-(tetrahydro-pyran-4-ylmethanesulfonyl)-propionamide | 86.0 |
| N-(4-tert-Butyl-phenyl)-2-methyl-2-(tetrahydro-pyran-4-ylmethanesulfonyl)-propionamide | 3.3 |
| 2-Methyl-N-quinolin-2-yl-2-(tetrahydro-pyran-4-ylmethanesulfonyl)-propionamide | 5.8 |
| N-[4-(4-Chloro-phenyl)-thiazol-2-yl]-2-methyl-2-(tetrahydro-pyran-4-ylmethanesulfonyl)-propionamide | 2.2 |
| N-Isoquinolin-3-yl-2-methyl-2-(tetrahydro-pyran-4-ylmethanesulfonyl)-propionamide | 99.1 |
| N-(3-tert-Butyl-isoxazol-5-yl)-2-methyl-2-(tetrahydro-pyran-4-ylmethanesulfonyl)-propionamide | 4.0 |
| N-(3-tert-Butyl-isoxazol-5-yl)-2-methyl-2-(tetrahydro-pyran-4-sulfonyl)-propionamide | 0.1 |
| N-(5-tert-Butyl-1,3,4-thiadiazol-2-yl)-2-cyclopentanesulfonyl-2-methyl-propionamide | 18.6 |
| 2-Cyclopentanesulfonyl-2-methyl-N-(5-phenyl-4H-1,2,4-triazol-3-yl)-propionamide | 3.8 |
| N-(3-tert-Butyl-isoxazol-5-yl)-2-cyclobutylmethanesulfonyl-2-methyl-propionamide | 3.7 |
| N-(3-tert-Butyl-isoxazol-5-yl)-2-cyclopropylmethanesulfonyl-2-methyl-propionamide | 12.5 |
| N-(3-tert-Butyl-isoxazol-5-yl)-2-methyl-2-(3-methyl-butane-1-sulfonyl)-propionamide | 0.04 |
| 2-Methyl-N-(5-phenyl-4H-1,2,4-triazol-3-yl)-2-(tetrahydro-pyran-4-ylmethanesulfonyl)-propionamide | 1.7 |

-continued

| Compounds Having Agonist Activity | |
|---|---|
| NAME | CB2 $EC_{50}$ [nM] |
| N-(3-tert-Butyl-isoxazol-5-yl)-2-cyclopentanesulfonyl-2-methyl-propionamide | 0.9 |
| N-(3-tert-Butyl-isoxazol-5-yl)-2-cyclohexylmethanesulfonyl-2-methyl-propionamide | 0.1 |
| 2-(Butane-2-sulfonyl)-N-(3-tert-butyl-isoxazol-5-yl)-2-methyl-propionamide | 3.3 |
| N-(3-tert-Butyl-isoxazol-5-yl)-2-methyl-2-(tetrahydro-pyran-2-ylmethanesulfonyl)-propionamide | 0.2 |
| N-(3-tert-Butyl-isoxazol-5-yl)-2-methyl-2-(2-methyl-propane-1-sulfonyl)-propionamide | 1.6 |
| 1-(Tetrahydro-pyran-4-ylmethanesulfonyl)-cyclobutanecarboxylic acid (3-tert-butyl-isoxazol-5-yl)-amide | 6.2 |
| N-(3-tert-Butyl-isoxazol-5-yl)-2-(4-fluoro-phenylmethanesulfonyl)-2-methyl-propionamide | 17.0 |
| N-(3-tert-Butyl-isoxazol-5-yl)-2-methyl-2-(tetrahydro-furan-2-ylmethanesulfonyl)-propionamide | 31.5 |
| N-(3-tert-Butyl-isoxazol-5-yl)-2-methyl-2-(tetrahydro-furan-3-ylmethanesulfonyl)-propionamide | 18.5 |
| N-(3-sec-Butyl-isoxazol-5-yl)-2-methyl-2-(tetrahydro-pyran-4-ylmethanesulfonyl)-propionamide | 20.0 |
| N-[4-(4-Fluoro-phenyl)-thiazol-2-yl]-2-methyl-2-(tetrahydro-pyran-4-ylmethanesulfonyl)-propionamide | 5.5 |

Through the use of the above described assays the following compounds were found to exhibit agonistic activity and thus to be particularly well suited for the treatment of pain as well as for the treatment of inflammation.

N-(5-tert-Butyl-isoxazol-3-yl)-2-cyclohexanesulfonyl-2-methyl-propionamide
N-(4-tert-Butyl-thiazol-2-yl)-2-methyl-2-(propane-2-sulfonyl)-propionamide
N-(5-tert-Butyl-4-methyl-thiazol-2-yl)-2-methyl-2-(propane-2-sulfonyl)-propionamide
1-Cyclohexanesulfonyl-cyclobutanecarboxylic acid (5-tert-butyl-isoxazol-3-yl)-amide
1-Cyclohexanesulfonyl-cyclobutanecarboxylic acid (4-tert-butyl-thiazol-2-yl)-amide
N-(5-tert-Butyl-isoxazol-3-yl)-2-methyl-2-(propane-2-sulfonyl)-propionamide
N-(4-tert-Butyl-thiazol-2-yl)-2-(4-chloro-phenylmethanesulfonyl)-2-methyl-propionamide
N-(5-tert-Butyl-4-methyl-thiazol-2-yl)-2-(4-chloro-phenylmethanesulfonyl)-2-methyl-propionamide
N-(5-tert-Butyl-isoxazol-3-yl)-2-(4-chloro-phenylmethanesulfonyl)-2-methyl-propionamide
N-(5-tert-Butyl-isoxazol-3-yl)-2-methyl-2-(propane-1-sulfonyl)-propionamide
2-Methyl-2-(propane-1-sulfonyl)-N-(4-trifluoromethyl-pyridin-2-yl)-propionamide
2-Methyl-N-naphthalen-2-yl-2-(propane-2-sulfonyl)-propionamide
2-Methyl-2-(propane-2-sulfonyl)-N-(4,5,6,7-tetrahydro-benzothiazol-2-yl)-propionamide
2-Methyl-N-(2-methyl-5-thiophen-2-yl-2H-pyrazol-3-yl)-2-(propane-2-sulfonyl)-propionamide
N-Isoquinolin-3-yl-2-methyl-2-(propane-2-sulfonyl)-propionamide
N-Benzothiazol-2-yl-2-methyl-2-(propane-2-sulfonyl)-propionamide
N-(4-tert-Butyl-thiazol-2-yl)-2-methyl-2-(propane-1-sulfonyl)-propionamide
2-Methyl-2-(propane-2-sulfonyl)-N-quinolin-3-yl-propionamide
N-(4-tert-Butyl-phenyl)-2-methyl-2-(propane-2-sulfonyl)-propionamide
2-Methyl-N-(4-phenyl-thiazol-2-yl)-2-(propane-2-sulfonyl)-propionamide
2-Methyl-N-(2-methyl-5-phenyl-2H-pyrazol-3-yl)-2-(propane-2-sulfonyl)-propionamide
N-(5-tert-Butyl-2-methyl-2H-pyrazol-3-yl)-2-methyl-2-(propane-2-sulfonyl)-propionamide
N-(3-tert-Butyl-phenyl)-2-methyl-2-(propane-2-sulfonyl)-propionamide
2-Methyl-2-(propane-2-sulfonyl)-N-(6-trifluoromethyl-pyridin-2-yl)-propionamide
N-(4-tert-Butyl-thiazol-2-yl)-2-cyclopentanesulfonyl-2-methyl-propionamide
2-Cyclohexanesulfonyl-2-methyl-N-(5-trifluoromethyl-pyridin-2-yl)-propionamide
N-(5-tert-Butyl-isoxazol-3-yl)-2-cyclopentanesulfonyl-2-methyl-propionamide
N-(5-tert-Butyl-isoxazol-3-yl)-2-cyclopropanesulfonyl-2-methyl-propionamide
N-(5-tert-Butyl-isoxazol-3-yl)-2-methyl-2-(2-methyl-propane-2-sulfonyl)-propionamide
N-(4-tert-Butyl-thiazol-2-yl)-2-methyl-2-(2-methyl-propane-2-sulfonyl)-propionamide
N-(5-tert-Butyl-4-methyl-thiazol-2-yl)-2-methyl-2-(2-methyl-propane-2-sulfonyl)-propionamide
N-(5-tert-Butyl-2-methyl-2H-pyrazol-3-yl)-2-methyl-2-(2-methyl-propane-2-sulfonyl)-propionamide
2-Methyl-2-(2-methyl-propane-2-sulfonyl)-N-(6-trifluoromethyl-pyridin-2-yl)-propionamide
2-Methyl-2-(2-methyl-propane-2-sulfonyl)-N-(4-trifluoromethyl-pyridin-2-yl)-propionamide
2-(1-Acetyl-piperidin-3-ylmethanesulfonyl)-N-(5-tert-butyl-isoxazol-3-yl)-2-methyl-propionamide
N-(5-tert-Butyl-isoxazol-3-yl)-3-methyl-2-(propane-2-sulfonyl)-butyramide
2-(Butane-2-sulfonyl)-N-(5-tert-butyl-isoxazol-3-yl)-2-methyl-propionamide
2-(Butane-2-sulfonyl)-N-(5-tert-butyl-2-methyl-2H-pyrazol-3-yl)-2-methyl-propionamide
2-(Butane-2-sulfonyl)-N-(4-tert-butyl-thiazol-2-yl)-2-methyl-propionamide
N-(4-tert-Butyl-thiazol-2-yl)-2-(propane-2-sulfonyl)-propionamide N-(4-tert-Butyl-thiazol-2-yl)-3-methyl-2-(propane-2-sulfonyl)-butyramide
N-(5-tert-Butyl-4-methyl-thiazol-2-yl)-3-methyl-2-(propane-2-sulfonyl)-butyramide
2-(Butane-2-sulfonyl)-2-methyl-N-(5-trifluoromethyl-pyridin-2-yl)-propionamide
N-(5-tert-Butyl-2-methyl-2H-pyrazol-3-yl)-2-ethanesulfonyl-2-methyl-propionamide
N-(5-tert-Butyl-2-methyl-2H-pyrazol-3-yl)-2-methanesulfonyl-2-methyl-propionamide
N-(4-tert-Butyl-thiazol-2-yl)-2-methanesulfonyl-2-methyl-propionamide
N-(5-tert-Butyl-isoxazol-3-yl)-2-methyl-2-(2-methyl-propane-1-sulfonyl)-propionamide
N-(5-tert-Butyl-isoxazol-3-yl)-2-methyl-2-(2,2,2-trifluoro-ethanesulfonyl)-propionamide
N-(5-tert-Butyl-isoxazol-3-yl)-2-methanesulfonyl-2-methyl-propionamide
N-(5-tert-Butyl-isoxazol-3-yl)-2-methyl-2-(tetrahydro-pyran-4-ylmethanesulfonyl)-propionamide
N-(4-tert-Butyl-thiazol-2-yl)-2-methyl-2-(tetrahydro-pyran-4-ylmethanesulfonyl)-propionamide
N-(5-tert-Butyl-4-methyl-thiazol-2-yl)-2-methyl-2-(tetrahydro-pyran-4-ylmethanesulfonyl)-propionamide
N-(5-tert-Butyl-2-methyl-2H-pyrazol-3-yl)-2-methyl-2-(tetrahydro-pyran-4-ylmethanesulfonyl)-propionamide
2-Methyl-2-(tetrahydro-pyran-4-ylmethanesulfonyl)-N-(5-trifluoromethyl-pyridin-2-yl)-propionamide
2-Methyl-2-(tetrahydro-pyran-4-ylmethanesulfonyl)-N-(6-trifluoromethyl-pyridin-2-yl)-propionamide
N-(5-tert-Butyl-2-methyl-2H-pyrazol-3-yl)-2-cyclopentanesulfonyl-2-methyl-propionamide
2-Cyclopentanesulfonyl-2-methyl-N-(2-methyl-5-phenyl-2H-pyrazol-3-yl)-propionamide
2-Cyclopentanesulfonyl-2-methyl-N-(5-trifluoromethyl-pyridin-2-yl)-propionamide
2-Cyclopentanesulfonyl-2-methyl-N-(4-trifluoromethyl-thiazol-2-yl)-propionamide
N-(5-tert-Butyl-isoxazol-3-yl)-2-methyl-2-(tetrahydro-pyran-4-sulfonyl)-propionamide
N-(4-tert-Butyl-thiazol-2-yl)-2-methyl-2-(tetrahydro-pyran-4-sulfonyl)-propionamide
2-Methyl-2-(tetrahydro-pyran-4-sulfonyl)-N-(5-trifluoromethyl-pyridin-2-yl)-propionamide
2-Methyl-N-(2-methyl-5-phenyl-2H-pyrazol-3-yl)-2-(tetrahydro-pyran-4-sulfonyl)-propionamide
N-(5-tert-Butyl-4-methyl-thiazol-2-yl)-2-methyl-2-(tetrahydro-pyran-4-sulfonyl)-propionamide
N-(5-tert-Butyl-2-methyl-2H-pyrazol-3-yl)-2-methyl-2-(tetrahydro-pyran-4-sulfonyl)-propionamide
N-[4-(4-Chloro-phenyl)-thiazol-2-yl]-2-cyclopentanesulfonyl-2-methyl-propionamide
2-Cyclopentanesulfonyl-2-methyl-N-(4-trifluoromethyl-pyridin-2-yl)-propionamide
N-(5-tert-Butyl-isoxazol-3-yl)-2-methyl-2-(tetrahydro-furan-2-ylmethanesulfonyl)-propionamide
N-(5-tert-Butyl-2-methyl-2H-pyrazol-3-yl)-2-cyclobutyl-methanesulfonyl-2-methyl-propionamide
N-(5-tert-Butyl-2-methyl-2H-pyrazol-3-yl)-2-(hexane-3-sulfonyl)-2-methyl-propionamide
N-(3-tert-Butyl-isoxazol-5-yl)-2-cyclohexanesulfonyl-2-methyl-propionamide
N-(5-tert-Butyl-2-methyl-2H-pyrazol-3-yl)-2-methyl-2-(tetrahydro-pyran-2-ylmethanesulfonyl)-propionamide
N-(5-tert-Butyl-isoxazol-3-yl)-2-cyclohexylmethanesulfonyl-2-methyl-propionamide
N-(5-tert-Butyl-isoxazol-3-yl)-2-ethanesulfonyl-2-methyl-propionamide
N-(5-tert-Butyl-isoxazol-3-yl)-2-cyanomethanesulfonyl-2-methyl-propionamide
N-(5-tert-Butyl-isoxazol-3-yl)-2-methyl-2-(tetrahydro-pyran-2-ylmethanesulfonyl)-propionamide
N-(5-tert-Butyl-2-methyl-2H-pyrazol-3-yl)-2-(2,2-dimethyl-propane-1-sulfonyl)-2-methyl-propionamide
N-(5-tert-Butyl-2-methyl-2H-pyrazol-3-yl)-2-cycloheptane-sulfonyl-2-methyl-propionamide
N-(5-tert-Butyl-2-methyl-2H-pyrazol-3-yl)-2-cyclohexyl-methanesulfonyl-2-methyl-propionamide
2-Methyl-2-(tetrahydro-furan-2-ylmethanesulfonyl)-N-(5-trifluoromethyl-pyridin-2-yl)-propionamide
2-Methyl-2-(tetrahydro-pyran-2-ylmethanesulfonyl)-N-(5-trifluoromethyl-pyridin-2-yl)-propionamide
2-(3,3-Dimethyl-2-oxo-butane-1-sulfonyl)-2-methyl-N-(5-trifluoromethyl-pyridin-2-yl)-propionamide
N-(5-tert-Butyl-isoxazol-3-yl)-2-(3,3-dimethyl-2-oxo-butane-1-sulfonyl)-2-methyl-propionamide
N-(5-tert-Butyl-2-methyl-2H-pyrazol-3-yl)-2-methyl-2-((S)-5-oxo-pyrrolidin-2-ylmethanesulfonyl)-propionamide
N-(5-tert-Butyl-2-methyl-2H-pyrazol-3-yl)-2-methyl-2-((R)-5-oxo-pyrrolidin-2-ylmethanesulfonyl)-propionamide
N-(5-tert-Butyl-isoxazol-3-yl)-2-methyl-2-(3-methyl-butane-1-sulfonyl)-propionamide
N-(5-tert-Butyl-2-methyl-2H-pyrazol-3-yl)-2-methyl-2-(3-methyl-butane-1-sulfonyl)-propionamide
N-(5-tert-Butyl-isoxazol-3-yl)-2-cycloheptanesulfonyl-2-methyl-propionamide
N-(5-tert-Butyl-isoxazol-3-yl)-2-methyl-2-(piperidin-4-ylmethanesulfonyl)-propionamide
2-Cyclohexylmethanesulfonyl-2-methyl-N-(5-trifluoromethyl-pyridin-2-yl)-propionamide
2-Methyl-2-(3-methyl-butane-1-sulfonyl)-N-(5-trifluoromethyl-pyridin-2-yl)-propionamide
2-Methyl-2-(piperidin-4-ylmethanesulfonyl)-N-(5-trifluoromethyl-pyridin-2-yl)-propionamide
N-(5-tert-Butyl-2-methyl-2H-pyrazol-3-yl)-2-methyl-2-(tetrahydro-furan-2-ylmethanesulfonyl)-propionamide
N-(5-tert-Butyl-isoxazol-3-yl)-2-methyl-2-(4-methyl-tetrahydro-pyran-4-sulfonyl)-propionamide
2-Cycloheptanesulfonyl-2-methyl-N-(5-trifluoromethyl-pyridin-2-yl)-propionamide
2-Cyclopropylmethanesulfonyl-2-methyl-N-(5-trifluoromethyl-pyridin-2-yl)-propionamide
2-Cyclobutylmethanesulfonyl-2-methyl-N-(5-trifluoromethyl-pyridin-2-yl)-propionamide
N-(5-tert-Butyl-isoxazol-3-yl)-2-cyclopropylmethanesulfonyl-2-methyl-propionamide
N-(5-tert-Butyl-isoxazol-3-yl)-2-cyclobutylmethanesulfonyl-2-methyl-propionamide
N-(5-tert-Butyl-isoxazol-3-yl)-2-methyl-2-(3-phenyl-propane-1-sulfonyl)-propionamide
N-(3-tert-Butyl-isoxazol-5-yl)-2-methyl-2-(propane-2-sulfonyl)-propionamide
N-[4-(4-Chloro-phenyl)-thiazol-2-yl]-2-methyl-2-(propane-2-sulfonyl)-propionamide
2-Methyl-2-(propane-2-sulfonyl)-N-(4-pyridin-3-yl-thiazol-2-yl)-propionamide
2-Methyl-2-(propane-2-sulfonyl)-N-(4-pyridin-2-yl-thiazol-2-yl)-propionamide
2-Methyl-2-(propane-2-sulfonyl)-N-(4-pyridin-4-yl-thiazol-2-yl)-propionamide 2-Methyl-2-(propane-2-sulfonyl)-N-quinolin-2-yl-propionamide
2-Methyl-2-(propane-1-sulfonyl)-N-quinolin-3-yl-propionamide
N-(4-tert-Butyl-phenyl)-2-methyl-2-(propane-1-sulfonyl)-propionamide
2-Methyl-2-(propane-1-sulfonyl)-N-(4,5,6,7-tetrahydro-benzothiazol-2-yl)-propionamide
2-Methyl-2-(propane-1-sulfonyl)-N-quinolin-2-yl-propionamide
N-[4-(4-Chloro-phenyl)-thiazol-2-yl]-2-methyl-2-(propane-1-sulfonyl)-propionamide
2-Methyl-N-(2-methyl-5-phenyl-2H-pyrazol-3-yl)-2-(propane-1-sulfonyl)-propionamide
N-(5-tert-Butyl-2-methyl-2H-pyrazol-3-yl)-2-methyl-2-(propane-1-sulfonyl)-propionamide
2-Methyl-N-(2-methyl-5-thiophen-2-yl-2H-pyrazol-3-yl)-2-(propane-1-sulfonyl)-propionamide
N-(3-tert-Butyl-phenyl)-2-methyl-2-(propane-1-sulfonyl)-propionamide
2-Methyl-2-(propane-1-sulfonyl)-N-(4-pyridin-4-yl-thiazol-2-yl)-propionamide
2-Methyl-2-(propane-1-sulfonyl)-N-(4-trifluoromethyl-thiazol-2-yl)-propionamide
N-(3-tert-Butyl-isoxazol-5-yl)-2-methyl-2-(propane-1-sulfonyl)-propionamide
N-Benzothiazol-2-yl-2-methyl-2-(propane-1-sulfonyl)-propionamide
2-Methyl-2-(propane-1-sulfonyl)-N-(5-trifluoromethyl-pyridin-2-yl)-propionamide
N-(5-tert-Butyl-isoxazol-3-yl)-2-(1-methanesulfonyl-pyrrolidin-3-ylmethanesulfonyl)-2-methyl-propionamide
2-Methyl-N-(5-methyl-4-phenyl-thiazol-2-yl)-2-(propane-1-sulfonyl)-propionamide
N-(5-Ethyl-4-phenyl-thiazol-2-yl)-2-methyl-2-(propane-1-sulfonyl)-propionamide
2-Methyl-N-(5-phenyl-pyridin-2-yl)-2-(propane-1-sulfonyl)-propionamide
N-(4-Cyclohexyl-thiazol-2-yl)-2-methyl-2-(propane-1-sulfonyl)-propionamide
N-(5-tert-Butyl-4-methyl-thiazol-2-yl)-2-methyl-2-(propane-1-sulfonyl)-propionamide
N-(2,4-Dimethyl-5-phenyl-2H-pyrazol-3-yl)-2-methyl-2-(propane-1-sulfonyl)-propionamide
N-[3-(2,2-Dimethyl-propyl)-isoxazol-5-yl]-2-methyl-2-(propane-1-sulfonyl)-propionamide
N-(3-tert-Butyl-phenyl)-2-methyl-2-(tetrahydro-pyran-4-ylmethanesulfonyl)-propionamide
2-Methyl-2-(tetrahydro-pyran-4-ylmethanesulfonyl)-N-(4-trifluoromethyl-thiazol-2-yl)-propionamide
N-(4-Cyclopropyl-thiazol-2-yl)-2-methyl-2-(tetrahydro-pyran-4-ylmethanesulfonyl)-propionamide
N-Benzothiazol-2-yl-2-methyl-2-(tetrahydro-pyran-4-ylmethanesulfonyl)-propionamide
2-Methyl-N-(4-phenyl-thiazol-2-yl)-2-(tetrahydro-pyran-4-ylmethanesulfonyl)-propionamide
N-(5-tert-Butyl-[1,3,4]thiadiazol-2-yl)-2-methyl-2-(tetrahydro-pyran-4-ylmethanesulfonyl)-propionamide
2-Methyl-2-(tetrahydro-pyran-4-ylmethanesulfonyl)-N-(4-trifluoromethyl-pyridin-2-yl)-propionamide
N-(4-Ethyl-pyridin-2-yl)-2-methyl-2-(tetrahydro-pyran-4-ylmethanesulfonyl)-propionamide
2-Methyl-N-(5-phenyl-[1,2,4]thiadiazol-3-yl)-2-(tetrahydro-pyran-4-ylmethanesulfonyl)-propionamide
N-Benzooxazol-2-yl-2-methyl-2-(tetrahydro-pyran-4-ylmethanesulfonyl)-propionamide
2-Methyl-N-(5-methyl-4-phenyl-thiazol-2-yl)-2-(tetrahydro-pyran-4-ylmethanesulfonyl)-propionamide
N-(5-Ethyl-4-phenyl-thiazol-2-yl)-2-methyl-2-(tetrahydro-pyran-4-ylmethanesulfonyl)-propionamide
N-(4-Cyclohexyl-thiazol-2-yl)-2-methyl-2-(tetrahydro-pyran-4-ylmethanesulfonyl)-propionamide
2-Methyl-N-(3-propyl-isoxazol-5-yl)-2-(tetrahydro-pyran-4-ylmethanesulfonyl)-propionamide
N-(5-Isopropyl-2-methyl-2H-pyrazol-3-yl)-2-methyl-2-(tetrahydro-pyran-4-ylmethanesulfonyl)-propionamide
N-(2,4-Dimethyl-5-phenyl-2H-pyrazol-3-yl)-2-methyl-2-(tetrahydro-pyran-4-ylmethanesulfonyl)-propionamide
N-[3-(2,2-Dimethyl-propyl)-isoxazol-5-yl]-2-methyl-2-(tetrahydro-pyran-4-ylmethanesulfonyl)-propionamide
2-Methyl-N-naphthalen-1-yl-2-(tetrahydro-pyran-4-ylmethanesulfonyl)-propionamide
2-Methyl-N-(5-methyl-pyridin-2-yl)-2-(tetrahydro-pyran-4-ylmethanesulfonyl)-propionamide
2-Methyl-N-quinolin-3-yl-2-(tetrahydro-pyran-4-ylmethanesulfonyl)-propionamide
2-Methyl-2-(tetrahydro-pyran-4-ylmethanesulfonyl)-N-(3-trifluoromethyl-phenyl)-propionamide
N-(4-tert-Butyl-phenyl)-2-methyl-2-(tetrahydro-pyran-4-ylmethanesulfonyl)-propionamide
2-Methyl-N-quinolin-2-yl-2-(tetrahydro-pyran-4-ylmethanesulfonyl)-propionamide
N-[4-(4-Chloro-phenyl)-thiazol-2-yl]-2-methyl-2-(tetrahydro-pyran-4-ylmethanesulfonyl)-propionamide
2-Methyl-2-(tetrahydro-pyran-4-ylmethanesulfonyl)-N-(4-trifluoromethyl-phenyl)-propionamide
2-Methyl-N-(2-methyl-5-phenyl-2H-pyrazol-3-yl)-2-(tetrahydro-pyran-4-ylmethanesulfonyl)-propionamide
N-Isoquinolin-3-yl-2-methyl-2-(tetrahydro-pyran-4-ylmethanesulfonyl)-propionamide
N-(3-tert-Butyl-isoxazol-5-yl)-2-methyl-2-(tetrahydro-pyran-4-ylmethanesulfonyl)-propionamide
N-(3-tert-Butyl-isoxazol-5-yl)-2-methyl-2-(tetrahydro-pyran-4-sulfonyl)-propionamide
N-(5-tert-Butyl-1,3,4-thiadiazol-2-yl)-2-cyclopentanesulfonyl-2-methyl-propionamide
2-Cyclopentanesulfonyl-2-methyl-N-(5-phenyl-4H-1,2,4-triazol-3-yl)-propionamide
N-(3-tert-Butyl-isoxazol-5-yl)-2-cyclobutylmethanesulfonyl-2-methyl-propionamide
N-(3-tert-Butyl-isoxazol-5-yl)-2-cyclopropylmethanesulfonyl-2-methyl-propionamide
N-(3-tert-Butyl-isoxazol-5-yl)-2-methyl-2-(3-methyl-butane-1-sulfonyl)-propionamide
2-Methyl-N-(5-phenyl-4H-1,2,4-triazol-3-yl)-2-(tetrahydro-pyran-4-ylmethanesulfonyl)-propionamide
N-(3-tert-Butyl-isoxazol-5-yl)-2-cyclopentanesulfonyl-2-methyl-propionamide
N-(3-tert-Butyl-isoxazol-5-yl)-2-cyclohexylmethanesulfonyl-2-methyl-propionamide
2-(Butane-2-sulfonyl)-N-(3-tert-butyl-isoxazol-5-yl)-2-methyl-propionamide
N-(3-tert-Butyl-isoxazol-5-yl)-2-methyl-2-(tetrahydro-pyran-2-ylmethanesulfonyl)-propionamide
N-(3-tert-Butyl-isoxazol-5-yl)-2-methyl-2-(2-methyl-propane-1-sulfonyl)-propionamide
1-(Tetrahydro-pyran-4-ylmethanesulfonyl)-cyclobutanecarboxylic acid (3-tert-butyl-isoxazol-5-yl)-amide
N-(3-tert-Butyl-isoxazol-5-yl)-2-(4-fluoro-phenylmethanesulfonyl)-2-methyl-propionamide
N-(3-tert-Butyl-isoxazol-5-yl)-2-methyl-2-(tetrahydro-furan-2-ylmethanesulfonyl)-propionamide N-(3-tert-Butyl-isoxazol-5-yl)-2-methyl-2-(tetrahydro-furan-3-ylmethanesulfonyl)-propionamide
N-(3-sec-Butyl-isoxazol-5-yl)-2-methyl-2-(tetrahydro-pyran-4-ylmethanesulfonyl)-propionamide
N-[4-(4-Fluoro-phenyl)-thiazol-2-yl]-2-methyl-2-(tetrahydro-pyran-4-ylmethanesulfonyl)-propionamide
2-Methyl-N-(4-pyridin-3-yl-thiazol-2-yl)-2-(tetrahydro-pyran-4-ylmethanesulfonyl)-propionamide
2-Methyl-N-(4-pyridin-2-yl-thiazol-2-yl)-2-(tetrahydro-pyran-4-ylmethanesulfonyl)-propionamide
2-Methyl-N-(4-pyridin-4-yl-thiazol-2-yl)-2-(tetrahydro-pyran-4-ylmethanesulfonyl)-propionamide
N-(3-Isopropyl-isoxazol-5-yl)-2-methyl-2-(tetrahydro-pyran-4-ylmethanesulfonyl)-propionamide
2-Methyl-N-(3-phenyl-1,2,4-thiadiazol-5-yl)-2-(tetrahydro-pyran-4-ylmethanesulfonyl)-propionamide Of the above compounds, the following are preferred:

N-(5-tert-Butyl-isoxazol-3-yl)-2-cyclohexanesulfonyl-2-methyl-propionamide
N-(4-tert-Butyl-thiazol-2-yl)-2-methyl-2-(propane-2-sulfonyl)-propionamide
N-(5-tert-Butyl-4-methyl-thiazol-2-yl)-2-methyl-2-(propane-2-sulfonyl)-propionamide
1-Cyclohexanesulfonyl-cyclobutanecarboxylic acid (5-tert-butyl-isoxazol-3-yl)-amide
N-(5-tert-Butyl-isoxazol-3-yl)-2-methyl-2-(propane-2-sulfonyl)-propionamide
N-(4-tert-Butyl-thiazol-2-yl)-2-(4-chloro-phenylmethanesulfonyl)-2-methyl-propionamide
N-(5-tert-Butyl-4-methyl-thiazol-2-yl)-2-(4-chloro-phenylmethanesulfonyl)-2-methyl-propionamide
N-(5-tert-Butyl-isoxazol-3-yl)-2-(4-chloro-phenylmethanesulfonyl)-2-methyl-propionamide
N-(5-tert-Butyl-isoxazol-3-yl)-2-methyl-2-(propane-1-sulfonyl)-propionamide
N-(4-tert-Butyl-thiazol-2-yl)-2-methyl-2-(propane-1-sulfonyl)-propionamide
N-(4-tert-Butyl-phenyl)-2-methyl-2-(propane-2-sulfonyl)-propionamide
N-(3-tert-Butyl-phenyl)-2-methyl-2-(propane-2-sulfonyl)-propionamide
N-(4-tert-Butyl-thiazol-2-yl)-2-cyclopentanesulfonyl-2-methyl-propionamide
2-Cyclohexanesulfonyl-2-methyl-N-(5-trifluoromethyl-pyridin-2-yl)-propionamide
N-(5-tert-Butyl-isoxazol-3-yl)-2-cyclopentanesulfonyl-2-methyl-propionamide
N-(5-tert-Butyl-isoxazol-3-yl)-2-cyclopropanesulfonyl-2-methyl-propionamide
N-(5-tert-Butyl-isoxazol-3-yl)-2-methyl-2-(2-methyl-propane-2-sulfonyl)-propionamide
N-(4-tert-Butyl-thiazol-2-yl)-2-methyl-2-(2-methyl-propane-2-sulfonyl)-propionamide
N-(5-tert-Butyl-4-methyl-thiazol-2-yl)-2-methyl-2-(2-methyl-propane-2-sulfonyl)-propionamide
2-(Butane-2-sulfonyl)-N-(5-tert-butyl-isoxazol-3-yl)-2-methyl-propionamide
2-(Butane-2-sulfonyl)-N-(4-tert-butyl-thiazol-2-yl)-2-methyl-propionamide
N-(4-tert-Butyl-thiazol-2-yl)-3-methyl-2-(propane-2-sulfonyl)-butyramide
N-(5-tert-Butyl-4-methyl-thiazol-2-yl)-3-methyl-2-(propane-2-sulfonyl)-butyramide
N-(5-tert-Butyl-isoxazol-3-yl)-2-methyl-2-(2-methyl-propane-1-sulfonyl)-propionamide
N-(5-tert-Butyl-isoxazol-3-yl)-2-methyl-2-(tetrahydro-pyran-4-ylmethanesulfonyl)-propionamide
N-(4-tert-Butyl-thiazol-2-yl)-2-methyl-2-(tetrahydro-pyran-4-ylmethanesulfonyl)-propionamide
N-(5-tert-Butyl-4-methyl-thiazol-2-yl)-2-methyl-2-(tetrahydro-pyran-4-ylmethanesulfonyl)-propionamide
N-(5-tert-Butyl-2-methyl-2H-pyrazol-3-yl)-2-methyl-2-(tetrahydro-pyran-4-ylmethanesulfonyl)-propionamide
2-Methyl-2-(tetrahydro-pyran-4-ylmethanesulfonyl)-N-(5-trifluoromethyl-pyridin-2-yl)-propionamide
2-Methyl-2-(tetrahydro-pyran-4-ylmethanesulfonyl)-N-(6-trifluoromethyl-pyridin-2-yl)-propionamide
2-Cyclopentanesulfonyl-2-methyl-N-(5-trifluoromethyl-pyridin-2-yl)-propionamide
N-(5-tert-Butyl-isoxazol-3-yl)-2-methyl-2-(tetrahydro-pyran-4-sulfonyl)-propionamide
N-(4-tert-Butyl-thiazol-2-yl)-2-methyl-2-(tetrahydro-pyran-4-sulfonyl)-propionamide
2-Methyl-2-(tetrahydro-pyran-4-sulfonyl)-N-(5-trifluoromethyl-pyridin-2-yl)-propionamide
N-(5-tert-Butyl-4-methyl-thiazol-2-yl)-2-methyl-2-(tetrahydro-pyran-4-sulfonyl)-propionamide
N-(5-tert-Butyl-2-methyl-2H-pyrazol-3-yl)-2-methyl-2-(tetrahydro-pyran-4-sulfonyl)-propionamide
N-[4-(4-Chloro-phenyl)-thiazol-2-yl]-2-cyclopentanesulfonyl-2-methyl-propionamide
2-Cyclopentanesulfonyl-2-methyl-N-(4-trifluoromethyl-pyridin-2-yl)-propionamide
N-(5-tert-Butyl-isoxazol-3-yl)-2-methyl-2-(tetrahydro-furan-2-ylmethanesulfonyl)-propionamide
N-(5-tert-Butyl-2-methyl-2H-pyrazol-3-yl)-2-cyclobutylmethanesulfonyl-2-methyl-propionamide
N-(5-tert-Butyl-2-methyl-2H-pyrazol-3-yl)-2-(hexane-3-sulfonyl)-2-methyl-propionamide
N-(3-tert-Butyl-isoxazol-5-yl)-2-cyclohexanesulfonyl-2-methyl-propionamide
N-(5-tert-Butyl-isoxazol-3-yl)-2-cyclohexylmethanesulfonyl-2-methyl-propionamide
N-(5-tert-Butyl-isoxazol-3-yl)-2-methyl-2-(tetrahydro-pyran-2-ylmethanesulfonyl)-propionamide
N-(5-tert-Butyl-2-methyl-2H-pyrazol-3-yl)-2-cycloheptanesulfonyl-2-methyl-propionamide
N-(5-tert-Butyl-2-methyl-2H-pyrazol-3-yl)-2-cyclohexylmethanesulfonyl-2-methyl-propionamide
2-Methyl-2-(tetrahydro-pyran-2-ylmethanesulfonyl)-N-(5-trifluoromethyl-pyridin-2-yl)-propionamide
2-(3,3-Dimethyl-2-oxo-butane-1-sulfonyl)-2-methyl-N-(5-trifluoromethyl-pyridin-2-yl)-propionamide
N-(5-tert-Butyl-isoxazol-3-yl)-2-(3,3-dimethyl-2-oxo-butane-1-sulfonyl)-2-methyl-propionamide
N-(5-tert-Butyl-isoxazol-3-yl)-2-methyl-2-(3-methyl-butane-1-sulfonyl)-propionamide
N-(5-tert-Butyl-2-methyl-2H-pyrazol-3-yl)-2-methyl-2-(3-methyl-butane-1-sulfonyl)-propionamide
N-(5-tert-Butyl-isoxazol-3-yl)-2-cycloheptanesulfonyl-2-methyl-propionamide
2-Cyclohexylmethanesulfonyl-2-methyl-N-(5-trifluoromethyl-pyridin-2-yl)-propionamide
2-Methyl-2-(3-methyl-butane-1-sulfonyl)-N-(5-trifluoromethyl-pyridin-2-yl)-propionamide
2-Cycloheptanesulfonyl-2-methyl-N-(5-trifluoromethyl-pyridin-2-yl)-propionamide
2-Cyclopropylmethanesulfonyl-2-methyl-N-(5-trifluoromethyl-pyridin-2-yl)-propionamide
2-Cyclobutylmethanesulfonyl-2-methyl-N-(5-trifluoromethyl-pyridin-2-yl)-propionamide
N-(5-tert-Butyl-isoxazol-3-yl)-2-cyclopropylmethanesulfonyl-2-methyl-propionamide N-(5-tert-Butyl-isoxazol-3-yl)-2-cyclobutylmethanesulfonyl-2-methyl-propionamide
N-(3-tert-Butyl-isoxazol-5-yl)-2-methyl-2-(propane-2-sulfonyl)-propionamide
N-[4-(4-Chloro-phenyl)-thiazol-2-yl]-2-methyl-2-(propane-2-sulfonyl)-propionamide
2-Methyl-2-(propane-2-sulfonyl)-N-quinolin-2-yl-propionamide
2-Methyl-2-(propane-1-sulfonyl)-N-quinolin-3-yl-propionamide
N-(4-tert-Butyl-phenyl)-2-methyl-2-(propane-1-sulfonyl)-propionamide
2-Methyl-2-(propane-1-sulfonyl)-N-quinolin-2-yl-propionamide
N-[4-(4-Chloro-phenyl)-thiazol-2-yl]-2-methyl-2-(propane-1-sulfonyl)-propionamide
N-(3-tert-Butyl-phenyl)-2-methyl-2-(propane-1-sulfonyl)-propionamide
N-(3-tert-Butyl-isoxazol-5-yl)-2-methyl-2-(propane-1-sulfonyl)-propionamide
N-Benzothiazol-2-yl-2-methyl-2-(propane-1-sulfonyl)-propionamide
N-(5-tert-Butyl-isoxazol-3-yl)-2-(1-methanesulfonyl-pyrrolidin-3-ylmethanesulfonyl)-2-methyl-propionamide
2-Methyl-N-(5-methyl-4-phenyl-thiazol-2-yl)-2-(propane-1-sulfonyl)-propionamide
N-(5-Ethyl-4-phenyl-thiazol-2-yl)-2-methyl-2-(propane-1-sulfonyl)-propionamide
N-(4-Cyclohexyl-thiazol-2-yl)-2-methyl-2-(propane-1-sulfonyl)-propionamide
N-(5-tert-Butyl-4-methyl-thiazol-2-yl)-2-methyl-2-(propane-1-sulfonyl)-propionamide
N-[3-(2,2-Dimethyl-propyl)-isoxazol-5-yl]-2-methyl-2-(propane-1-sulfonyl)-propionamide
N-Benzothiazol-2-yl-2-methyl-2-(tetrahydro-pyran-4-ylmethanesulfonyl)-propionamide
2-Methyl-N-(4-phenyl-thiazol-2-yl)-2-(tetrahydro-pyran-4-ylmethanesulfonyl)-propionamide
N-(5-tert-Butyl-[1,3,4]thiadiazol-2-yl)-2-methyl-2-(tetrahydro-pyran-4-ylmethanesulfonyl)-propionamide
2-Methyl-N-(5-phenyl-[1,2,4]thiadiazol-3-yl)-2-(tetrahydro-pyran-4-ylmethanesulfonyl)-propionamide
2-Methyl-N-(5-methyl-4-phenyl-thiazol-2-yl)-2-(tetrahydro-pyran-4-ylmethanesulfonyl)-propionamide
N-(5-Ethyl-4-phenyl-thiazol-2-yl)-2-methyl-2-(tetrahydro-pyran-4-ylmethanesulfonyl)-propionamide
N-(4-Cyclohexyl-thiazol-2-yl)-2-methyl-2-(tetrahydro-pyran-4-ylmethanesulfonyl)-propionamide
2-Methyl-N-(3-propyl-isoxazol-5-yl)-2-(tetrahydro-pyran-4-ylmethanesulfonyl)-propionamide
N-[3-(2,2-Dimethyl-propyl)-isoxazol-5-yl]-2-methyl-2-(tetrahydro-pyran-4-ylmethanesulfonyl)-propionamide
2-Methyl-N-quinolin-3-yl-2-(tetrahydro-pyran-4-ylmethanesulfonyl)-propionamide
2-Methyl-2-(tetrahydro-pyran-4-ylmethanesulfonyl)-N-(3-trifluoromethyl-phenyl)-propionamide
N-(4-tert-Butyl-phenyl)-2-methyl-2-(tetrahydro-pyran-4-ylmethanesulfonyl)-propionamide
2-Methyl-N-quinolin-2-yl-2-(tetrahydro-pyran-4-ylmethanesulfonyl)-propionamide
N-[4-(4-Chloro-phenyl)-thiazol-2-yl]-2-methyl-2-(tetrahydro-pyran-4-ylmethanesulfonyl)-propionamide
2-Methyl-2-(tetrahydro-pyran-4-ylmethanesulfonyl)-N-(4-trifluoromethyl-phenyl)-propionamide
N-(3-tert-Butyl-isoxazol-5-yl)-2-methyl-2-(tetrahydro-pyran-4-ylmethanesulfonyl)-propionamide
N-(3-tert-Butyl-isoxazol-5-yl)-2-methyl-2-(tetrahydro-pyran-4-sulfonyl)-propionamide
N-(5-tert-Butyl-1,3,4-thiadiazol-2-yl)-2-cyclopentanesulfonyl-2-methyl-propionamide
2-Cyclopentanesulfonyl-2-methyl-N-(5-phenyl-4H-1,2,4-triazol-3-yl)-propionamide
N-(3-tert-Butyl-isoxazol-5-yl)-2-cyclobutylmethanesulfonyl-2-methyl-propionamide
N-(3-tert-Butyl-isoxazol-5-yl)-2-cyclopropylmethanesulfonyl-2-methyl-propionamide
N-(3-tert-Butyl-isoxazol-5-yl)-2-methyl-2-(3-methyl-butane-1-sulfonyl)-propionamide
2-Methyl-N-(5-phenyl-4H-1,2,4-triazol-3-yl)-2-(tetrahydro-pyran-4-ylmethanesulfonyl)-propionamide
N-(3-tert-Butyl-isoxazol-5-yl)-2-cyclopentanesulfonyl-2-methyl-propionamide
N-(3-tert-Butyl-isoxazol-5-yl)-2-cyclohexylmethanesulfonyl-2-methyl-propionamide
2-(Butane-2-sulfonyl)-N-(3-tert-butyl-isoxazol-5-yl)-2-methyl-propionamide
N-(3-tert-Butyl-isoxazol-5-yl)-2-methyl-2-(tetrahydro-pyran-2-ylmethanesulfonyl)-propionamide
N-(3-tert-Butyl-isoxazol-5-yl)-2-methyl-2-(2-methyl-propane-1-sulfonyl)-propionamide
1-(Tetrahydro-pyran-4-ylmethanesulfonyl)-cyclobutanecarboxylic acid (3-tert-butyl-isoxazol-5-yl)-amide
N-(3-tert-Butyl-isoxazol-5-yl)-2-(4-fluoro-phenylmethanesulfonyl)-2-methyl-propionamide
N-(3-tert-Butyl-isoxazol-5-yl)-2-methyl-2-(tetrahydro-furan-2-ylmethanesulfonyl)-propionamide
N-(3-tert-Butyl-isoxazol-5-yl)-2-methyl-2-(tetrahydro-furan-3-ylmethanesulfonyl)-propionamide
N-(3-sec-Butyl-isoxazol-5-yl)-2-methyl-2-(tetrahydro-pyran-4-ylmethanesulfonyl)-propionamide
N-[4-(4-Fluoro-phenyl)-thiazol-2-yl]-2-methyl-2-(tetrahydro-pyran-4-ylmethanesulfonyl)-propionamide
2-Methyl-N-(4-pyridin-3-yl-thiazol-2-yl)-2-(tetrahydro-pyran-4-ylmethanesulfonyl)-propionamide
2-Methyl-N-(4-pyridin-2-yl-thiazol-2-yl)-2-(tetrahydro-pyran-4-ylmethanesulfonyl)-propionamide
2-Methyl-N-(4-pyridin-4-yl-thiazol-2-yl)-2-(tetrahydro-pyran-4-ylmethanesulfonyl)-propionamide Of the above compounds, the following are most preferred:
N-(5-tert-Butyl-isoxazol-3-yl)-2-cyclohexanesulfonyl-2-methyl-propionamide
N-(5-tert-Butyl-4-methyl-thiazol-2-yl)-2-methyl-2-(propane-2-sulfonyl)-propionamide
1-Cyclohexanesulfonyl-cyclobutanecarboxylic acid (5-tert-butyl-isoxazol-3-yl)-amide
N-(5-tert-Butyl-4-methyl-thiazol-2-yl)-2-(4-chloro-phenylmethanesulfonyl)-2-methyl-propionamide
N-(5-tert-Butyl-isoxazol-3-yl)-2-(4-chloro-phenylmethanesulfonyl)-2-methyl-propionamide
N-(5-tert-Butyl-isoxazol-3-yl)-2-methyl-2-(propane-1-sulfonyl)-propionamide
N-(4-tert-Butyl-thiazol-2-yl)-2-methyl-2-(propane-1-sulfonyl)-propionamide
2-Cyclohexanesulfonyl-2-methyl-N-(5-trifluoromethyl-pyridin-2-yl)-propionamide
N-(5-tert-Butyl-isoxazol-3-yl)-2-cyclopentanesulfonyl-2-methyl-propionamide
N-(4-tert-Butyl-thiazol-2-yl)-2-methyl-2-(2-methyl-propane-2-sulfonyl)-propionamide
N-(5-tert-Butyl-4-methyl-thiazol-2-yl)-2-methyl-2-(2-methyl-propane-2-sulfonyl)-propionamide
2-(Butane-2-sulfonyl)-N-(5-tert-butyl-isoxazol-3-yl)-2-methyl-propionamide 2-(Butane-2-sulfonyl)-N-(4-tert-butyl-thiazol-2-yl)-2-methyl-propionamide
N-(5-tert-Butyl-isoxazol-3-yl)-2-methyl-2-(2-methyl-propane-1-sulfonyl)-propionamide
N-(5-tert-Butyl-isoxazol-3-yl)-2-methyl-2-(tetrahydro-pyran-4-ylmethanesulfonyl)-propionamide
N-(4-tert-Butyl-thiazol-2-yl)-2-methyl-2-(tetrahydro-pyran-4-ylmethanesulfonyl)-propionamide
N-(5-tert-Butyl-4-methyl-thiazol-2-yl)-2-methyl-2-(tetrahydro-pyran-4-ylmethanesulfonyl)-propionamide
2-Methyl-2-(tetrahydro-pyran-4-ylmethanesulfonyl)-N-(5-trifluoromethyl-pyridin-2-yl)-propionamide
N-(5-tert-Butyl-isoxazol-3-yl)-2-methyl-2-(tetrahydro-pyran-4-sulfonyl)-propionamide
N-(4-tert-Butyl-thiazol-2-yl)-2-methyl-2-(tetrahydro-pyran-4-sulfonyl)-propionamide
2-Methyl-2-(tetrahydro-pyran-4-sulfonyl)-N-(5-trifluoromethyl-pyridin-2-yl)-propionamide
N-(5-tert-Butyl-4-methyl-thiazol-2-yl)-2-methyl-2-(tetrahydro-pyran-4-sulfonyl)-propionamide
N-[4-(4-Chloro-phenyl)-thiazol-2-yl]-2-cyclopentanesulfonyl-2-methyl-propionamide
N-(5-tert-Butyl-isoxazol-3-yl)-2-methyl-2-(tetrahydro-furan-2-ylmethanesulfonyl)-propionamide
N-(5-tert-Butyl-2-methyl-2H-pyrazol-3-yl)-2-cyclobutylmethanesulfonyl-2-methyl-propionamide
N-(3-tert-Butyl-isoxazol-5-yl)-2-cyclohexanesulfonyl-2-methyl-propionamide
N-(5-tert-Butyl-isoxazol-3-yl)-2-cyclohexylmethanesulfonyl-2-methyl-propionamide
N-(5-tert-Butyl-isoxazol-3-yl)-2-methyl-2-(tetrahydro-pyran-2-ylmethanesulfonyl)-propionamide
N-(5-tert-Butyl-2-methyl-2H-pyrazol-3-yl)-2-cycloheptanesulfonyl-2-methyl-propionamide
N-(5-tert-Butyl-2-methyl-2H-pyrazol-3-yl)-2-cyclohexylmethanesulfonyl-2-methyl-propionamide
2-(3,3-Dimethyl-2-oxo-butane-1-sulfonyl)-2-methyl-N-(5-trifluoromethyl-pyridin-2-yl)-propionamide
N-(5-tert-Butyl-isoxazol-3-yl)-2-(3,3-dimethyl-2-oxo-butane-1-sulfonyl)-2-methyl-propionamide
N-(5-tert-Butyl-isoxazol-3-yl)-2-methyl-2-(3-methyl-butane-1-sulfonyl)-propionamide
N-(5-tert-Butyl-2-methyl-2H-pyrazol-3-yl)-2-methyl-2-(3-methyl-butane-1-sulfonyl)-propionamide
N-(5-tert-Butyl-isoxazol-3-yl)-2-cycloheptanesulfonyl-2-methyl-propionamide
2-Cyclohexylmethanesulfonyl-2-methyl-N-(5-trifluoromethyl-pyridin-2-yl)-propionamide
2-Methyl-2-(3-methyl-butane-1-sulfonyl)-N-(5-trifluoromethyl-pyridin-2-yl)-propionamide
2-Cycloheptanesulfonyl-2-methyl-N-(5-trifluoromethyl-pyridin-2-yl)-propionamide
N-(5-tert-Butyl-isoxazol-3-yl)-2-cyclopropylmethanesulfonyl-2-methyl-propionamide
N-(5-tert-Butyl-isoxazol-3-yl)-2-cyclobutylmethanesulfonyl-2-methyl-propionamide
N-[4-(4-Chloro-phenyl)-thiazol-2-yl]-2-methyl-2-(propane-2-sulfonyl)-propionamide
N-(4-tert-Butyl-phenyl)-2-methyl-2-(propane-1-sulfonyl)-propionamide
N-[4-(4-Chloro-phenyl)-thiazol-2-yl]-2-methyl-2-(propane-1-sulfonyl)-propionamide
N-(3-tert-Butyl-isoxazol-5-yl)-2-methyl-2-(propane-1-sulfonyl)-propionamide
N-(5-tert-Butyl-isoxazol-3-yl)-2-(1-methanesulfonyl-pyrrolidin-3-ylmethanesulfonyl)-2-methyl-propionamide 2-Methyl-N-(5-methyl-4-phenyl-thiazol-2-yl)-2-(propane-1-sulfonyl)-propionamide
N-(5-Ethyl-4-phenyl-thiazol-2-yl)-2-methyl-2-(propane-1-sulfonyl)-propionamide
N-(4-Cyclohexyl-thiazol-2-yl)-2-methyl-2-(propane-1-sulfonyl)-propionamide
N-(5-tert-Butyl-4-methyl-thiazol-2-yl)-2-methyl-2-(propane-1-sulfonyl)-propionamide
N-Benzothiazol-2-yl-2-methyl-2-(tetrahydro-pyran-4-ylmethanesulfonyl)-propionamide
2-Methyl-N-(5-phenyl-[1,2,4]thiadiazol-3-yl)-2-(tetrahydro-pyran-4-ylmethanesulfonyl)-propionamide
2-Methyl-N-(5-methyl-4-phenyl-thiazol-2-yl)-2-(tetrahydro-pyran-4-ylmethanesulfonyl)-propionamide
N-(5-Ethyl-4-phenyl-thiazol-2-yl)-2-methyl-2-(tetrahydro-pyran-4-ylmethanesulfonyl)-propionamide
N-[3-(2,2-Dimethyl-propyl)-isoxazol-5-yl]-2-methyl-2-(tetrahydro-pyran-4-ylmethanesulfonyl)-propionamide
2-Methyl-N-quinolin-3-yl-2-(tetrahydro-pyran-4-ylmethanesulfonyl)-propionamide
N-(4-tert-Butyl-phenyl)-2-methyl-2-(tetrahydro-pyran-4-ylmethanesulfonyl)-propionamide
2-Methyl-N-quinolin-2-yl-2-(tetrahydro-pyran-4-ylmethanesulfonyl)-propionamide
N-[4-(4-Chloro-phenyl)-thiazol-2-yl]-2-methyl-2-(tetrahydro-pyran-4-ylmethanesulfonyl)-propionamide
N-(3-tert-Butyl-isoxazol-5-yl)-2-methyl-2-(tetrahydro-pyran-4-ylmethanesulfonyl)-propionamide
N-(3-tert-Butyl-isoxazol-5-yl)-2-methyl-2-(tetrahydro-pyran-4-sulfonyl)-propionamide
N-(5-tert-Butyl-1,3,4-thiadiazol-2-yl)-2-cyclopentanesulfonyl-2-methyl-propionamide
2-Cyclopentanesulfonyl-2-methyl-N-(5-phenyl-4H-1,2,4-triazol-3-yl)-propionamide
N-(3-tert-Butyl-isoxazol-5-yl)-2-cyclobutylmethanesulfonyl-2-methyl-propionamide
N-(3-tert-Butyl-isoxazol-5-yl)-2-cyclopropylmethanesulfonyl-2-methyl-propionamide
N-(3-tert-Butyl-isoxazol-5-yl)-2-methyl-2-(3-methyl-butane-1-sulfonyl)-propionamide
2-Methyl-N-(5-phenyl-4H-1,2,4-triazol-3-yl)-2-(tetrahydro-pyran-4-ylmethanesulfonyl)-propionamide
N-(3-tert-Butyl-isoxazol-5-yl)-2-cyclopentanesulfonyl-2-methyl-propionamide
N-(3-tert-Butyl-isoxazol-5-yl)-2-cyclohexylmethanesulfonyl-2-methyl-propionamide
2-(Butane-2-sulfonyl)-N-(3-tert-butyl-isoxazol-5-yl)-2-methyl-propionamide
N-(3-tert-Butyl-isoxazol-5-yl)-2-methyl-2-(tetrahydro-pyran-2-ylmethanesulfonyl)-propionamide
N-(3-tert-Butyl-isoxazol-5-yl)-2-methyl-2-(2-methyl-propane-1-sulfonyl)-propionamide
1-(Tetrahydro-pyran-4-ylmethanesulfonyl)-cyclobutanecarboxylic acid (3-tert-butyl-isoxazol-5-yl)-amide
N-(3-tert-Butyl-isoxazol-5-yl)-2-(4-fluoro-phenylmethanesulfonyl)-2-methyl-propionamide
N-(3-tert-Butyl-isoxazol-5-yl)-2-methyl-2-(tetrahydro-furan-2-ylmethanesulfonyl)-propionamide
N-(3-tert-Butyl-isoxazol-5-yl)-2-methyl-2-(tetrahydro-furan-3-ylmethanesulfonyl)-propionamide
N-(3-sec-Butyl-isoxazol-5-yl)-2-methyl-2-(tetrahydro-pyran-4-ylmethanesulfonyl)-propionamide
N-[4-(4-Fluoro-phenyl)-thiazol-2-yl]-2-methyl-2-(tetrahydro-pyran-4-ylmethanesulfonyl)-propionamide Therapeutic Use As can be demonstrated by the assays described above, the compounds of the invention are useful in modulating the CB2 receptor function. By virtue of this fact, these compounds have therapeutic use in treating disease-states and conditions mediated by the CB2 receptor function or that would benefit from modulation of the CB2 receptor function.

As the compounds of the invention modulate the CB2 receptor function, they have very useful anti-inflammatory and immune-suppressive activity and they can be used in patients as drugs, particularly in the form of pharmaceutical compositions as set forth below, for the treatment of disease-states and conditions.

As noted before, those compounds which are CB2 agonists can also be employed for the treatment of pain.

The agonist, antagonist and inverse agonist compounds according to the invention can be used in patients as drugs for the treatment of the following disease-states or indications that are accompanied by inflammatory processes:

(i) Lung diseases: e.g. asthma, bronchitis, allergic rhinitis, emphysema, adult respiratory distress syndrome (ARDS), pigeon fancier's disease, farmer's lung, chronic obstructive pulmonary disease (COPD), asthma including allergic asthma (atopic or non-atopic) as well as exercise-induced bronchoconstriction, occupational asthma, viral- or bacterial exacerbation of asthma, other non-allergic asthmas and "wheezy-infant syndrome", pneumoconiosis, including aluminosis, anthracosis, asbestosis, chalicosis, ptilosis, siderosis, silicosis, tabacosis and byssinosis;

(ii) Rheumatic diseases or autoimmune diseases or musculoskeletal diseases: all forms of rheumatic diseases, especially rheumatoid arthritis, acute rheumatic fever, and polymyalgia rheumatica; reactive arthritis; rheumatic soft tissue diseases; inflammatory soft tissue diseases of other genesis; arthritic symptoms in degenerative joint diseases (arthroses); tendinitis, bursitis, osteoarthritis, traumatic arthritis; collagenoses of any genesis, e.g., systemic lupus erythematosus, scleroderma, polymyositis, dermatomyositis, Sjögren syndrome, Still disease, Felty syndrome; and osteoporosis and other bone resorption diseases;

(iii) Allergic diseases: all forms of allergic reactions, e.g., angioneurotic edema, hay fever, insect bites, allergic reactions to drugs, blood derivatives, contrast agents, etc., anaphylactic shock (anaphylaxis), urticaria, angioneurotic edema, and contact dermatitis;

(iv) Vascular diseases: panarteritis nodosa, polyarteritis nodosa, periarteritis nodosa, arteritis temporalis, Wegner granulomatosis, giant cell arthritis, atherosclerosis, reperfusion injury and erythema nodosum;

(v) Dermatological diseases: e.g. dermatitis, psoriasis; sunburn, burns, eczema;

(vi) Renal diseases: e.g. nephrotic syndrome; and all types of nephritis, e.g., glomerulonephritis; pancreatits;

(vii) Hepatic diseases: e.g. acute liver cell disintegration; acute hepatitis of various genesis, e.g., viral, toxic, drug-induced; and chronically aggressive and/or chronically intermittent hepatitis;

(viii) Gastrointestinal diseases: e.g. inflammatory bowel diseases, irritable bowel syndrome, regional enteritis (Crohns disease), colitis ulcerosa; gastritis; aphthous ulcer, celiac disease, regional ileitis, gastroesophageal reflux disease;

(ix) Neuroprotection: e.g. in the treatment of neurodegeneration following stroke; cardiac arrest; pulmonary bypass; traumatic brain injury; spinal cord injury or the like;

(x) Eye diseases: allergic keratitis, uveitis, or iritis; conjunctivitis; blepharitis; neuritis nervi optici; choroiditis; glaucoma and sympathetic ophthalmia;

(xi) Diseases of the ear, nose, and throat (ENT) area: e.g. tinnitus; allergic rhinitis or hay fever; otitis externa; caused by contact eczema, infection, etc.; and otitis media;

(xii) Neurological diseases: e.g. brain edema, particularly tumor-related brain edema; multiple sclerosis; acute encephalomyelitis; meningitis; acute spinal cord injury; trauma; dementia, particularly degenerative dementia (including senile dementia, Alzheimer's disease; Parkinson's disease and Creutzfeldt-Jacob disease; Huntington's chorea, Pick's disease; motor neuron disease), vascular dementia (including multi-infarct dementia) as well as dementia associated with intracranial space occupying lesions; infections and related conditions (including HIV infection); Guillain-Barre syndrome; myasthenia gravis, stroke; and various forms of seizures, e.g., nodding spasms;

(xiii) Blood diseases: acquired hemolytic anemia; aplastic anemia, and idiopathic thrombocytopenia;

(xiv) Tumor diseases: acute lymphatic leukemia; Hodgkin's disease, malignant lymphoma; lymphogranulomatoses; lymphosarcoma; solid malignant tumors; extensive metastases;

(xv) Endocrine diseases: endocrine opthalmopathy; endocrine orbitopathia; thyrotoxic crisis; Thyroiditis de Quervain; Hashimoto thyroiditis; Morbus Basedow; granulomatous thyroiditis; struma lymphomatosa; and Graves disease; type I diabetes (insulin-dependent diabetes);

(xvi) Organ and tissue transplantations and graft-versus-host diseases;

(xvii) Severe states of shock, e.g., septic shock, anaphylactic shock, and systemic inflammatory response syndrome (SIRS);

(xviii) Acute pain such as dental pain, perioperative, postoperative pain, traumatic pain, muscle pain, pain in burned skin, sun burn, trigeminal neuralgia, sun burn; spasm of the gastrointestinal tract or uterus, colics;

(xix) Visceral pain such as pain associated with chronic pelvic pain, pancreatitis, peptic ulcer, interstitial cystitis, renal colic, angina, dysmenorrhoea, menstruation, gynaecological pain, irritable bowel syndrome (IBS), non-ulcer dyspepsia, non-cardiac chest pain, myocardial ischemia;

(xx) Neuropathic pain such as low back pain, non-herpetic neuralgia, post herpetic neuralgia, diabetic neuropathy, nerve injury, acquired immune deficiency syndrome (AIDS) related neuropathic pain, head trauma, painful traumatic mononeuropathy, toxin and chemotherapy induced pain, phantom limb pain, painful polyneuropathy, thalamic pain syndrome, post-stroke pain, central nervous system injury, post surgical pain, stump pain, repetitive motion pain, pain induced by post mastectomy syndrome, multiple sclerosis, root avulsions, postthoracotomy syndrome, neuropathic pain associated hyperalgesia and allodynia.

(xxi) Inflammatory/nociceptive pain induced by or associated with disorders such as osteoarthritis, rheumatoid arthritis, rheumatic disease, teno-synovitis, gout, vulvodynia, myofascial pain (muscular injury, fibromyalgia), tendonitis, osteoarthritis, juvenile arthritis, spondylitis, gouty arthritis, psoriatic arthritis, muscoskeletal pain, fibromyalgia, sprains and strains, sympathetically maintained pain, myositis, pain associated with migraine, toothache, influenza and other viral infections such as the common cold, rheumatic fever, systemic lupus erythematosus;
(xxii) Cancer pain induced by or associated with tumors such as lymphatic leukemia; Hodgkin's disease, malignant lymphoma; lymphogranulomatoses; lymphosarcoma; solid malignant tumors; extensive metastases;
(xxiii) Headache such as cluster headache, migraine with and without aura, tension type headache, headache with different origins, headache disorders including prophylactic and acute use;
(xxiv) various other disease-states or conditions including, restenosis following percutaneous transluminal coronary angioplasty, acute and chronic pain, atherosclerosis, reperfusion injury, congestive heart failure, myocardial infarction, thermal injury, multiple organ injury secondary to trauma, necrotizing enterocolitis and syndromes associated with hemodialysis, leukopheresis, and granulocyte transfusion, sarcoidosis, gingivitis, pyrexia. edema resulting from trauma associated with burns, sprains or fracture, cerebral oedema and angioedema, Diabetes such as diabetic vasculopathy, diabetic neuropathy, diabetic retinopathy, post capillary resistance or diabetic symptoms associated with insulitis (e.g. hypergiycemia, diuresis, proteinuria and increased nitrite and kallikrein urinary excretion).

Other indications include: epilepsy, septic shock e.g. as antihypovolemic and/or antihypotensive agents, cancer, sepsis, osteoporosis, benign prostatic hyperplasia and hyperactive bladder, pruritis, vitiligo, general gastrointestinal disorders, disturbances of visceral motility at respiratory, genitourinary, gastrointestinal or vascular regions, wounds, burns, tissue damage and postoperative fever, syndromes associated with Itching.

Besides being useful for human treatment, these compounds are also useful for veterinary treatment of companion animals, exotic animals and farm animals, including mammals, rodents, and the like.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

Combination Therapy

These compounds may also be employed in combination therapies with the following compounds:
non-steroidal antiinflammatory drugs (NSAIDs) including COX-2 inhibitors such as propionic acid derivatives (alminoprofen, benoxaprofen, bucloxic acid, carprofen, fenhufen, fenoprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (meclofenamic acid, mefe-namic acid, and tolfenamic acid), biphenyl-carboxylic acid derivatives, oxicams (isoxicam, meloxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone), and the coxibs (celecoxib, valecoXID, rofecoxib and etoricoxib);
opiate receptor agonists such as morphine, propoxyphene (Darvon), tramadol, buprenorphin;
sodium channel blockers such as carbamazepine, mexiletine, lamotrigine, pregabaline, tectin, NW-1029, CGX-1002;
N-type calcium channel blockers such as Ziconotide, NMED-160, SPI-860; serotonergic and noradrenergic modulators such as SR-57746, paroxetine, duloxetine, clonidine, amitriptyline, citalopram;
corticosteroids such as betamethasone, budesonide, cortisone, dexamethasone, hydrocortisone, methylprednisolone, prednisolone, prednisone and triamcinolone;
histamine H1 receptor antagonists such as bromopheniramine, chlorpheniramine, dexchlorpheniramine, triprolidine, clemastine, diphenhydramine, diphenylpyraline, tripelennamine, hydroxyzine, methdiazine, promethazine, trimeprazine, azatadine, cyproheptadine, antazoline, pheniramine pyrilamine, astemizole, terfenadine, loratadine, cetirizine, desloratadine, fexofenadine and levocetirizine;
histamine H2 receptor antagonists such as cimetidine, famotidine and ranitidine;
proton pump inhibitors such as omeprazole, pantoprazole and esomeprazole;
leukotriene antagonists and 5-lipoxygenase inhibitors such as zafirlukast, montelukast, pranlukast and zileuton;
local anesthetics such as ambroxol, lidocaine;
VR1 agonists and antagonists such as NGX-4010, WL-1002, ALGRX-4975, WL-10001, AMG-517;
nicotinic acetylcholine receptor agonists such as ABT-202, A-366833, ABT-594; BTG-102, A-85380, CGX1204;
P2X3 receptor antagonists such as A-317491, ISIS-13920, AZD-9056;
NGF agonists and antagonists such as RI-724, RI-1024, AMG-819, AMG-403, PPH 207;
NK1 and NK2 antagonists such as DA-5018, R-116301; CP-728663, ZD-2249;
NMDA antagonist such as NER-MD-11, CNS-5161, EAA-090, AZ-756, CNP-3381; potassium channel modulators such as CL-888, ICA-69673, retigabine;
GABA modulators such as lacosamide;
serotonergic and noradrenergic modulators such as SR-57746, paroxetine, duloxetine, clonidine, amitriptyline, citalopram, flibanserin; and
combination with anti-migraine drugs like sumatriptan, zolmitriptan, naratriptan, eletriptan.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased inhibitory activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by *Remington: The Science and Practice of Pharmacy*, 20th Edition, A. Gennaro (ed.), Lippincott Williams & Wilkins, 2000; *Handbook of Pharmaceutical Additives*, Michael & Irene Ash (eds.), Gower, 1995; *Handbook of Pharmaceutical Excipients*, A. H. Kibbe (ed.), American Pharmaceutical Ass'n, 2000; H. C. Ansel and N. G. Popovish, *Pharmaceutical Dosage Forms and Drug Delivery Systems*, 5th ed., Lea and Febiger, 1990; each of which is incorporated herein by reference in their entireties to better describe the state of the art.

As one of skill in the art would expect, the forms of the compounds of the invention utilized in a particular pharmaceutical formulation will be selected (e.g., salts) that possess suitable physical characteristics (e.g., water solubility) that is required for the formulation to be efficacious.

Pharmaceutical compositions suitable for buccal (sub-lingual) administration include lozenges comprising a compound of the present invention in a flavored base, usually sucrose, and acacia or tragacanth, and pastilles comprising the compound in an inert base such as gelatin and glycerin or sucrose and acacia.

Pharmaceutical compositions suitable for parenteral administration comprise sterile aqueous preparations of a compound of the present invention. These preparations are preferably administered intravenously, although administration can also be effected by means of subcutaneous, intramuscular, or intradermal injection. Injectable pharmaceutical formulations are commonly based upon injectable sterile saline, phosphate-buffered saline, oleaginous suspensions, or other injectable carriers known in the art and are generally rendered sterile and isotonic with the blood. The injectable pharmaceutical formulations may therefore be provided as a sterile injectable solution or suspension in a nontoxic parenterally acceptable diluent or solvent, including 1,3-butanediol, water, Ringer's solution, isotonic sodium chloride solution, fixed oils such as synthetic mono- or diglycerides, fatty acids such as oleic acid, and the like. Such injectable pharmaceutical formulations are formulated according to the known art using suitable dispersing or setting agents and suspending agents. Injectable compositions will generally contain from 0.1 to 5% w/w of a compound of the invention.

Solid dosage forms for oral administration of the compounds include capsules, tablets, pills, powders, and granules. For such oral administration, a pharmaceutically acceptable composition containing a compound(s) of the invention is formed by the incorporation of any of the normally employed excipients, such as, for example, pharmaceutical grades of mannitol, lactose, starch, pregelatinized starch, magnesium stearate, sodium saccharine, talcum, cellulose ether derivatives, glucose, gelatin, sucrose, citrate, propyl gallate, and the like. Such solid pharmaceutical formulations may include formulations, as are well-known in the art, to provide prolonged or sustained delivery of the drug to the gastrointestinal tract by any number of mechanisms, which include, but are not limited to, pH sensitive release from the dosage form based on the changing pH of the small intestine, slow erosion of a tablet or capsule, retention in the stomach based on the physical properties of the formulation, bioadhesion of the dosage form to the mucosal lining of the intestinal tract, or enzymatic release of the active drug from the dosage form.

Liquid dosage forms for oral administration of the compounds include emulsions, microemulsions, solutions, suspensions, syrups, and elixirs, optionally containing pharmaceutical adjuvants in a carrier, such as, for example, water, saline, aqueous dextrose, glycerol, ethanol and the like. These compositions can also contain additional adjuvants such as wetting, emulsifying, suspending, sweetening, flavoring, and perfuming agents.

Topical dosage forms of the compounds include ointments, pastes, creams, lotions, gels, powders, solutions, sprays, inhalants, eye ointments, eye or ear drops, impregnated dressings and aerosols, and may contain appropriate conventional additives such as preservatives, solvents to assist drug penetration and emollients in ointments and creams. Topical application may be once or more than once per day depending upon the usual medical considerations. Furthermore, preferred compounds for the present invention can be administered in intranasal form via topical use of suitable intranasal vehicles. The formulations may also contain compatible conventional carriers, such as cream or ointment bases and ethanol or oleyl alcohol for lotions. Such carriers may be present as from about 1% up to about 98% of the formulation, more usually they will form up to about 80% of the formulation.

Transdermal administration is also possible. Pharmaceutical compositions suitable for transdermal administration can be presented as discrete patches adapted to remain in intimate contact with the epidermis of the recipient for a prolonged period of time. To be administered in the form of a transdermal delivery system, the dosage administration will, of course, be continuous rather than intermittent throughout the dosage regimen. Such patches suitably contain a compound of the invention in an optionally buffered, aqueous solution, dissolved and/or dispersed in an adhesive, or dispersed in a polymer. A suitable concentration of the active compound is about 1% to 35%, preferably about 3% to 15%.

For administration by inhalation, the compounds of the invention are conveniently delivered in the form of an aerosol spray from a pump spray device not requiring a propellant gas or from a pressurized pack or a nebulizer with the use of a suitable propellant, e.g., dichlorodifluoromethane, trichlorofluoromethane, dichlorotetrafluoroethane, tetrafluoroethane, heptafluoropropane, carbon dioxide, or other suitable gas. In any case, the aerosol spray dosage unit may be determined by providing a valve to deliver a metered amount so that the resulting metered dose inhaler (MDI) is used to administer the compounds of the invention in a reproducible and controlled way. Such inhaler, nebulizer, or atomizer devices are known in the prior art, for example, in PCT International Publication Nos. WO 97/12687 (particularly FIG. 6 thereof, which is the basis for the commercial RESPIMAT® nebulizer); WO 94/07607; WO 97/12683; and WO 97/20590, to which reference is hereby made and each of which is incorporated herein by reference in their entireties.

Rectal administration can be effected utilizing unit dose suppositories in which the compound is admixed with low-melting water-soluble or insoluble solids such as fats, cocoa butter, glycerinated gelatin, hydrogenated vegetable oils, mixtures of polyethylene glycols of various molecular weights, or fatty acid esters of polyethylene glycols, or the like. The active compound is usually a minor component, often from about 0.05 to 10% by weight, with the remainder being the base component.

In all of the above pharmaceutical compositions, the compounds of the invention are formulated with an acceptable carrier or excipient. The carriers or excipients used must, of course, be acceptable in the sense of being compatible with the other ingredients of the composition and must not be deleterious to the patient. The carrier or excipient can be a solid or a liquid, or both, and is preferably formulated with the compound of the invention as a unit-dose composition, for example, a tablet, which can contain from 0.05% to 95% by weight of the active compound. Such carriers or excipients include inert fillers or diluents, binders, lubricants, disintegrating agents, solution retardants, resorption accelerators, absorption agents, and coloring agents. Suitable binders include starch, gelatin, natural sugars such as glucose or β-lactose, corn sweeteners, natural and synthetic gums such as acacia, tragacanth or sodium alginate, carboxymethylcellulose, polyethylene glycol, waxes, and the like. Lubricants include sodium oleate, sodium stearate, magnesium stearate, sodium benzoate, sodium acetate, sodium chloride, and the like. Disintegrators include starch, methyl cellulose, agar, bentonite, xanthan gum, and the like.

Pharmaceutically acceptable carriers and excipients encompass all the foregoing additives and the like.

Examples of Pharmaceutical Formulations

| A. TABLETS | |
|---|---|
| Component | Amount per tablet (mg) |
| active substance | 100 |
| lactose | 140 |
| corn starch | 240 |
| polyvinylpyrrolidone | 15 |
| magnesium stearate | 5 |
| TOTAL | 500 |

The finely ground active substance, lactose, and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B. TABLETS | |
|---|---|
| Component | Amount per tablet (mg) |
| active substance | 80 |
| lactose | 55 |
| corn starch | 190 |
| polyvinylpyrrolidone | 15 |
| magnesium stearate | 2 |
| microcrystalline cellulose | 35 |
| sodium-carboxymethyl starch | 23 |
| TOTAL | 400 |

The finely ground active substance, some of the corn starch, lactose, microcrystalline cellulose, and polyvinylpyrrolidone are mixed together, the mixture is screened and worked with the remaining corn starch and water to form a granulate which is dried and screened. The sodium-carboxymethyl starch and the magnesium stearate are added and mixed in and the mixture is compressed to form tablets of a suitable size.

| C. COATED TABLETS | |
|---|---|
| Component | Amount per tablet (mg) |
| active substance | 5 |
| lactose | 30 |
| corn starch | 41.5 |
| polyvinylpyrrolidone | 3 |
| magnesium stearate | 0.5 |
| TOTAL | 90 |

The active substance, corn starch, lactose, and polyvinylpyrrolidone are thoroughly mixed and moistened with water. The moist mass is pushed through a screen with a 1 mm mesh size, dried at about 45° C. and the granules are then passed through the same screen. After the magnesium stearate has been mixed in, convex tablet cores with a diameter of 6 mm are compressed in a tablet-making machine. The tablet cores thus produced are coated in known manner with a covering consisting essentially of sugar and talc. The finished coated tablets are polished with wax.

| D. CAPSULES | |
|---|---|
| Component | Amount per capsule (mg) |
| active substance | 50 |
| corn starch | 268.5 |
| magnesium stearate | 1.5 |
| TOTAL | 320 |

The substance and corn starch are mixed and moistened with water. The moist mass is screened and dried. The dry granules are screened and mixed with magnesium stearate. The finished mixture is packed into size 1 hard gelatine capsules.

| E. AMPOULE SOLUTION | |
|---|---|
| Component | Amount per ampoule |
| active substance | 50 mg |
| sodium chloride | 50 mg |
| water for inj. | 5 mL |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilized and sealed by fusion. The ampoules contain 5 mg, 25 mg, and 50 mg of active substance.

F. SUPPOSITORIES

| Component | Amount per suppository (mg) |
|---|---|
| active substance | 50 |
| solid fat | 1650 |
| TOTAL | 1700 |

The hard fat is melted. At 40° C., the ground active substance is homogeneously dispersed therein. The mixture is cooled to 38° C. and poured into slightly chilled suppository molds.

G. METERING AEROSOL

| Component | Amount |
|---|---|
| active substance | 0.005 |
| sorbitan trioleate | 0.1 |
| Monofluorotrichloromethane and difluorodichloromethane (2:3) | To 100 |

The suspension is transferred into a conventional aerosol container with a metering valve. Preferably, 50 µL of suspension are delivered per spray. The active substance may also be metered in higher doses if desired (e.g., 0.02% by weight).

H. POWDER FOR INHALATION

| Component | Amount |
|---|---|
| active substance | 1.0 mg |
| lactose monohydrate | to 25 mg |

I. POWDER FOR INHALATION

| Component | Amount |
|---|---|
| active substance | 2.0 mg |
| lactose monohydrate | to 25 mg |

J. POWDER FOR INHALATION

| Component | Amount |
|---|---|
| active substance | 1.0 mg |
| lactose monohydrate | to 5 mg |

K. POWDER FOR INHALATION

| Component | Amount |
|---|---|
| active substance | 2.0 mg |
| lactose monohydrate | to 5 mg |

In Examples H, I, J, and K, the powder for inhalation is produced in the usual way by mixing the individual ingredients together.

What is claimed is:

1. A compound of the formula (I):

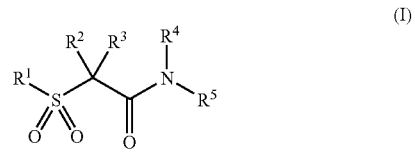

wherein
$R^1$ is methyl, ethyl, propyl, butyl, pentyl, hexyl, heptyl, octyl, nonyl, decyl, cyclopropyl, cyclobutyl, cyclopentyl, cyclohexyl, cycloheptyl, cyclooctyl, bicylco(3.3.0)octanyl, bicyclo[4.3.0]nonyl, benzyl or phenethyl each optionally independently substituted with 1 to 3 substituents chosen from methyl, ethyl, cyclopropyl, cyclobutyl, cyclopentyl, cyclohexyl, cyano, fluoro, chloro and bromo;

$R^2$ and $R^3$ are independently hydrogen, methyl, ethyl, n-propyl, isopropyl, isobutyl, tert-butyl, wherein $R^2$ and $R^3$ cannot simultaneously be hydrogen, or $R^2$ and $R^3$ together with the carbon to which they are attached form a cyclopropyl, cyclobutyl, cyclopentyl, cyclohexyl or tetrahydropyranyl ring;

$R^4$ is hydrogen;

$R^5$ is phenyl, naphthyl, pyridinyl, quinolinyl, isoquinolinyl, pyrrolyl, pyrazolyl, imidazolyl, oxazolyl, isoxazolyl, thiazolyl, isothiazolyl, triazolyl, oxadiazolyl, thiadiazolyl, indolyl, benzoxazolyl, benzopyrazolyl, benzoisoxazolyl, benzothiazolyl, benzoisothiazolyl, benzimidazolyl, tetrahydrobenzoxazolyl, tetrahydrobenzothiazolyl or tetrahydrobenzimidazolyl each optionally independently substituted with 1 to 3 substituents chosen from $C_1$-$C_6$ alkyl optionally substituted with 1 to 3 halogen atoms, $C_3$-$C_6$ cycloalkyl, halogen, cyano, dimethylamino$C_1$-$C_4$alkyl and phenyl optionally substituted with 1 to 2 halogen atoms or $C_1$-$C_4$ alkyl optionally substituted with halogen;

or a tautomer or pharmaceutically acceptable salt thereof.

2. The compound according to claim 1 wherein
$R^1$ is methyl, ethyl, n-propyl, isopropyl, n-butyl, isobutyl, tert-butyl, n-pentyl, n-hexyl, n-heptyl, n-octyl, n-nonyl, n-decyl, cyclobutyl, cyclopentyl, cyclohexyl, cycloheptyl, cyclooctyl, bicylco(3.3.0)octanyl, or bicyclo[4.3.0]nonyl each optionally independently substituted with 1 to 3 substituents chosen from methyl, ethyl, cyclopropyl, cyclobutyl, cyclohexyl, fluoro, chloro and bromo;

$R^2$ and $R^3$ are independently hydrogen, methyl, ethyl, n-propyl, isopropyl, isobutyl, tert-butyl, wherein $R^2$ and $R^3$ cannot simultaneously be hydrogen, or $R^2$ and $R^3$ together with the carbon to which they are attached form a cyclopropyl, cyclobutyl, cyclopentyl, cyclohexyl or tetrahydropyranyl ring;

$R^4$ is hydrogen;

$R^5$ is phenyl, naphthyl, pyridinyl, quinolinyl, isoquinolinyl, pyrrolyl, pyrazolyl, imidazolyl, oxazolyl, isoxazolyl, thiazolyl, isothiazolyl, triazolyl, oxadiazolyl, thiadiazolyl, indolyl, benzoxazolyl, benzopyrazolyl, benzoisoxazolyl, benzothiazolyl, benzoisothiazolyl, benzimidazolyl, tetrahydrobenzoxazolyl, tetrahydrobenzothiazolyl, or tetrahydrobenzimidazolyl each optionally independently substituted with 1 to 3 substituents chosen from $C_1$-$C_6$ alkyl optionally substituted with 1 to 3 halogen atoms, $C_3$-$C_6$ cycloalkyl, halogen, cyano, dimethylamino$C_1$-$C_4$alkyl and phenyl optionally substituted with 1 to 2 halogen atoms or $C_1$-$C_4$ alkyl optionally substituted with halogen.

3. The compound according to claim 1 wherein
$R^1$ is benzyl or phenethyl each optionally independently substituted with 1 to 3 substituents chosen from methyl, fluoro, chloro and bromo.

4. The compound according to claim 1 wherein
$R^1$ is methyl, ethyl, n-propyl, isopropyl, tert-butyl, n-butyl, cyclopropyl, cyclopentyl, cyclohexyl, cycloheptyl or benzyl each optionally substituted with methyl, cyclopropyl, cyclobutyl, cyclohexyl and chloro;
$R^2$ and $R^3$ are independently hydrogen, methyl, isopropyl, tert-butyl, wherein $R^2$ and $R^3$ cannot simultaneously be hydrogen, or $R^2$ and $R^3$ together with the carbon to which they are attached form a cyclopropyl or cyclobutyl, ring;
$R^4$ is hydrogen;
$R^5$ is phenyl, pyridinyl, quinolinyl, isoquinolinyl, pyrazolyl, isoxazolyl, benzothiazolyl, thiadiazolyl, or thiazolyl each optionally independently substituted with 1 to 2 substituents chosen from, methyl, ethyl, tert-butyl, neopentyl, cyclohexyl, trifluoromethyl or phenyl optionally substituted with a chlorine atom.

5. A compound chosen from
N-(5-tert-Butyl-isoxazol-3-yl)-2-cyclohexanesulfonyl-2-methyl-propionamide
N-(4-tert-Butyl-thiazol-2-yl)-2-methyl-2-(propane-2-sulfonyl)-propionamide
N-(5-tert-Butyl-4-methyl-thiazol-2-yl)-2-methyl-2-(propane-2-sulfonyl)-propionamide
1-Cyclohexanesulfonyl-cyclobutanecarboxylic acid (5-tert-butyl-isoxazol-3-yl)-amide
1-Cyclohexanesulfonyl-cyclobutanecarboxylic acid (4-tert-butyl-thiazol-2-yl)-amide
N-(5-tert-Butyl-isoxazol-3-yl)-2-methyl-2-(propane-2-sulfonyl)-propionamide
N-(4-tert-Butyl-thiazol-2-yl)-2-(4-chloro-phenyl-methanesulfonyl)-2-methyl-propionamide
N-(5-tert-Butyl-4-methyl-thiazol-2-yl)-2-(4-chloro-phenylmethanesulfonyl)-2-methyl-propionamide
N-(5-tert-Butyl-isoxazol-3-yl)-2-(4-chloro-phenyl-methanesulfonyl)-2-methyl-propionamide
N-(5-tert-Butyl-isoxazol-3-yl)-2-methyl-2-(propane-1-sulfonyl)-propionamide
2-Methyl-2-(propane-1-sulfonyl)-N-(4-trifluoromethyl-pyridin-2-yl)-propionamide
2-Methyl-N-naphthalen-2-yl-2-(propane-2-sulfonyl)-propionamide
N-Isoquinolin-3-yl-2-methyl-2-(propane-2-sulfonyl)-propionamide
N-(4-tert-Butyl-thiazol-2-yl)-2-methyl-2-(propane-1-sulfonyl)-propionamide
2-Methyl-2-(propane-2-sulfonyl)-N-quinolin-3-yl-propionamide
N-(4-tert-Butyl-phenyl)-2-methyl-2-(propane-2-sulfonyl)-propionamide
2-Methyl-N-(4-phenyl-thiazol-2-yl)-2-(propane-2-sulfonyl)-propionamide
2-Methyl-N-(2-methyl-5-phenyl-2H-pyrazol-3-yl)-2-(propane-2-sulfonyl)-propionamide
N-(5-tert-Butyl-2-methyl-2H-pyrazol-3-yl)-2-methyl-2-(propane-2-sulfonyl)-propionamide
N-(3-tert-Butyl-phenyl)-2-methyl-2-(propane-2-sulfonyl)-propionamide
2-Methyl-2-(propane-2-sulfonyl)-N-(6-trifluoromethyl-pyridin-2-yl)-propionamide
N-(4-tert-Butyl-thiazol-2-yl)-2-cyclopentanesulfonyl-2-methyl-propionamide
2-Cyclohexanesulfonyl-2-methyl-N-(5-trifluoromethyl-pyridin-2-yl)-propionamide
N-(5-tert-Butyl-isoxazol-3-yl)-2-cyclopentanesulfonyl-2-methyl-propionamide
N-(5-tert-Butyl-isoxazol-3-yl)-2-cyclopropanesulfonyl-2-methyl-propionamide
N-(5-tert-Butyl-isoxazol-3-yl)-2-methyl-2-(2-methyl-propane-2-sulfonyl)-propionamide
N-(4-tert-Butyl-thiazol-2-yl)-2-methyl-2-(2-methyl-propane-2-sulfonyl)-propionamide
N-(5-tert-Butyl-4-methyl-thiazol-2-yl)-2-methyl-2-(2-methyl-propane-2-sulfonyl)-propionamide
N-(5-tert-Butyl-2-methyl-2H-pyrazol-3-yl)-2-methyl-2-(2-methyl-propane-2-sulfonyl)-propionamide
2-Methyl-2-(2-methyl-propane-2-sulfonyl)-N-(6-trifluoromethyl-pyridin-2-yl)-propionamide
2-Methyl-2-(2-methyl-propane-2-sulfonyl)-N-(4-trifluoromethyl-pyridin-2-yl)-propionamide
N-(5-tert-Butyl-isoxazol-3-yl)-3-methyl-2-(propane-2-sulfonyl)-butyramide
2-(Butane-2-sulfonyl)-N-(5-tert-butyl-isoxazol-3-yl)-2-methyl-propionamide
2-(Butane-2-sulfonyl)-N-(5-tert-butyl-2-methyl-2H-pyrazol-3-yl)-2-methyl-propionamide
2-(Butane-2-sulfonyl)-N-(4-tert-butyl-thiazol-2-yl)-2-methyl-propionamide
N-(4-tert-Butyl-thiazol-2-yl)-2-(propane-2-sulfonyl)-propionamide
N-(4-tert-Butyl-thiazol-2-yl)-3-methyl-2-(propane-2-sulfonyl)-butyramide
N-(5-tert-Butyl-4-methyl-thiazol-2-yl)-3-methyl-2-(propane-2-sulfonyl)-butyramide
2-(Butane-2-sulfonyl)-2-methyl-N-(5-trifluoromethyl-pyridin-2-yl)-propionamide
N-(5-tert-Butyl-2-methyl-2H-pyrazol-3-yl)-2-ethanesulfonyl-2-methyl-propionamide
N-(5-tert-Butyl-2-methyl-2H-pyrazol-3-yl)-2-methanesulfonyl-2-methyl-propionamide
N-(4-tert-Butyl-thiazol-2-yl)-2-methanesulfonyl-2-methyl-propionamide
N-(5-tert-Butyl-isoxazol-3-yl)-2-methyl-2-(2-methyl-propane-1-sulfonyl)-propionamide
N-(5-tert-Butyl-isoxazol-3-yl)-2-methyl-2-(2,2,2-trifluoro-ethanesulfonyl)-propionamide
N-(5-tert-Butyl-isoxazol-3-yl)-2-methanesulfonyl-2-methyl-propionamide
N-(5-tert-Butyl-2-methyl-2H-pyrazol-3-yl)-2-cyclopentanesulfonyl-2-methyl-propionamide
2-Cyclopentanesulfonyl-2-methyl-N-(2-methyl-5-phenyl-2H-pyrazol-3-yl)-propionamide
2-Cyclopentanesulfonyl-2-methyl-N-(5-trifluoromethyl-pyridin-2-yl)-propionamide
2-Cyclopentanesulfonyl-2-methyl-N-(4-trifluoromethyl-thiazol-2-yl)-propionamide
N-[4-(4-Chloro-phenyl)-thiazol-2-yl]-2-cyclopentanesulfonyl-2-methyl-propionamide
2-Cyclopentanesulfonyl-2-methyl-N-(4-trifluoromethyl-pyridin-2-yl)-propionamide
N-(5-tert-Butyl-2-methyl-2H-pyrazol-3-yl)-2-cyclobutyl-methanesulfonyl-2-methyl-propionamide
N-(5-tert-Butyl-2-methyl-2H-pyrazol-3-yl)-2-(hexane-3-sulfonyl)-2-methyl-propionamide N-(3-tert-Butyl-isoxazol-5-yl)-2-cyclohexanesulfonyl-2-methyl-propionamide
N-(5-tert-Butyl-isoxazol-3-yl)-2-cyclohexylmethane-sulfonyl-2-methyl-propionamide
N-(5-tert-Butyl-isoxazol-3-yl)-2-ethanesulfonyl-2-methyl-propionamide
N-(5-tert-Butyl-isoxazol-3-yl)-2-cyanomethanesulfonyl-2-methyl-propionamide
N-(5-tert-Butyl-2-methyl-2H-pyrazol-3-yl)-2-(2,2-dimethyl-propane-1-sulfonyl)-2-methyl-propionamide
N-(5-tert-Butyl-2-methyl-2H-pyrazol-3-yl)-2-cycloheptanesulfonyl-2-methyl-propionamide
N-(5-tert-Butyl-2-methyl-2H-pyrazol-3-yl)-2-cyclohexylmethanesulfonyl-2-methyl-propionamide
2-(3,3-Dimethyl-2-oxo-butane-1-sulfonyl)-2-methyl-N-(5-trifluoromethyl-pyridin-2-yl)-propionamide
N-(5-tert-Butyl-isoxazol-3-yl)-2-(3,3-dimethyl-2-oxo-butane-1-sulfonyl)-2-methyl-propionamide
N-(5-tert-Butyl-isoxazol-3-yl)-2-methyl-2-(3-methyl-butane-1-sulfonyl)-propionamide
N-(5-tert-Butyl-2-methyl-2H-pyrazol-3-yl)-2-methyl-2-(3-methyl-butane-1-sulfonyl)-propionamide
N-(5-tert-Butyl-isoxazol-3-yl)-2-cycloheptanesulfonyl-2-methyl-propionamide
2-Cyclohexylmethanesulfonyl-2-methyl-N-(5-trifluoromethyl-pyridin-2-yl)-propionamide
2-Methyl-2-(3-methyl-butane-1-sulfonyl)-N-(5-trifluoromethyl-pyridin-2-yl)-propionamide
2-Cycloheptanesulfonyl-2-methyl-N-(5-trifluoromethyl-pyridin-2-yl)-propionamide
2-Cyclopropylmethanesulfonyl-2-methyl-N-(5-trifluoromethyl-pyridin-2-yl)-propionamide
2-Cyclobutylmethanesulfonyl-2-methyl-N-(5-trifluoromethyl-pyridin-2-yl)-propionamide
N-(5-tert-Butyl-isoxazol-3-yl)-2-cyclopropylmethanesulfonyl-2-methyl-propionamide
N-(5-tert-Butyl-isoxazol-3-yl)-2-cyclobutylmethanesulfonyl-2-methyl-propionamide
N-(5-tert-Butyl-isoxazol-3-yl)-2-methyl-2-(3-phenyl-propane-1-sulfonyl)-propionamide
N-(3-tert-Butyl-isoxazol-5-yl)-2-methyl-2-(propane-2-sulfonyl)-propionamide
N-[4-(4-Chloro-phenyl)-thiazol-2-yl]-2-methyl-2-(propane-2-sulfonyl)-propionamide
2-Methyl-2-(propane-2-sulfonyl)-N-quinolin-2-yl-propionamide
2-Methyl-2-(propane-1-sulfonyl)-N-quinolin-3-yl-propionamide
N-(4-tert-Butyl-phenyl)-2-methyl-2-(propane-1-sulfonyl)-propionamide
2-Methyl-2-(propane-1-sulfonyl)-N-(4,5,6,7-tetrahydro-benzothiazol-2-yl)-propionamide
2-Methyl-2-(propane-1-sulfonyl)-N-quinolin-2-yl-propionamide
N-[4-(4-Chloro-phenyl)-thiazol-2-yl]-2-methyl-2-(propane-1-sulfonyl)-propionamide
2-Methyl-N-(2-methyl-5-phenyl-2H-pyrazol-3-yl)-2-(propane-1-sulfonyl)-propionamide
N-(5-tert-Butyl-2-methyl-2H-pyrazol-3-yl)-2-methyl-2-(propane-1-sulfonyl)-propionamide
N-(3-tert-Butyl-phenyl)-2-methyl-2-(propane-1-sulfonyl)-propionamide
2-Methyl-2-(propane-1-sulfonyl)-N-(4-trifluoromethyl-thiazol-2-yl)-propionamide
N-(3-tert-Butyl-isoxazol-5-yl)-2-methyl-2-(propane-1-sulfonyl)-propionamide
N-Benzothiazol-2-yl-2-methyl-2-(propane-1-sulfonyl)-propionamide
2-Methyl-2-(propane-1-sulfonyl)-N-(5-trifluoromethyl-pyridin-2-yl)-propionamide
2-Methyl-N-(5-methyl-4-phenyl-thiazol-2-yl)-2-(propane-1-sulfonyl)-propionamide
N-(5-Ethyl-4-phenyl-thiazol-2-yl)-2-methyl-2-(propane-1-sulfonyl)-propionamide
2-Methyl-N-(5-phenyl-pyridin-2-yl)-2-(propane-1-sulfonyl)-propionamide
N-(4-Cyclohexyl-thiazol-2-yl)-2-methyl-2-(propane-1-sulfonyl)-propionamide
N-(5-tert-Butyl-4-methyl-thiazol-2-yl)-2-methyl-2-(propane-1-sulfonyl)-propionamide
N-(2,4-Dimethyl-5-phenyl-2H-pyrazol-3-yl)-2-methyl-2-(propane-1-sulfonyl)-propionamide
N-[3-(2,2-Dimethyl-propyl)-isoxazol-5-yl]-2-methyl-2-(propane-1-sulfonyl)-propionamide
N-(5-tert-Butyl-1,3,4-thiadiazol-2-yl)-2-cyclopentanesulfonyl-2-methyl-propionamide
2-Cyclopentanesulfonyl-2-methyl-N-(5-phenyl-4H-1,2,4-triazol-3-yl)-propionamide
N-(3-tert-Butyl-isoxazol-5-yl)-2-cyclobutylmethanesulfonyl-2-methyl-propionamide
N-(3-tert-Butyl-isoxazol-5-yl)-2-cyclopropylmethanesulfonyl-2-methyl-propionamide
N-(3-tert-Butyl-isoxazol-5-yl)-2-methyl-2-(3-methyl-butane-1-sulfonyl)-propionamide
N-(3-tert-Butyl-isoxazol-5-yl)-2-cyclopentanesulfonyl-2-methyl-propionamide
N-(3-tert-Butyl-isoxazol-5-yl)-2-cyclohexylmethanesulfonyl-2-methyl-propionamide
2-(Butane-2-sulfonyl)-N-(3-tert-butyl-isoxazol-5-yl)-2-methyl-propionamide
N-(3-tert-Butyl-isoxazol-5-yl)-2-methyl-2-(2-methyl-propane-1-sulfonyl)-propionamide and
N-(3-tert-Butyl-isoxazol-5-yl)-2-(4-fluoro-phenyl-methanesulfonyl)-2-methyl-propionamide
or a tautomer or pharmaceutically acceptable salt thereof.

6. A compound chosen from
N-(5-tert-Butyl-isoxazol-3-yl)-2-cyclohexanesulfonyl-2-methyl-propionamide
N-(4-tert-Butyl-thiazol-2-yl)-2-methyl-2-(propane-2-sulfonyl)-propionamide
N-(5-tert-Butyl-4-methyl-thiazol-2-yl)-2-methyl-2-(propane-2-sulfonyl)-propionamide
1-Cyclohexanesulfonyl-cyclobutanecarboxylic acid (5-tert-butyl-isoxazol-3-yl)-amide
N-(5-tert-Butyl-isoxazol-3-yl)-2-methyl-2-(propane-2-sulfonyl)-propionamide
N-(4-tert-Butyl-thiazol-2-yl)-2-(4-chloro-phenyl-methanesulfonyl)-2-methyl-propionamide
N-(5-tert-Butyl-4-methyl-thiazol-2-yl)-2-(4-chloro-phenylmethanesulfonyl)-2-methyl-propionamide
N-(5-tert-Butyl-isoxazol-3-yl)-2-(4-chloro-phenyl-methanesulfonyl)-2-methyl-propionamide
N-(5-tert-Butyl-isoxazol-3-yl)-2-methyl-2-(propane-1-sulfonyl)-propionamide
N-(4-tert-Butyl-thiazol-2-yl)-2-methyl-2-(propane-1-sulfonyl)-propionamide
N-(4-tert-Butyl-phenyl)-2-methyl-2-(propane-2-sulfonyl)-propionamide
N-(3-tert-Butyl-phenyl)-2-methyl-2-(propane-2-sulfonyl)-propionamide
N-(4-tert-Butyl-thiazol-2-yl)-2-cyclopentanesulfonyl-2-methyl-propionamide 2-Cyclohexanesulfonyl-2-methyl-N-(5-trifluoromethyl-pyridin-2-yl)-propionamide
N-(5-tert-Butyl-isoxazol-3-yl)-2-cyclopentanesulfonyl-2-methyl-propionamide
N-(5-tert-Butyl-isoxazol-3-yl)-2-cyclopropanesulfonyl-2-methyl-propionamide
N-(5-tert-Butyl-isoxazol-3-yl)-2-methyl-2-(2-methyl-propane-2-sulfonyl)-propionamide
N-(4-tert-Butyl-thiazol-2-yl)-2-methyl-2-(2-methyl-propane-2-sulfonyl)-propionamide
N-(5-tert-Butyl-4-methyl-thiazol-2-yl)-2-methyl-2-(2-methyl-propane-2-sulfonyl)-propionamide
2-(Butane-2-sulfonyl)-N-(5-tert-butyl-isoxazol-3-yl)-2-methyl-propionamide
2-(Butane-2-sulfonyl)-N-(4-tert-butyl-thiazol-2-yl)-2-methyl-propionamide
N-(4-tert-Butyl-thiazol-2-yl)-3-methyl-2-(propane-2-sulfonyl)-butyramide
N-(5-tert-Butyl-4-methyl-thiazol-2-yl)-3-methyl-2-(propane-2-sulfonyl)-butyramide
N-(5-tert-Butyl-isoxazol-3-yl)-2-methyl-2-(2-methyl-propane-1-sulfonyl)-propionamide
2-Cyclopentanesulfonyl-2-methyl-N-(5-trifluoromethyl-pyridin-2-yl)-propionamide
N-[4-(4-Chloro-phenyl)-thiazol-2-yl]-2-cyclopentane-sulfonyl-2-methyl-propionamide
2-Cyclopentanesulfonyl-2-methyl-N-(4-trifluoromethyl-pyridin-2-yl)-propionamide
N-(5-tert-Butyl-2-methyl-2H-pyrazol-3-yl)-2-cyclobutyl-methanesulfonyl-2-methyl-propionamide
N-(5-tert-Butyl-2-methyl-2H-pyrazol-3-yl)-2-(hexane-3-sulfonyl)-2-methyl-propionamide
N-(3-tert-Butyl-isoxazol-5-yl)-2-cyclohexanesulfonyl-2-methyl-propionamide
N-(5-tert-Butyl-isoxazol-3-yl)-2-cyclohexylmethane-sulfonyl-2-methyl-propionamide
N-(5-tert-Butyl-2-methyl-2H-pyrazol-3-yl)-2-cycloheptanesulfonyl-2-methyl-propionamide
N-(5-tert-Butyl-2-methyl-2H-pyrazol-3-yl)-2-cyclohexylmethanesulfonyl-2-methyl-propionamide
2-(3,3-Dimethyl-2-oxo-butane-1-sulfonyl)-2-methyl-N-(5-trifluoromethyl-pyridin-2-yl)-propionamide
N-(5-tert-Butyl-isoxazol-3-yl)-2-(3,3-dimethyl-2-oxo-butane-1-sulfonyl)-2-methyl-propionamide
N-(5-tert-Butyl-isoxazol-3-yl)-2-methyl-2-(3-methyl-butane-1-sulfonyl)-propionamide
N-(5-tert-Butyl-2-methyl-2H-pyrazol-3-yl)-2-methyl-2-(3-methyl-butane-1-sulfonyl)-propionamide
N-(5-tert-Butyl-isoxazol-3-yl)-2-cycloheptanesulfonyl-2-methyl-propionamide
2-Cyclohexylmethanesulfonyl-2-methyl-N-(5-trifluoromethyl-pyridin-2-yl)-propionamide
2-Methyl-2-(3-methyl-butane-1-sulfonyl)-N-(5-trifluoromethyl-pyridin-2-yl)-propionamide
2-Cycloheptanesulfonyl-2-methyl-N-(5-trifluoromethyl-pyridin-2-yl)-propionamide
2-Cyclopropylmethanesulfonyl-2-methyl-N-(5-trifluoromethyl-pyridin-2-yl)-propionamide
2-Cyclobutylmethanesulfonyl-2-methyl-N-(5-trifluoromethyl-pyridin-2-yl)-propionamide
N-(5-tert-Butyl-isoxazol-3-yl)-2-cyclopropylmethane-sulfonyl-2-methyl-propionamide
N-(5-tert-Butyl-isoxazol-3-yl)-2-cyclobutylmethane-sulfonyl-2-methyl-propionamide
N-(3-tert-Butyl-isoxazol-5-yl)-2-methyl-2-(propane-2-sulfonyl)-propionamide
N-[4-(4-Chloro-phenyl)-thiazol-2-yl]-2-methyl-2-(propane-2-sulfonyl)-propionamide
2-Methyl-2-(propane-2-sulfonyl)-N-quinolin-2-yl-propionamide
2-Methyl-2-(propane-1-sulfonyl)-N-quinolin-3-yl-propionamide
N-(4-tert-Butyl-phenyl)-2-methyl-2-(propane-1-sulfonyl)-propionamide
2-Methyl-2-(propane-1-sulfonyl)-N-quinolin-2-yl-propionamide
N-[4-(4-Chloro-phenyl)-thiazol-2-yl]-2-methyl-2-(propane-1-sulfonyl)-propionamide
N-(3-tert-Butyl-phenyl)-2-methyl-2-(propane-1-sulfonyl)-propionamide
N-(3-tert-Butyl-isoxazol-5-yl)-2-methyl-2-(propane-1-sulfonyl)-propionamide
N-Benzothiazol-2-yl-2-methyl-2-(propane-1-sulfonyl)-propionamide
2-Methyl-N-(5-methyl-4-phenyl-thiazol-2-yl)-2-(propane-1-sulfonyl)-propionamide
N-(5-Ethyl-4-phenyl-thiazol-2-yl)-2-methyl-2-(propane-1-sulfonyl)-propionamide
N-(4-Cyclohexyl-thiazol-2-yl)-2-methyl-2-(propane-1-sulfonyl)-propionamide
N-(5-tert-Butyl-4-methyl-thiazol-2-yl)-2-methyl-2-(propane-1-sulfonyl)-propionamide
N-[3-(2,2-Dimethyl-propyl)-isoxazol-5-yl]-2-methyl-2-(propane-1-sulfonyl)-propionamide
N-(5-tert-Butyl-1,3,4-thiadiazol-2-yl)-2-cyclopentane-sulfonyl-2-methyl-propionamide
2-Cyclopentanesulfonyl-2-methyl-N-(5-phenyl-4H-1,2,4-triazol-3-yl)-propionamide
N-(3-tert-Butyl-isoxazol-5-yl)-2-cyclobutylmethane-sulfonyl-2-methyl-propionamide
N-(3-tert-Butyl-isoxazol-5-yl)-2-cyclopropylmethane-sulfonyl-2-methyl-propionamide
N-(3-tert-Butyl-isoxazol-5-yl)-2-methyl-2-(3-methyl-butane-1-sulfonyl)-propionamide
N-(3-tert-Butyl-isoxazol-5-yl)-2-cyclopentanesulfonyl-2-methyl-propionamide
N-(3-tert-Butyl-isoxazol-5-yl)-2-cyclohexylmethane-sulfonyl-2-methyl-propionamide
2-(Butane-2-sulfonyl)-N-(3-tert-butyl-isoxazol-5-yl)-2-methyl-propionamide
and
N-(3-tert-Butyl-isoxazol-5-yl)-2-methyl-2-(2-methyl-propane-1-sulfonyl)-propionamide
or a tautomer or pharmaceutically acceptable salt thereof.

7. A compound chosen from
N-(5-tert-Butyl-isoxazol-3-yl)-2-cyclohexanesulfonyl-2-methyl-propionamide
N-(5-tert-Butyl-4-methyl-thiazol-2-yl)-2-methyl-2-(propane-2-sulfonyl)-propionamide
1-Cyclohexanesulfonyl-cyclobutanecarboxylic acid (5-tert-butyl-isoxazol-3-yl)-amide
N-(5-tert-Butyl-4-methyl-thiazol-2-yl)-2-(4-chloro-phenylmethanesulfonyl)-2-methyl-propionamide
N-(5-tert-Butyl-isoxazol-3-yl)-2-(4-chloro-phenyl-methanesulfonyl)-2-methyl-propionamide
N-(5-tert-Butyl-isoxazol-3-yl)-2-methyl-2-(propane-1-sulfonyl)-propionamide
N-(4-tert-Butyl-thiazol-2-yl)-2-methyl-2-(propane-1-sulfonyl)-propionamide
2-Cyclohexanesulfonyl-2-methyl-N-(5-trifluoromethyl-pyridin-2-yl)-propionamide
N-(5-tert-Butyl-isoxazol-3-yl)-2-cyclopentanesulfonyl-2-methyl-propionamide N-(4-tert-Butyl-thiazol-2-yl)-2-methyl-2-(2-methyl-propane-2-sulfonyl)-propionamide
N-(5-tert-Butyl-4-methyl-thiazol-2-yl)-2-methyl-2-(2-methyl-propane-2-sulfonyl)-propionamide
2-(Butane-2-sulfonyl)-N-(5-tert-butyl-isoxazol-3-yl)-2-methyl-propionamide
2-(Butane-2-sulfonyl)-N-(4-tert-butyl-thiazol-2-yl)-2-methyl-propionamide
N-(5-tert-Butyl-isoxazol-3-yl)-2-methyl-2-(2-methyl-propane-1-sulfonyl)-propionamide
N-[4-(4-Chloro-phenyl)-thiazol-2-yl]-2-cyclopentanesulfonyl-2-methyl-propionamide
N-(5-tert-Butyl-2-methyl-2H-pyrazol-3-yl)-2-cyclobutylmethanesulfonyl-2-methyl-propionamide
N-(3-tert-Butyl-isoxazol-5-yl)-2-cyclohexanesulfonyl-2-methyl-propionamide
N-(5-tert-Butyl-isoxazol-3-yl)-2-cyclohexylmethanesulfonyl-2-methyl-propionamide
N-(5-tert-Butyl-2-methyl-2H-pyrazol-3-yl)-2-cycloheptanesulfonyl-2-methyl-propionamide
N-(5-tert-Butyl-2-methyl-2H-pyrazol-3-yl)-2-cyclohexylmethanesulfonyl-2-methyl-propionamide
2-(3,3-Dimethyl-2-oxo-butane-1-sulfonyl)-2-methyl-N-(5-trifluoromethyl-pyridin-2-yl)-propionamide
N-(5-tert-Butyl-isoxazol-3-yl)-2-(3,3-dimethyl-2-oxo-butane-1-sulfonyl)-2-methyl-propionamide
N-(5-tert-Butyl-isoxazol-3-yl)-2-methyl-2-(3-methyl-butane-1-sulfonyl)-propionamide
N-(5-tert-Butyl-2-methyl-2H-pyrazol-3-yl)-2-methyl-2-(3-methyl-butane-1-sulfonyl)-propionamide
N-(5-tert-Butyl-isoxazol-3-yl)-2-cycloheptanesulfonyl-2-methyl-propionamide
2-Cyclohexylmethanesulfonyl-2-methyl-N-(5-trifluoromethyl-pyridin-2-yl)-propionamide
2-Methyl-2-(3-methyl-butane-1-sulfonyl)-N-(5-trifluoromethyl-pyridin-2-yl)-propionamide
2-Cycloheptanesulfonyl-2-methyl-N-(5-trifluoromethyl-pyridin-2-yl)-propionamide
N-(5-tert-Butyl-isoxazol-3-yl)-2-cyclopropylmethanesulfonyl-2-methyl-propionamide
N-(5-tert-Butyl-isoxazol-3-yl)-2-cyclobutylmethanesulfonyl-2-methyl-propionamide
N-[4-(4-Chloro-phenyl)-thiazol-2-yl]-2-methyl-2-(propane-2-sulfonyl)-propionamide
N-(4-tert-Butyl-phenyl)-2-methyl-2-(propane-1-sulfonyl)-propionamide
N-[4-(4-Chloro-phenyl)-thiazol-2-yl]-2-methyl-2-(propane-1-sulfonyl)-propionamide
N-(3-tert-Butyl-isoxazol-5-yl)-2-methyl-2-(propane-1-sulfonyl)-propionamide
2-Methyl-N-(5-methyl-4-phenyl-thiazol-2-yl)-2-(propane-1-sulfonyl)-propionamide
N-(5-Ethyl-4-phenyl-thiazol-2-yl)-2-methyl-2-(propane-1-sulfonyl)-propionamide
N-(4-Cyclohexyl-thiazol-2-yl)-2-methyl-2-(propane-1-sulfonyl)-propionamide
N-(5-tert-Butyl-4-methyl-thiazol-2-yl)-2-methyl-2-(propane-1-sulfonyl)-propionamide
N-(5-tert-Butyl-1,3,4-thiadiazol-2-yl)-2-cyclopentanesulfonyl-2-methyl-propionamide
2-Cyclopentanesulfonyl-2-methyl-N-(5-phenyl-4H-1,2,4-triazol-3-yl)-propionamide
N-(3-tert-Butyl-isoxazol-5-yl)-2-cyclobutylmethanesulfonyl-2-methyl-propionamide
N-(3-tert-Butyl-isoxazol-5-yl)-2-cyclopropylmethanesulfonyl-2-methyl-propionamide
N-(3-tert-Butyl-isoxazol-5-yl)-2-methyl-2-(3-methyl-butane-1-sulfonyl)-propionamide
N-(3-tert-Butyl-isoxazol-5-yl)-2-cyclopentanesulfonyl-2-methyl-propionamide
N-(3-tert-Butyl-isoxazol-5-yl)-2-cyclohexylmethanesulfonyl-2-methyl-propionamide
2-(Butane-2-sulfonyl)-N-(3-tert-butyl-isoxazol-5-yl)-2-methyl-propionamide
N-(3-tert-Butyl-isoxazol-5-yl)-2-methyl-2-(2-methyl-propane-1-sulfonyl)-propionamide and
N-(3-tert-Butyl-isoxazol-5-yl)-2-(4-fluoro-phenylmethanesulfonyl)-2-methyl-propionamide
or a tautomer or pharmaceutically acceptable salt thereof.

8. A pharmaceutical composition comprising a therapeutically effective amount of a compound according to claim 1.

* * * * *